(12) United States Patent
Altarac et al.

(10) Patent No.: US 8,226,690 B2
(45) Date of Patent: Jul. 24, 2012

(54) SYSTEMS AND METHODS FOR STABILIZATION OF BONE STRUCTURES

(75) Inventors: Moti Altarac, Irvine, CA (US); Joey Reglos, Lake Forest, CA (US); Stanley Kyle Hayes, Mission Viejo, CA (US); Daniel H. Kim, Los Altos, CA (US); J. Christopher Flaherty, Topsfield, MA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 1049 days.

(21) Appl. No.: 11/362,366

(22) Filed: Feb. 23, 2006

(65) Prior Publication Data
US 2007/0043359 A1    Feb. 22, 2007

Related U.S. Application Data

(60) Provisional application No. 60/701,660, filed on Jul. 22, 2005.

(51) Int. Cl.
*A61B 17/70* (2006.01)
(52) U.S. Cl. ......... 606/256; 606/246; 606/254; 606/257
(58) Field of Classification Search .................. None
See application file for complete search history.

(56) References Cited

U.S. PATENT DOCUMENTS

| | | | |
|---|---|---|---|
| 602,580 A | 4/1898 | Haskins et al. |
| 802,844 A | 10/1905 | Covell et al. |
| 2,790,437 A | 4/1957 | Moore |
| 4,545,374 A | 10/1985 | Jacobson |
| 4,611,582 A | 9/1986 | Duff |
| 4,743,260 A | 5/1988 | Burton |
| 4,858,601 A | 8/1989 | Glisson |
| 4,959,064 A | 9/1990 | Engelhardt |
| 5,015,247 A | 5/1991 | Michelson |
| 5,062,845 A | 11/1991 | Kuslich et al. |
| 5,092,866 A | 3/1992 | Breard et al. |
| 5,129,388 A | 7/1992 | Vignaud et al. |
| 5,171,279 A | 12/1992 | Mathews |

(Continued)

FOREIGN PATENT DOCUMENTS
EP    0767636    4/1997
(Continued)

OTHER PUBLICATIONS

Non-Final Office Action for U.S. Appl. No. 11/006,495, Mail Date Jun. 30, 2008, 27 pages.

(Continued)

*Primary Examiner* — Thomas C. Barrett
*Assistant Examiner* — Christine Nelson
(74) *Attorney, Agent, or Firm* — Meyertons, Hood, Kivlin, Kowert & Goetzel, P.C.; Eric B. Meyertons

(57) ABSTRACT

Methods, systems, devices and tools for placing bone stabilization components in a patient are provided. The systems and devices have a reduced number of discrete components that allow placement through small incisions and tubes. More particularly, the present invention is directed to systems and methods of treating the spine, which eliminate pain and enable spinal motion, which effectively mimics that of a normally functioning spine. Methods are also provided for stabilizing the spine and for implanting the subject systems.

60 Claims, 59 Drawing Sheets

U.S. PATENT DOCUMENTS

| | | |
|---|---|---|
| 5,180,393 A | 1/1993 | Commarmond et al. |
| 5,207,678 A | 5/1993 | Harms et al. |
| 5,282,863 A | 2/1994 | Burton |
| 5,368,594 A | 11/1994 | Martin et al. |
| 5,370,646 A | 12/1994 | Reese et al. |
| 5,375,823 A | 12/1994 | Navas et al. |
| 5,387,212 A | 2/1995 | Yuan et al. |
| 5,415,661 A | 5/1995 | Holmes |
| 5,437,669 A | 8/1995 | Yuan et al. |
| 5,437,672 A | 8/1995 | Alleyne |
| 5,443,467 A | 8/1995 | Biedermann |
| 5,449,355 A | 9/1995 | Rhum et al. |
| 5,474,555 A | 12/1995 | Puno et al. |
| 5,480,401 A | 1/1996 | Navas et al. |
| 5,484,437 A | 1/1996 | Michelson |
| 5,489,308 A | 2/1996 | Kuslich et al. |
| 5,522,843 A | 6/1996 | Zang |
| 5,527,312 A | 6/1996 | Ray |
| 5,540,688 A | 7/1996 | Navas et al. |
| 5,571,191 A | 11/1996 | Fitz |
| 5,609,636 A | 3/1997 | Kohrs et al. |
| 5,616,142 A | 4/1997 | Yuan et al. |
| 5,645,599 A | 7/1997 | Samani |
| 5,658,337 A | 8/1997 | Kohrs et al. |
| 5,672,175 A | 9/1997 | Martin |
| 5,720,751 A | 2/1998 | Jackson |
| 5,741,253 A | 4/1998 | Michelson |
| 5,776,135 A | 7/1998 | Errico et al. |
| 5,885,286 A | 3/1999 | Sherman et al. |
| 5,891,145 A | 4/1999 | Morrison et al. |
| RE36,211 E | 5/1999 | Nonomura |
| 5,964,761 A | 10/1999 | Kambin |
| 6,004,327 A | 12/1999 | Asnis et al. |
| 6,014,588 A | 1/2000 | Fitz |
| 6,033,406 A | 3/2000 | Mathews |
| 6,063,088 A | 5/2000 | Winslow |
| RE36,758 E | 6/2000 | Fitz |
| 6,080,155 A | 6/2000 | Michelson |
| 6,080,157 A | 6/2000 | Cathro et al. |
| 6,096,038 A | 8/2000 | Michelson |
| 6,132,464 A | 10/2000 | Martin |
| 6,200,322 B1 | 3/2001 | Branch et al. |
| 6,241,730 B1 | 6/2001 | Alby et al. |
| 6,248,105 B1 | 6/2001 | Schlapfer et al. |
| 6,261,293 B1 | 7/2001 | Nicholson et al. |
| 6,264,656 B1 | 7/2001 | Michelson |
| 6,267,764 B1 | 7/2001 | Elberg et al. |
| 6,267,765 B1 | 7/2001 | Taylor et al. |
| 6,270,498 B1 | 8/2001 | Michelson |
| 6,287,764 B1 | 9/2001 | Hildebrand et al. |
| 6,290,724 B1 | 9/2001 | Marino |
| 6,304,140 B1 | 10/2001 | Thron et al. |
| 6,306,140 B1 | 10/2001 | Siddiqui |
| 6,348,053 B1 | 2/2002 | Cachia |
| 6,375,657 B1 | 4/2002 | Doubler et al. |
| 6,419,703 B1 | 7/2002 | Fallin et al. |
| 6,440,133 B1 | 8/2002 | Beale et al. |
| 6,478,798 B1 | 11/2002 | Howland |
| 6,485,491 B1 | 11/2002 | Farris et al. |
| 6,485,518 B1 | 11/2002 | Cornwall et al. |
| 6,530,929 B1 | 3/2003 | Justis et al. |
| 6,533,790 B1 | 3/2003 | Liu |
| 6,540,747 B1 | 4/2003 | Marino |
| 6,547,795 B2 | 4/2003 | Schneiderman |
| 6,554,830 B1 | 4/2003 | Chappius |
| 6,558,390 B2 | 5/2003 | Cragg |
| 6,562,046 B2 | 5/2003 | Sasso |
| 6,565,565 B1 | 5/2003 | Yuan et al. |
| 6,565,573 B1 | 5/2003 | Ferrante et al. |
| 6,565,605 B2 | 5/2003 | Goble et al. |
| 6,579,319 B2 | 6/2003 | Goble et al. |
| 6,610,091 B1 | 8/2003 | Reiley |
| 6,626,904 B1 | 9/2003 | Jammet et al. |
| 6,626,905 B1 | 9/2003 | Schmiel et al. |
| 6,626,944 B1 | 9/2003 | Taylor et al. |
| 6,645,207 B2 | 11/2003 | Dixon et al. |
| 6,645,248 B2 | 11/2003 | Casutt et al. |
| 6,648,888 B1 | 11/2003 | Shluzas |
| 6,660,006 B2 | 12/2003 | Markworth et al. |
| 6,669,697 B1 | 12/2003 | Pisharodi |
| 6,669,729 B2 | 12/2003 | Chin |
| 6,676,661 B1 | 1/2004 | Benlloch et al. |
| 6,695,842 B2 | 2/2004 | Zucherman et al. |
| 6,699,247 B2 | 3/2004 | Zucherman et al. |
| 6,702,817 B2 | 3/2004 | Beger et al. |
| 6,709,434 B1 | 3/2004 | Gournay et al. |
| 6,716,214 B1 | 4/2004 | Jackson |
| 6,716,245 B2 | 4/2004 | Pasquet et al. |
| 6,726,687 B2 | 4/2004 | Jackson |
| 6,726,689 B2 | 4/2004 | Jackson |
| 6,730,089 B2 | 5/2004 | Jackson |
| 6,740,086 B2 | 5/2004 | Richelsoph |
| 6,740,090 B1 | 5/2004 | Cragg et al. |
| 6,749,613 B1 | 6/2004 | Conchy et al. |
| 6,749,614 B2 | 6/2004 | Teitelbaum et al. |
| 6,761,720 B1 | 7/2004 | Senegas |
| 6,770,075 B2 | 8/2004 | Howland |
| 6,783,527 B2 | 8/2004 | Drewry et al. |
| 6,786,903 B2 | 9/2004 | Lin |
| 6,790,209 B2 | 9/2004 | Beale et al. |
| 6,793,656 B1 | 9/2004 | Mathews |
| 6,802,844 B2 | 10/2004 | Ferree |
| 6,802,845 B2 | 10/2004 | Shirado et al. |
| 6,805,697 B1 | 10/2004 | Helm et al. |
| 6,811,567 B2 | 11/2004 | Reiley |
| 6,835,205 B2 | 12/2004 | Atkinson et al. |
| 6,835,207 B2 | 12/2004 | Zacouto et al. |
| 6,869,433 B2 | 3/2005 | Glascott |
| 6,875,212 B2 | 4/2005 | Shaolian et al. |
| 6,875,222 B2 | 4/2005 | Long et al. |
| 6,884,244 B1 | 4/2005 | Jackson |
| 6,896,677 B1 | 5/2005 | Lin |
| 6,899,716 B2 | 5/2005 | Cragg |
| 6,902,580 B2 | 6/2005 | Fallin et al. |
| 6,949,123 B2 | 9/2005 | Reiley |
| 6,966,910 B2 | 11/2005 | Ritland |
| 6,966,930 B2 | 11/2005 | Arnin et al. |
| 6,974,478 B2 | 12/2005 | Reiley et al. |
| 6,989,011 B2 | 1/2006 | Paul et al. |
| 6,997,927 B2 | 2/2006 | Jackson |
| 7,008,422 B2 | 3/2006 | Foley et al. |
| 7,011,660 B2 | 3/2006 | Sherman et al. |
| 7,011,685 B2 | 3/2006 | Arnin et al. |
| 7,029,475 B2 | 4/2006 | Panjabi |
| 7,033,358 B2 | 4/2006 | Taylor et al. |
| 7,041,136 B2 | 5/2006 | Goble et al. |
| 7,051,451 B2 | 5/2006 | Augostino et al. |
| 7,052,497 B2 | 5/2006 | Sherman et al. |
| 7,060,068 B2 | 6/2006 | Tromanhauser et al. |
| 7,066,939 B2 | 6/2006 | Taylor |
| 7,066,957 B2 | 6/2006 | Graf et al. |
| 7,070,598 B2 | 7/2006 | Lim et al. |
| 7,074,237 B2 | 7/2006 | Goble et al. |
| 7,074,238 B2 | 7/2006 | Stinson et al. |
| 7,079,883 B2 | 7/2006 | Marino et al. |
| 7,081,117 B2 | 7/2006 | Bono et al. |
| 7,083,621 B2 | 8/2006 | Shaolian et al. |
| 7,083,622 B2 | 8/2006 | Simonson |
| 7,083,649 B2 | 8/2006 | Zucherman et al. |
| 7,087,055 B2 | 8/2006 | Lim et al. |
| 7,087,057 B2 | 8/2006 | Konieczynski et al. |
| 7,087,084 B2 | 8/2006 | Reiley |
| 7,090,698 B2 | 8/2006 | Goble et al. |
| 7,101,398 B2 | 9/2006 | Dooris et al. |
| 7,108,705 B2 | 9/2006 | Davison et al. |
| 7,125,410 B2 | 10/2006 | Freudiger et al. |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,156,849 B2 | 1/2007 | Dunbar et al. |
| 7,160,300 B2 | 1/2007 | Jackson |
| 7,182,783 B2 | 2/2007 | Trieu |
| 7,188,626 B2 | 3/2007 | Foley et al. |
| 7,204,853 B2 | 4/2007 | Gordon et al. |
| 7,207,992 B2 | 4/2007 | Ritland |
| 7,214,227 B2 | 5/2007 | Colleran et al. |

| | | |
|---|---|---|
| 7,220,262 B1 | 5/2007 | Hynes |
| 7,229,441 B2 | 6/2007 | Trieu et al. |
| 7,250,052 B2 | 7/2007 | Landry et al. |
| 7,261,688 B2 | 8/2007 | Smith et al. |
| 7,278,995 B2 | 10/2007 | Nichols et al. |
| 7,282,065 B2 | 10/2007 | Kirschman |
| 7,291,150 B2 | 11/2007 | Graf et al. |
| 7,291,153 B2 | 11/2007 | Glascott |
| 7,294,129 B2 | 11/2007 | Hawkins et al. |
| 7,306,603 B2 | 12/2007 | Boehm, Jr. et al. |
| 7,329,258 B2 | 2/2008 | Studer et al. |
| 7,335,200 B2 | 2/2008 | Carli et al. |
| 7,354,453 B2 | 4/2008 | McAfee |
| 7,361,196 B2 | 4/2008 | Fallin et al. |
| 7,371,238 B2 | 5/2008 | Soboleski et al. |
| 7,377,921 B2 | 5/2008 | Studer et al. |
| 7,377,942 B2 | 5/2008 | Berry |
| 7,406,775 B2 | 8/2008 | Funk et al. |
| 7,445,635 B2 | 11/2008 | Fallin et al. |
| 7,465,306 B2 | 12/2008 | Pond, Jr. et al. |
| 7,470,279 B2 | 12/2008 | Jackson |
| 7,476,238 B2 | 1/2009 | Panjabi |
| 7,491,218 B2 | 2/2009 | Landry et al. |
| 7,493,019 B2 | 2/2009 | Moon et al. |
| 7,503,918 B2 | 3/2009 | Baccelli et al. |
| 7,527,638 B2 | 5/2009 | Anderson et al. |
| 7,547,318 B2 | 6/2009 | Birkmeyer et al. |
| 7,563,264 B2 | 7/2009 | Landry et al. |
| 7,588,575 B2 | 9/2009 | Colleran et al. |
| 7,588,588 B2 | 9/2009 | Spitler et al. |
| 7,591,839 B2 | 9/2009 | Biedermann et al. |
| 7,615,068 B2 | 11/2009 | Timm et al. |
| 7,618,442 B2 | 11/2009 | Spitler et al. |
| 7,635,379 B2 | 12/2009 | Callahan et al. |
| 7,662,172 B2 | 2/2010 | Warnick |
| 7,678,137 B2 | 3/2010 | Butler et al. |
| 7,699,875 B2 | 4/2010 | Timm |
| 7,713,287 B2 | 5/2010 | Timm et al. |
| 7,713,288 B2 | 5/2010 | Timm et al. |
| 7,935,134 B2 | 5/2011 | Reqlos et al. |
| 8,025,680 B2 | 9/2011 | Hayes et al. |
| 8,096,996 B2 | 1/2012 | Gutierrez et al. |
| 2001/0037111 A1 | 11/2001 | Dixon et al. |
| 2002/0026193 A1 | 2/2002 | Barker et al. |
| 2002/0032443 A1 | 3/2002 | Sherman et al. |
| 2002/0065557 A1 | 5/2002 | Goble et al. |
| 2002/0068975 A1 | 6/2002 | Teitelbaum et al. |
| 2002/0072800 A1 | 6/2002 | Goble et al. |
| 2002/0082599 A1 | 6/2002 | Crandall et al. |
| 2002/0082600 A1 | 6/2002 | Shaolian et al. |
| 2002/0091390 A1 | 7/2002 | Michelson |
| 2002/0095154 A1 | 7/2002 | Atkinson |
| 2002/0123806 A1 | 9/2002 | Reiley |
| 2002/0133154 A1 | 9/2002 | Saint Martin |
| 2002/0133155 A1 | 9/2002 | Ferree |
| 2002/0151895 A1 | 10/2002 | Soboleski et al. |
| 2002/0161368 A1 | 10/2002 | Foley et al. |
| 2002/0161370 A1 | 10/2002 | Frigg et al. |
| 2002/0173971 A1 | 11/2002 | Stirpe et al. |
| 2002/0183748 A1 | 12/2002 | Martin et al. |
| 2002/0198526 A1 | 12/2002 | Shaolian et al. |
| 2003/0004511 A1 | 1/2003 | Ferree |
| 2003/0004512 A1 | 1/2003 | Farris et al. |
| 2003/0004572 A1 | 1/2003 | Goble et al. |
| 2003/0018350 A1 | 1/2003 | Zucherman et al. |
| 2003/0023240 A1 | 1/2003 | Amrein et al. |
| 2003/0028250 A1 | 2/2003 | Reiley et al. |
| 2003/0032957 A1 | 2/2003 | McKinley |
| 2003/0032965 A1 | 2/2003 | Schneiderman |
| 2003/0040797 A1 | 2/2003 | Fallin et al. |
| 2003/0045878 A1 | 3/2003 | Petit et al. |
| 2003/0055426 A1 | 3/2003 | Carbone et al. |
| 2003/0055427 A1 | 3/2003 | Graf |
| 2003/0073996 A1 | 4/2003 | Doubler et al. |
| 2003/0073997 A1 | 4/2003 | Doubler et al. |
| 2003/0073998 A1 | 4/2003 | Pagliuca et al. |
| 2003/0125741 A1 | 7/2003 | Biedermann et al. |
| 2003/0149431 A1 | 8/2003 | Varieur |
| 2003/0153912 A1 | 8/2003 | Graf |
| 2003/0163133 A1 | 8/2003 | Altarac et al. |
| 2003/0171749 A1 | 9/2003 | Le Couedic et al. |
| 2003/0171750 A1 | 9/2003 | Chin |
| 2003/0199872 A1 | 10/2003 | Markworth et al. |
| 2003/0208202 A1 | 11/2003 | Falahee |
| 2003/0208203 A1 | 11/2003 | Lim et al. |
| 2003/0216735 A1 | 11/2003 | Altarac et al. |
| 2003/0220643 A1 | 11/2003 | Ferree |
| 2003/0229347 A1 | 12/2003 | Sherman et al. |
| 2004/0002708 A1 | 1/2004 | Ritland |
| 2004/0006341 A1 | 1/2004 | Shaolian et al. |
| 2004/0006344 A1 | 1/2004 | Nguyen et al. |
| 2004/0006391 A1 | 1/2004 | Reiley |
| 2004/0039384 A1 | 2/2004 | Boehm |
| 2004/0049189 A1 | 3/2004 | Le Couedic et al. |
| 2004/0049281 A1 | 3/2004 | Reiley |
| 2004/0064140 A1 | 4/2004 | Taylor et al. |
| 2004/0080418 A1 | 4/2004 | Dahlborn et al. |
| 2004/0082954 A1 | 4/2004 | Teitelbaum et al. |
| 2004/0087947 A1 | 5/2004 | Lim et al. |
| 2004/0092931 A1 | 5/2004 | Taylor et al. |
| 2004/0097933 A1 | 5/2004 | Lourdel et al. |
| 2004/0116927 A1 | 6/2004 | Graf |
| 2004/0127989 A1 | 7/2004 | Dooris et al. |
| 2004/0133208 A1 | 7/2004 | Weikel et al. |
| 2004/0138662 A1 | 7/2004 | Landry et al. |
| 2004/0143265 A1 | 7/2004 | Landry |
| 2004/0143270 A1 | 7/2004 | Zucherman et al. |
| 2004/0147928 A1 | 7/2004 | Landry et al. |
| 2004/0147936 A1 | 7/2004 | Rosenberg et al. |
| 2004/0147937 A1 | 7/2004 | Dunbar et al. |
| 2004/0215190 A1 | 10/2004 | Nguyen et al. |
| 2004/0225289 A1 | 11/2004 | Biedermann et al. |
| 2004/0230201 A1 | 11/2004 | Yuan et al. |
| 2004/0230304 A1 | 11/2004 | Yuan et al. |
| 2004/0236328 A1 | 11/2004 | Paul et al. |
| 2004/0236329 A1 | 11/2004 | Panjabi |
| 2004/0243126 A1 | 12/2004 | Carbone et al. |
| 2004/0249378 A1 | 12/2004 | Saint Martin et al. |
| 2004/0249380 A1 | 12/2004 | Glascott |
| 2004/0267260 A1 | 12/2004 | Mack et al. |
| 2005/0010217 A1 | 1/2005 | Dalton |
| 2005/0010953 A1 | 1/2005 | Carney et al. |
| 2005/0010954 A1 | 1/2005 | Binder |
| 2005/0010956 A1 | 1/2005 | Moon et al. |
| 2005/0021031 A1 | 1/2005 | Foley et al. |
| 2005/0027361 A1 | 2/2005 | Reiley |
| 2005/0033295 A1 | 2/2005 | Wisnewski |
| 2005/0033434 A1 | 2/2005 | Berry |
| 2005/0033436 A1 | 2/2005 | Schlapfer et al. |
| 2005/0033439 A1 | 2/2005 | Gordon et al. |
| 2005/0038429 A1 | 2/2005 | Elsebaie |
| 2005/0038430 A1 | 2/2005 | McKinley |
| 2005/0038432 A1 | 2/2005 | Shaolian et al. |
| 2005/0038440 A1 | 2/2005 | Larson et al. |
| 2005/0043742 A1 | 2/2005 | Bruneau et al. |
| 2005/0043797 A1 | 2/2005 | Lee |
| 2005/0043799 A1 | 2/2005 | Reiley |
| 2005/0049588 A1 | 3/2005 | Jackson |
| 2005/0049589 A1 | 3/2005 | Jackson |
| 2005/0049705 A1 | 3/2005 | Hale et al. |
| 2005/0049708 A1 | 3/2005 | Atkinson et al. |
| 2005/0055031 A1 | 3/2005 | Lim |
| 2005/0055096 A1 | 3/2005 | Serhan et al. |
| 2005/0065515 A1 | 3/2005 | Jahng |
| 2005/0065516 A1 | 3/2005 | Jahng |
| 2005/0065517 A1 | 3/2005 | Chin |
| 2005/0070917 A1 | 3/2005 | Justis |
| 2005/0080418 A1 | 4/2005 | Simonson et al. |
| 2005/0080486 A1 | 4/2005 | Fallin et al. |
| 2005/0085813 A1 | 4/2005 | Spitler et al. |
| 2005/0085815 A1 | 4/2005 | Harms et al. |
| 2005/0101953 A1 | 5/2005 | Simonson |
| 2005/0101954 A1 | 5/2005 | Simonson |
| 2005/0101956 A1 | 5/2005 | Simonson |
| 2005/0113832 A1 | 5/2005 | Molz, IV et al. |
| 2005/0113927 A1 | 5/2005 | Malek |
| 2005/0119748 A1 | 6/2005 | Reiley et al. |
| 2005/0124991 A1 | 6/2005 | Jahng |

| | | | | | | |
|---|---|---|---|---|---|---|
| 2005/0125066 A1 | 6/2005 | McAfee | | 2006/0084976 A1 | 4/2006 | Borgstrom et al. |
| 2005/0131405 A1 | 6/2005 | Molz et al. | | 2006/0084982 A1 | 4/2006 | Kim |
| 2005/0131406 A1 | 6/2005 | Reiley et al. | | 2006/0084984 A1 | 4/2006 | Kim |
| 2005/0131407 A1 | 6/2005 | Sicvol et al. | | 2006/0084987 A1 | 4/2006 | Kim |
| 2005/0131408 A1 | 6/2005 | Sicvol et al. | | 2006/0084991 A1 | 4/2006 | Borgstrom et al. |
| 2005/0131409 A1 | 6/2005 | Chervitz et al. | | 2006/0085072 A1 | 4/2006 | Funk et al. |
| 2005/0131422 A1 | 6/2005 | Anderson et al. | | 2006/0106380 A1 | 5/2006 | Colleran |
| 2005/0131537 A1 | 6/2005 | Hoy et al. | | 2006/0106394 A1 | 5/2006 | Colleran |
| 2005/0131538 A1 | 6/2005 | Chervitz et al. | | 2006/0111713 A1 | 5/2006 | Jackson |
| 2005/0131545 A1 | 6/2005 | Chervitz et al. | | 2006/0142759 A1 | 6/2006 | Arnin et al. |
| 2005/0137602 A1 | 6/2005 | Assell et al. | | 2006/0142761 A1 | 6/2006 | Landry et al. |
| 2005/0143737 A1 | 6/2005 | Pafford et al. | | 2006/0149238 A1 | 7/2006 | Sherman et al. |
| 2005/0143823 A1 | 6/2005 | Boyd et al. | | 2006/0149239 A1 | 7/2006 | Winslow et al. |
| 2005/0149020 A1 | 7/2005 | Jahng | | 2006/0149254 A1 | 7/2006 | Lauryssen et al. |
| 2005/0149036 A1 | 7/2005 | Varieur et al. | | 2006/0149272 A1 | 7/2006 | Winslow et al. |
| 2005/0149053 A1 | 7/2005 | Varieur et al. | | 2006/0149289 A1 | 7/2006 | Winslow et al. |
| 2005/0154389 A1 | 7/2005 | Selover et al. | | 2006/0149373 A1 | 7/2006 | Winslow et al. |
| 2005/0154390 A1 | 7/2005 | Biedermann et al. | | 2006/0149374 A1 | 7/2006 | Winslow et al. |
| 2005/0154461 A1 | 7/2005 | Humphreys et al. | | 2006/0149375 A1 | 7/2006 | Yuan et al. |
| 2005/0154464 A1 | 7/2005 | Humphreys et al. | | 2006/0149383 A1 | 7/2006 | Arnin et al. |
| 2005/0154465 A1 | 7/2005 | Hodges et al. | | 2006/0173454 A1 | 8/2006 | Spitler et al. |
| 2005/0154466 A1 | 7/2005 | Humphreys et al. | | 2006/0189983 A1 | 8/2006 | Fallin et al. |
| 2005/0154467 A1 | 7/2005 | Peterman et al. | | 2006/0189984 A1 | 8/2006 | Fallin et al. |
| 2005/0165396 A1 | 7/2005 | Fortin et al. | | 2006/0190083 A1 | 8/2006 | Arnin et al. |
| 2005/0171543 A1 | 8/2005 | Timm et al. | | 2006/0195086 A1 | 8/2006 | Sybert |
| 2005/0171608 A1 | 8/2005 | Peterman et al. | | 2006/0200137 A1 | 9/2006 | Soboleski et al. |
| 2005/0171609 A1 | 8/2005 | Humphreys et al. | | 2006/0217718 A1 | 9/2006 | Chervitz et al. |
| 2005/0171610 A1 | 8/2005 | Humphreys et al. | | 2006/0217719 A1 | 9/2006 | Albert et al. |
| 2005/0177156 A1 | 8/2005 | Timm et al. | | 2006/0229616 A1 | 10/2006 | Albert et al. |
| 2005/0177157 A1 | 8/2005 | Jahng | | 2006/0235388 A1 | 10/2006 | Justis et al. |
| 2005/0177164 A1 | 8/2005 | Walters et al. | | 2006/0235393 A1 | 10/2006 | Bono et al. |
| 2005/0177166 A1 | 8/2005 | Timm et al. | | 2006/0235414 A1 | 10/2006 | Lim et al. |
| 2005/0177240 A1 | 8/2005 | Blain | | 2006/0241593 A1 | 10/2006 | Sherman et al. |
| 2005/0182400 A1 | 8/2005 | White | | 2006/0241595 A1 | 10/2006 | Molz, IV et al. |
| 2005/0182401 A1 | 8/2005 | Timm et al. | | 2006/0241597 A1 | 10/2006 | Mitchell et al. |
| 2005/0182409 A1 | 8/2005 | Callahan et al. | | 2006/0241599 A1 | 10/2006 | Konieczynski et al. |
| 2005/0187548 A1 | 8/2005 | Butler | | 2006/0241642 A1 | 10/2006 | Arnin et al. |
| 2005/0192570 A1 | 9/2005 | Jackson | | 2006/0241758 A1 | 10/2006 | Peterman et al. |
| 2005/0192574 A1 | 9/2005 | Blain | | 2006/0241759 A1 | 10/2006 | Trieu |
| 2005/0192587 A1 | 9/2005 | Lim | | 2006/0241768 A1 | 10/2006 | Trieu |
| 2005/0197700 A1 | 9/2005 | Boehm et al. | | 2006/0241769 A1 | 10/2006 | Gordon et al. |
| 2005/0197705 A1 | 9/2005 | Arnin et al. | | 2006/0247623 A1 | 11/2006 | Anderson et al. |
| 2005/0203511 A1 | 9/2005 | Wilson-MacDonald et al. | | 2006/0247628 A1 | 11/2006 | Rawlins et al. |
| 2005/0203513 A1 | 9/2005 | Jahng et al. | | 2006/0247630 A1 | 11/2006 | Ion et al. |
| 2005/0203514 A1 | 9/2005 | Jahng et al. | | 2006/0247632 A1 | 11/2006 | Winslow et al. |
| 2005/0203517 A1 | 9/2005 | Jahng et al. | | 2006/0247633 A1 | 11/2006 | Winslow et al. |
| 2005/0209593 A1 | 9/2005 | Kolb | | 2006/0247637 A1 | 11/2006 | Colleran et al. |
| 2005/0209694 A1 | 9/2005 | Loeb | | 2006/0247649 A1 | 11/2006 | Rezach et al. |
| 2005/0215999 A1* | 9/2005 | Birkmeyer et al. ............. 606/61 | | 2006/0247650 A1 | 11/2006 | Yerby et al. |
| 2005/0216000 A1 | 9/2005 | Colleran et al. | | 2006/0247658 A1 | 11/2006 | Pond, Jr. et al. |
| 2005/0222569 A1 | 10/2005 | Panjabi | | 2006/0247769 A1 | 11/2006 | Molz et al. |
| 2005/0228378 A1 | 10/2005 | Kalfas et al. | | 2006/0247773 A1 | 11/2006 | Stamp |
| 2005/0228381 A1 | 10/2005 | Kirschman | | 2006/0260483 A1 | 11/2006 | Hartmann et al. |
| 2005/0234551 A1 | 10/2005 | Fallin et al. | | 2006/0264934 A1 | 11/2006 | Fallin |
| 2005/0235508 A1 | 10/2005 | Augostino et al. | | 2006/0264962 A1 | 11/2006 | Chin et al. |
| 2005/0240264 A1 | 10/2005 | Tokish et al. | | 2006/0265069 A1 | 11/2006 | Goble et al. |
| 2005/0240265 A1 | 10/2005 | Kuiper et al. | | 2006/0271198 A1 | 11/2006 | McAfee |
| 2005/0245928 A1 | 11/2005 | Colleran et al. | | 2006/0276798 A1 | 12/2006 | Lim |
| 2005/0245930 A1 | 11/2005 | Timm et al. | | 2006/0276801 A1 | 12/2006 | Yerby et al. |
| 2005/0249697 A1* | 11/2005 | Uhrich et al. ............. 424/78.37 | | 2006/0276897 A1 | 12/2006 | Winslow et al. |
| 2005/0261682 A1 | 11/2005 | Ferree | | 2006/0282075 A1 | 12/2006 | Labrom et al. |
| 2005/0261768 A1 | 11/2005 | Trieu | | 2006/0282077 A1 | 12/2006 | Labrom et al. |
| 2005/0273167 A1 | 12/2005 | Triplett et al. | | 2006/0282078 A1 | 12/2006 | Labrom et al. |
| 2005/0277921 A1 | 12/2005 | Eisermann et al. | | 2006/0282079 A1 | 12/2006 | Labrom et al. |
| 2005/0277922 A1 | 12/2005 | Trieu et al. | | 2006/0282080 A1 | 12/2006 | Albert et al. |
| 2005/0288670 A1 | 12/2005 | Panjabi et al. | | 2006/0293657 A1 | 12/2006 | Hartmann |
| 2006/0004449 A1 | 1/2006 | Goble et al. | | 2006/0293690 A1 | 12/2006 | Abdelgany |
| 2006/0004451 A1 | 1/2006 | Goble et al. | | 2006/0293692 A1 | 12/2006 | Whipple et al. |
| 2006/0015100 A1 | 1/2006 | Panjabi et al. | | 2007/0005062 A1 | 1/2007 | Lange et al. |
| 2006/0025769 A1 | 2/2006 | Dick et al. | | 2007/0005063 A1 | 1/2007 | Bruneau et al. |
| 2006/0036240 A1 | 2/2006 | Colleran et al. | | 2007/0016191 A1 | 1/2007 | Culbert et al. |
| 2006/0036244 A1 | 2/2006 | Spitler et al. | | 2007/0016193 A1 | 1/2007 | Ritland |
| 2006/0036255 A1 | 2/2006 | Pond, Jr. et al. | | 2007/0016195 A1 | 1/2007 | Winslow et al. |
| 2006/0036260 A1 | 2/2006 | Runco et al. | | 2007/0016196 A1 | 1/2007 | Winslow et al. |
| 2006/0052785 A1 | 3/2006 | Augostino et al. | | 2007/0016218 A1 | 1/2007 | Winslow et al. |
| 2006/0058791 A1 | 3/2006 | Broman et al. | | 2007/0016296 A1 | 1/2007 | Triplett et al. |
| 2006/0069391 A1 | 3/2006 | Jackson | | 2007/0043358 A1 | 2/2007 | Molz, IV et al. |
| 2006/0079894 A1 | 4/2006 | Colleran et al. | | 2007/0043359 A1 | 2/2007 | Altarac et al. |
| 2006/0079909 A1 | 4/2006 | Runco et al. | | 2007/0049931 A1 | 3/2007 | Justis et al. |

| | | | |
|---|---|---|---|
| 2007/0055242 A1 | 3/2007 | Bailly | |
| 2007/0055257 A1 | 3/2007 | Vaccaro et al. | |
| 2007/0073289 A1 | 3/2007 | Kwak et al. | |
| 2007/0073396 A1 | 3/2007 | Arnin | |
| 2007/0083264 A1 | 4/2007 | Arnin et al. | |
| 2007/0090238 A1 | 4/2007 | Justis | |
| 2007/0093816 A1 | 4/2007 | Arnin et al. | |
| 2007/0100341 A1 | 5/2007 | Reglos et al. | |
| 2007/0118120 A1 | 5/2007 | Farris et al. | |
| 2007/0118132 A1 | 5/2007 | Culbert et al. | |
| 2007/0123861 A1 | 5/2007 | Dewey et al. | |
| 2007/0123863 A1 | 5/2007 | Winslow et al. | |
| 2007/0123989 A1 | 5/2007 | Gfeller et al. | |
| 2007/0135814 A1 | 6/2007 | Farris | |
| 2007/0161998 A1 | 7/2007 | Whipple | |
| 2007/0167949 A1 | 7/2007 | Altarac et al. | |
| 2007/0173828 A1 | 7/2007 | Firkins et al. | |
| 2007/0213722 A1 | 9/2007 | Jones et al. | |
| 2007/0219556 A1 | 9/2007 | Altarac et al. | |
| 2007/0225712 A1 | 9/2007 | Altarac et al. | |
| 2007/0225713 A1 | 9/2007 | Altarac et al. | |
| 2007/0239159 A1 | 10/2007 | Altarac et al. | |
| 2007/0255284 A1 | 11/2007 | Miller et al. | |
| 2007/0270811 A1 | 11/2007 | Dewey | |
| 2007/0270867 A1 | 11/2007 | Miller et al. | |
| 2007/0270868 A1 | 11/2007 | Dewey | |
| 2007/0270869 A1 | 11/2007 | Young et al. | |
| 2007/0276379 A1 | 11/2007 | Miller et al. | |
| 2008/0009864 A1 | 1/2008 | Forton et al. | |
| 2008/0015601 A1 | 1/2008 | Castro et al. | |
| 2008/0039839 A1 | 2/2008 | Songer et al. | |
| 2008/0045957 A1 | 2/2008 | Landry et al. | |
| 2008/0051787 A1 | 2/2008 | Reminton et al. | |
| 2008/0065072 A1 | 3/2008 | Spitler et al. | |
| 2008/0077136 A1 | 3/2008 | Triplett et al. | |
| 2008/0077139 A1 | 3/2008 | Landry et al. | |
| 2008/0077155 A1 | 3/2008 | Diederich et al. | |
| 2008/0097441 A1 | 4/2008 | Hayes et al. | |
| 2008/0177275 A1 | 7/2008 | Wing et al. | |
| 2008/0183215 A1 | 7/2008 | Altarac et al. | |
| 2008/0221626 A1 | 9/2008 | Butiers et al. | |
| 2008/0228233 A1 | 9/2008 | Hoffman et al. | |
| 2008/0234678 A1 | 9/2008 | Gutierrez et al. | |
| 2008/0234765 A1 | 9/2008 | Frasier et al. | |
| 2008/0243126 A1 | 10/2008 | Gutierrez et al. | |
| 2008/0249372 A1 | 10/2008 | Reglos et al. | |
| 2008/0249628 A1 | 10/2008 | Altarac et al. | |
| 2008/0262554 A1 | 10/2008 | Hayes et al. | |
| 2008/0306488 A1 | 12/2008 | Altarac et al. | |
| 2008/0306489 A1 | 12/2008 | Altarac et al. | |
| 2008/0306557 A1 | 12/2008 | Altarac et al. | |
| 2008/0312692 A1 | 12/2008 | Brennan et al. | |
| 2009/0030465 A1 | 1/2009 | Altarac et al. | |
| 2009/0036929 A1 | 2/2009 | Reglos et al. | |
| 2009/0082775 A1 | 3/2009 | Altarac et al. | |
| 2009/0125032 A1 | 5/2009 | Gutierrez et al. | |
| 2009/0125047 A1 | 5/2009 | Reglos et al. | |
| 2009/0138056 A1 | 5/2009 | Anderson et al. | |
| 2009/0177196 A1 | 7/2009 | Zlock et al. | |
| 2009/0204155 A1 | 8/2009 | Aschmann | |
| 2009/0216237 A1 | 8/2009 | Frezal et al. | |
| 2009/0228045 A1 | 9/2009 | Hayes et al. | |
| 2009/0228053 A1 | 9/2009 | Kolb et al. | |
| 2009/0228054 A1 | 9/2009 | Hoffman et al. | |
| 2009/0228055 A1 | 9/2009 | Jackson | |
| 2010/0036423 A1 | 2/2010 | Hayes et al. | |
| 2010/0174317 A1 | 7/2010 | Timm et al. | |
| 2010/0222819 A1 | 9/2010 | Timm et al. | |
| 2011/0144701 A1 | 6/2011 | Altarac et al. | |
| 2011/0166610 A1 | 7/2011 | Altarac et al. | |

FOREIGN PATENT DOCUMENTS

| | | | |
|---|---|---|---|
| EP | 0951246 | | 10/1999 |
| EP | 0986339 | | 3/2000 |
| EP | 1056408 | | 12/2000 |
| EP | 1138268 | | 10/2001 |
| EP | 1145602 | | 10/2001 |
| EP | 1303225 | | 4/2003 |
| EP | 1399078 | | 3/2004 |
| EP | 1415602 | | 7/2005 |
| EP | 1415603 | | 7/2005 |
| EP | 1128773 | | 6/2006 |
| EP | 1459690 | | 6/2006 |
| EP | 986338 | | 7/2006 |
| EP | 1810624 | | 7/2007 |
| FR | 2728454 | | 6/1996 |
| WO | WO-9116018 | | 10/1991 |
| WO | WO-9426192 | | 11/1994 |
| WO | 9531158 | | 11/1995 |
| WO | WO-9600049 | | 1/1996 |
| WO | 9822033 | | 5/1998 |
| WO | WO-9848717 | | 11/1998 |
| WO | WO-9855038 | | 12/1998 |
| WO | WO-0062684 | | 10/2000 |
| WO | WO-0130248 | | 5/2001 |
| WO | WO-0141681 | | 6/2001 |
| WO | WO-0238060 | | 5/2002 |
| WO | WO-02065954 | | 8/2002 |
| WO | WO-02067793 | | 9/2002 |
| WO | WO-02102259 | | 12/2002 |
| WO | WO-03047442 | | 6/2003 |
| WO | WO-03075805 | | 9/2003 |
| WO | WO-03094699 | | 11/2003 |
| WO | WO-03101350 | | 12/2003 |
| WO | WO-2004008949 | | 1/2004 |
| WO | WO-2004047617 | | 6/2004 |
| WO | 2004078221 | | 9/2004 |
| WO | 2004103227 | | 12/2004 |
| WO | 2004103228 | | 12/2004 |
| WO | 2005009301 | | 2/2005 |
| WO | 2005013864 | | 2/2005 |
| WO | 2005018471 | | 3/2005 |
| WO | 2005030087 | | 4/2005 |
| WO | WO-2005030029 | | 4/2005 |
| WO | WO-2005030031 | | 4/2005 |
| WO | WO-2005030066 | | 4/2005 |
| WO | WO-2005030067 | | 4/2005 |
| WO | WO-2005041799 | | 5/2005 |
| WO | WO-2005044152 | | 5/2005 |
| WO | WO-2005046515 | | 5/2005 |
| WO | WO-2005053572 | | 6/2005 |
| WO | WO-2005055874 | | 6/2005 |
| WO | 2005060879 | | 7/2005 |
| WO | WO-2005067824 | | 7/2005 |
| WO | 2005076974 | | 8/2005 |
| WO | WO-2005070278 | | 8/2005 |
| WO | WO-2005070349 | | 8/2005 |
| WO | WO-2005070350 | | 8/2005 |
| WO | WO-2005070351 | | 8/2005 |
| WO | WO-2005070352 | | 8/2005 |
| WO | WO-2005070353 | | 8/2005 |
| WO | WO-2005070354 | | 8/2005 |
| WO | WO-2005077113 | | 8/2005 |
| WO | WO-2005079426 | | 9/2005 |
| WO | WO-2005079672 | | 9/2005 |
| WO | WO-2005079711 | | 9/2005 |
| WO | WO-2005084590 | | 9/2005 |
| WO | WO-2005087121 | | 9/2005 |
| WO | 2005096974 | | 10/2005 |
| WO | WO-2005092223 | | 10/2005 |
| WO | WO-2005094704 | | 10/2005 |
| WO | 2005104998 | | 11/2005 |
| WO | 2005117765 | | 12/2005 |
| WO | 2005120401 | | 12/2005 |
| WO | WO-2006016371 | | 2/2006 |
| WO | WO-2006017507 A2 | | 2/2006 |
| WO | 2006023683 | | 3/2006 |
| WO | 2006033659 | | 3/2006 |
| WO | 2006039260 | | 4/2006 |
| WO | WO-2006042188 | | 4/2006 |
| WO | WO-2006042189 | | 4/2006 |
| WO | 2006023671 | | 5/2006 |
| WO | WO-2006047363 | | 5/2006 |
| WO | 2006063083 | | 6/2006 |
| WO | 2006065774 | | 6/2006 |
| WO | 2006067790 | | 6/2006 |
| WO | WO-2006063107 | | 6/2006 |
| WO | 2006045091 | | 8/2006 |

| | | |
|---|---|---|
| WO | 2006055186 | 8/2006 |
| WO | 2006089237 | 8/2006 |
| WO | 2006096351 | 9/2006 |
| WO | 2006096381 | 9/2006 |
| WO | 2006101655 | 9/2006 |
| WO | 2006102268 | 9/2006 |
| WO | WO-2006102443 | 9/2006 |
| WO | 2006104999 | 10/2006 |
| WO | 2006109310 | 10/2006 |
| WO | 2006110796 | 10/2006 |
| WO | 2006113256 | 10/2006 |
| WO | WO-2006108067 A2 | 10/2006 |
| WO | 2006115954 | 11/2006 |
| WO | 2006116214 | 11/2006 |
| WO | 2006119151 | 11/2006 |
| WO | 2006119236 | 11/2006 |
| WO | 2006119237 | 11/2006 |
| WO | 2006119241 | 11/2006 |
| WO | WO-2006125142 | 11/2006 |
| WO | 2006135511 | 12/2006 |
| WO | 2007014119 | 2/2007 |
| WO | WO-2007021588 A1 | 2/2007 |
| WO | 2007031998 | 3/2007 |
| WO | 2007034472 | 3/2007 |
| WO | 2007037801 | 4/2007 |
| WO | 2007038261 | 4/2007 |
| WO | 2007043044 | 4/2007 |
| WO | 2007102846 | 9/2007 |
| WO | 2007117366 | 10/2007 |
| WO | 2007121061 | 10/2007 |
| WO | 2007127608 | 11/2007 |
| WO | 2007127682 | 11/2007 |
| WO | 2007136612 | 11/2007 |
| WO | 2008069835 | 6/2008 |
| WO | 2008115549 | 9/2008 |
| WO | 2008121421 | 10/2008 |
| WO | 2008124186 | 10/2008 |
| WO | 2008140756 | 11/2008 |
| WO | 2008153747 | 12/2008 |
| WO | 2009042489 | 4/2009 |
| WO | 2009049206 | 4/2009 |
| WO | 2009076239 | 6/2009 |
| WO | 2009091960 | 7/2009 |
| WO | 2009100190 | 8/2009 |
| WO | 2008121343 | 10/2009 |
| WO | 2010019791 | 2/2010 |
| WO | 2011017712 | 2/2011 |
| WO | 2011028575 | 3/2011 |

OTHER PUBLICATIONS

International Search Report and Written Opinion for application No. PCT/US06/28586, Mail Date Jul. 27, 2007, 14 pages.
International Search Report and Written Opinion for application No. PCT/US07/04726, Mail Date Jul. 8, 2008, 7 pages.
International Search Report and Written Opinion for application No. PCT/US05/38021, Mail Date Apr. 10, 2006, 7 pages.
International Search Report and Written Opinion for application No. PCT/US07/11573, Mail Date Jul. 23, 2008, 8 pages.
Co-pending Appl. No. PCT/US2006/047824.
Co-pending U.S. Appl. No. 11/586,849.
U.S. Appl. No. 60/701,660.
Final Office Action for U.S. Appl. No. 10/970,366, Mail Date: Oct. 5, 2009, 8 pages.
Non-Final Office Action for U.S. Appl. No. 10/970,366, Mail Date: Nov. 25, 2008, 7 pages.
Non-Final Office Action for U.S. Appl. No. 11/006,495, Mail Date: Jun. 30, 2008, 9 pages.
Final Office Action for U.S. Appl. No. 11/006,495, Mail Date: Mar. 20, 2009, 8 pages.
Non-Final Office Action for U.S. Appl. No. 11/006,495, Mail Date: Dec. 29, 2009, 9 pages.
Non-Final Office Action for U.S. Appl. No. 11/033,452, Mail Date: Dec. 11, 2008, 6 pages.
Non-Final Office Action for U.S. Appl. No. 11/033,452, Mail Date: Oct. 13, 2009, 7 pages.
Non-Final Office Action for U.S. Appl. No. 11/436,407, Mail Date: Jun. 12, 2009, 13 pages.
Non-Final Office Action for U.S. Appl. No. 11/427,738, Mail Date: Dec. 29, 2009, 8 pages.
USPTO Final Office Action for U.S. Appl. No. 11/586,849, mailed Jan. 6, 2012.
USPTO Final Office Action for U.S. Appl. No. 12/355,093, mailed Dec. 13, 2011.
USPTO Non-Final Office Action for U.S. Appl. No. 12/270,505, mailed Feb. 16, 2012.
USPTO Advisory Action for U.S. Appl. No. 11/726,093, mailed Aug. 30, 2011.
USPTO Notice of Allowance for U.S. Appl. No. 12/077,462, mailed Sep. 28, 2011.
USPTO Final Office Action for U.S. Appl. No. 11/362,366 mailed Oct. 27, 2011.
USPTO Non-Final Office Action for U.S. Appl. No. 12/329,423, mailed Nov. 30, 2011.
First Examiner's Report for AU App. No. 2006272755 mailed May 31, 2011. (pp. 1-3).
Second Exmainer's Report for AU App. No. 2005295209 mailed Jun. 1, 2011. (pp. 1-3).
International Preliminary Report on Patentability and Written Opinion for PCT/US2008/079580, mailed Apr. 29, 2009. (pp. 1-6).
International Preliminary Report on Patentability and Written Opinion for PCT/US2009/053740, Feb. 21, 2011. (6 pages).
International Search Report and Written Opinion for PCT/US2008/085748, mailed Jun. 22, 2009. (pp. 1-10).
International Search Report and Written Opinion for PCT/US2009/031225, mailed Aug. 31, 2009. (15 pages).
International Search Report for PCT/US2010/44930, mailed Apr. 1, 2011. (pp. 1-4).
USPTO Communication for U.S. Appl. No. 11/586,849, mailed Jul. 8, 2011.
USPTO Communication for U.S. Appl. No. 11/726,093, mailed Nov. 5, 2010.
USPTO Communication for U.S. Appl. No. 11/726,093, mailed May 12, 2011.
USPTO Communication for U.S. Appl. No. 12/355,093, mailed Jun. 27, 2011.
USPTO Communication for U.S. Appl. No. 12/077,462, mailed Mar. 18, 2011.

* cited by examiner

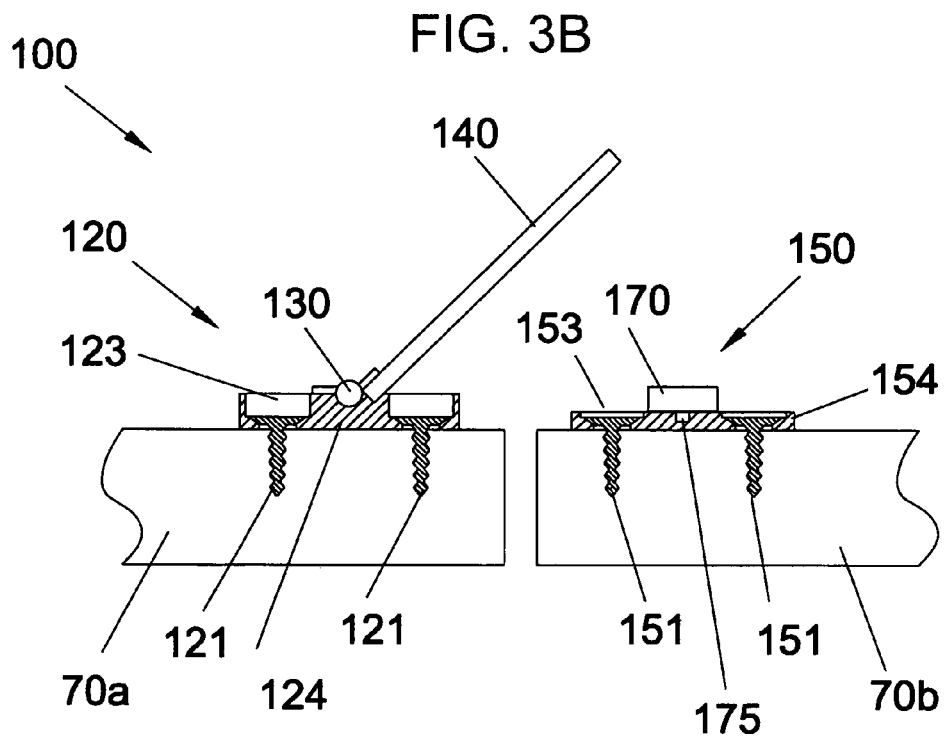
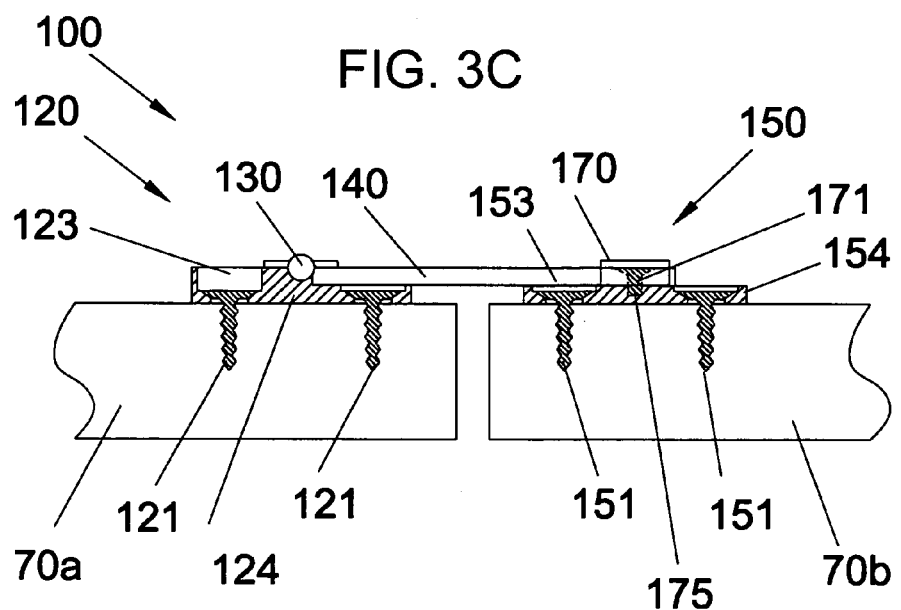

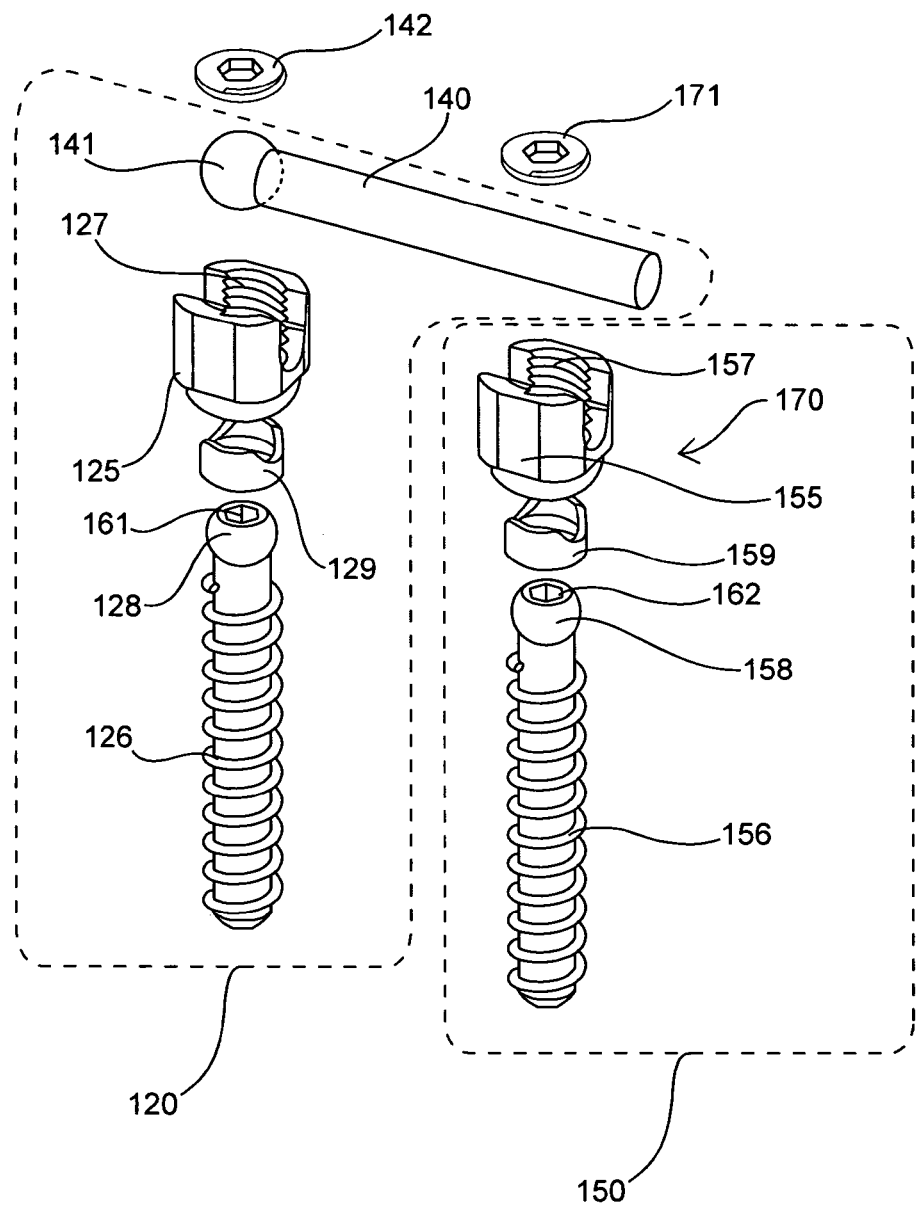

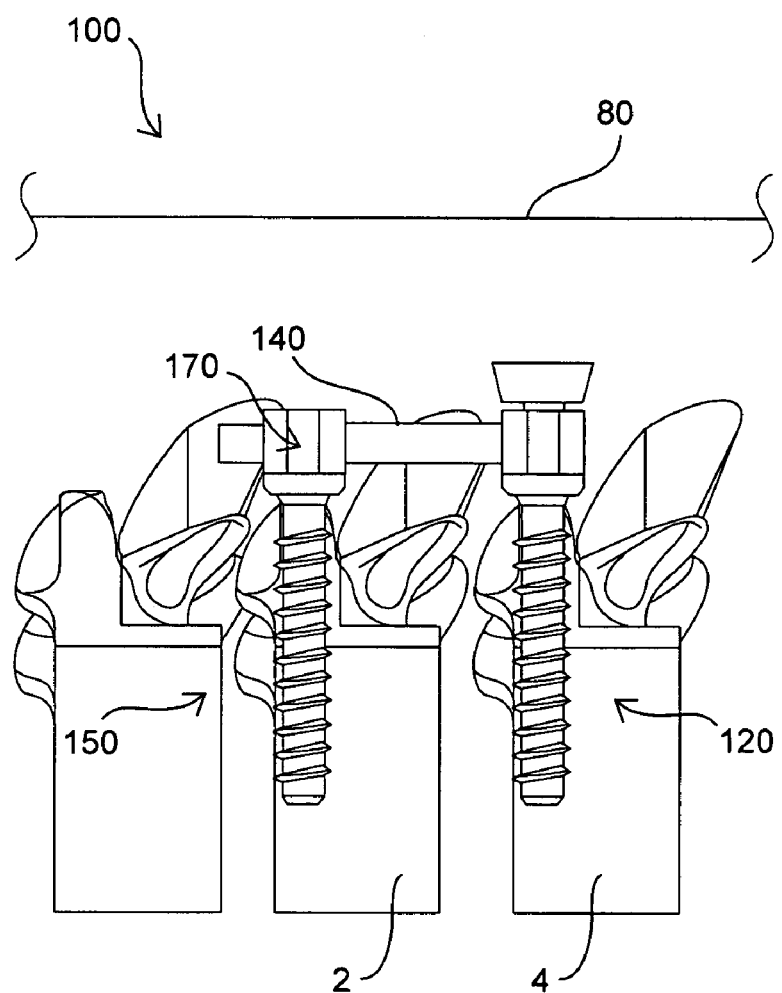

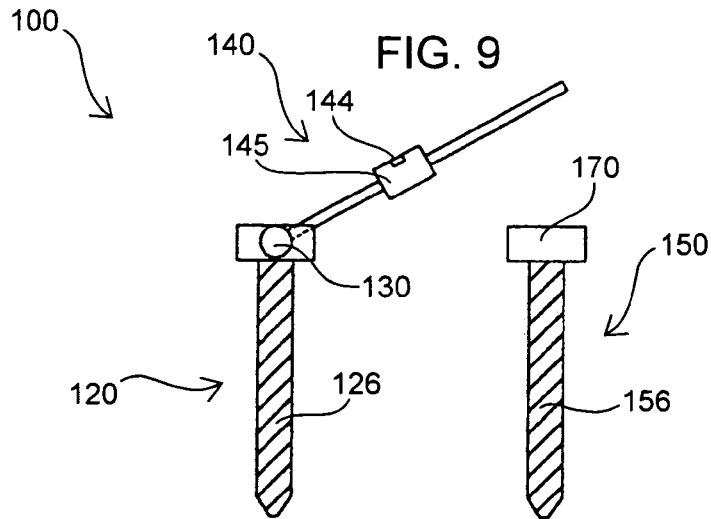
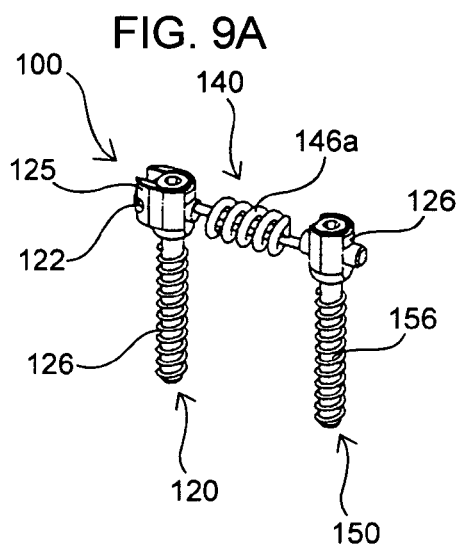
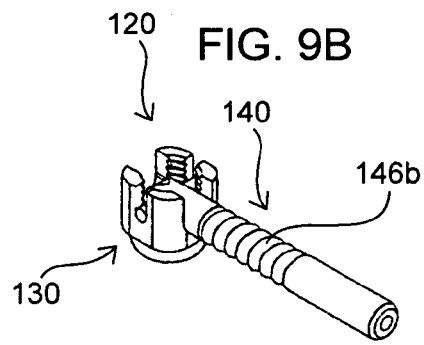
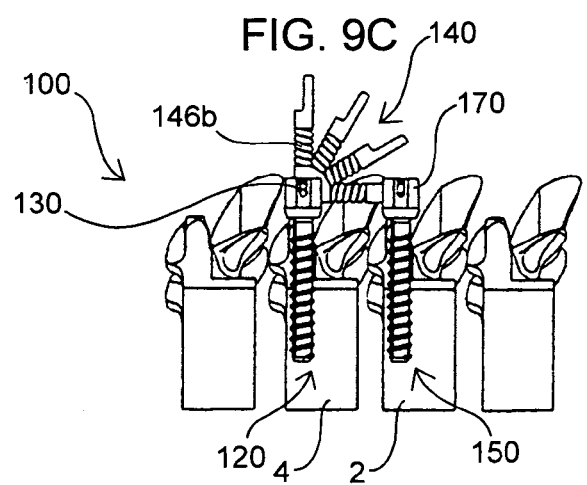

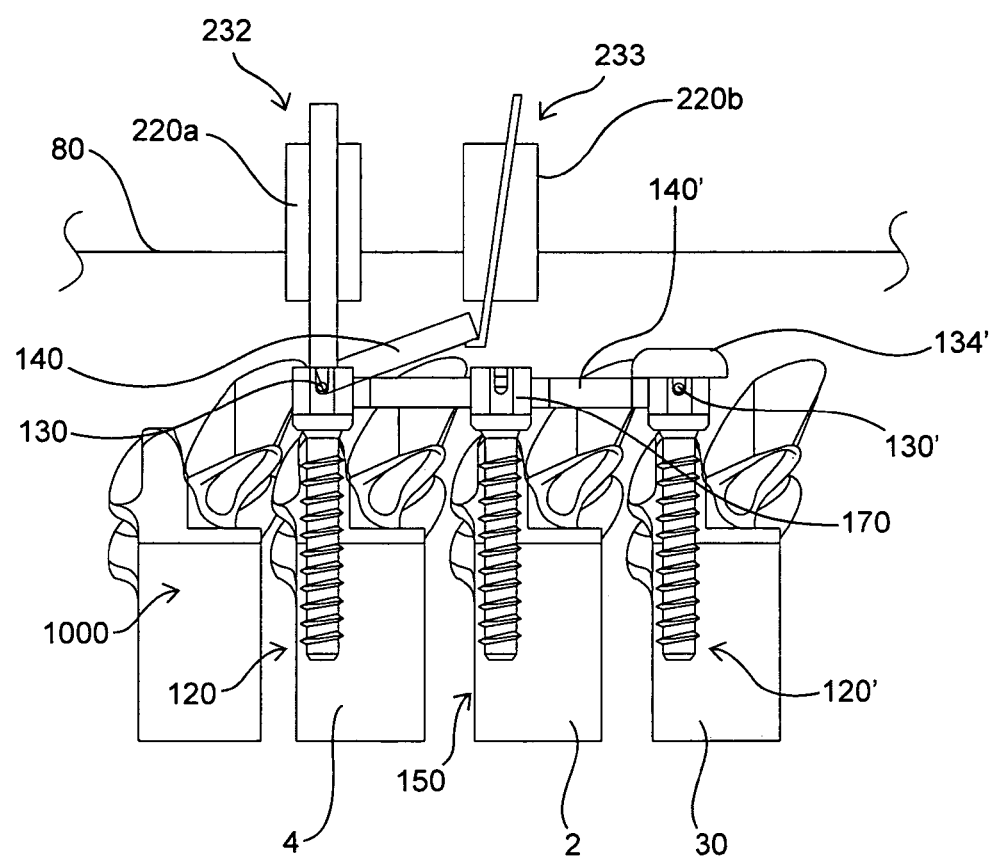

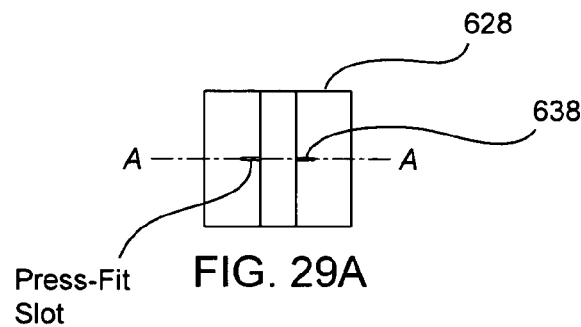
Press-Fit Slot    FIG. 29A
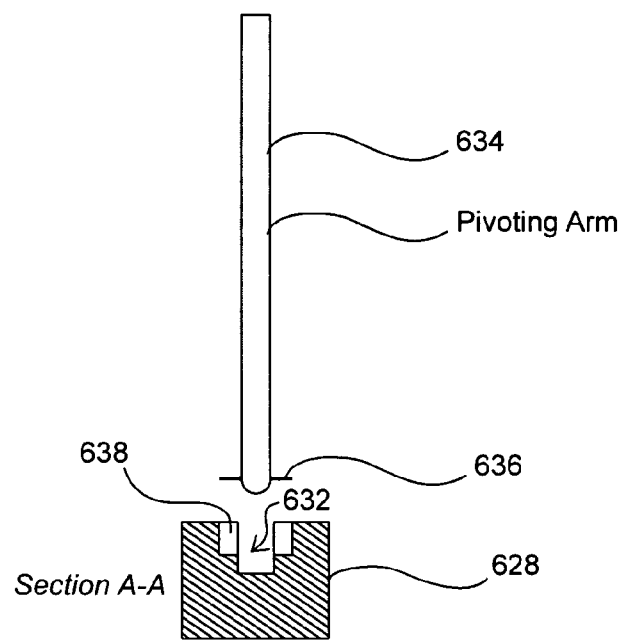
FIG. 29

SYSTEMS AND METHODS FOR STABILIZATION OF BONE STRUCTURES

FIELD OF THE INVENTION

The present invention generally relates to surgical instruments and methods for using these instruments. More particularly, but not exclusively, minimally invasive methods of stabilizing one or more bone structures is disclosed.

BACKGROUND OF THE INVENTION

Systems, methods and devices for stabilizing one or more bone structures of a patient have been available for many years. Securing a metal plate is used to stabilize a broken bone, maintaining the bone in a desired position during the healing process. These implanted plates are either removed when sufficient healing has occurred or left in place for a long-term or indefinite, chronic period. A procedure involving the placement of one or more elongated rods extending between two bone structures or between two components of a single bone structure is often used as a stabilization technique. These rods are placed alongside the bone structure or structures and attached to bone with specialized screws. These procedures require large incisions and also significant tissue manipulation to adequately expose the areas intended for the attachment. The procedures are associated with long recovery times and increased potential for adverse events, such as infection, usually associated with muscle and other tissue trauma and scarring.

Currently available minimally invasive techniques and products are limited. These procedures are difficult to perform, especially in spinal applications in which the attachment points are deeper in tissue, and damage to neighboring tissue must be avoided. Many of the currently available less invasive products remain somewhat invasive due to component configurations, and required manipulations to be performed during the attachment.

In reference specifically to treatment of the spine, FIG. 1A illustrates a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, posterior arch 16 and spinous process 18. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joints 10a and 10b and the spinous process 18 are lamina 5a and 5b, respectively. Similarly, inferior vertebra 4 has superior facet joints 12a and 12b, superior pedicles 9a and 9b, transverse processes 11a and 11b, inferior facet joints 14a and 14b, lamina 15a and 15b, posterior arch 20, spinous process 22.

The superior vertebra with its inferior facets, the inferior vertebra with its superior facets, the intervertebral disc, and seven spinal ligaments (not shown) extending between the superior and inferior vertebrae together comprise a spinal motion segment or functional spine unit. Each spinal motion segment enables motion along three orthogonal axis, both in rotation and in translation. The various spinal motions are illustrated in FIGS. 2A-2C. In particular, FIG. 2A illustrates flexion and extension motions and axial loading, FIG. 2B illustrates lateral bending motion and FIG. 2C illustrated axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. It is one of the most common approaches to alleviating various types of spinal pain, particularly pain associated with one or more affected intervertebral discs. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments. Additionally, pseudarthrosis (resulting from an incomplete or ineffective fusion) may not provide the expected pain-relief for the patient. Also, the device(s) used for fusion, whether artificial or biological, may migrate out of the fusion site creating significant new problems for the patient.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to restore articulation between vertebral bodies so as to recreate the full range of motion normally allowed by the elastic properties of the natural disc. Unfortunately, the currently available artificial discs do not adequately address all of the mechanics of motion for the spinal column.

It has been found that the facet joints can also be a significant source of spinal disorders and debilitating pain. For example, a patient may suffer from arthritic facet joints, severe facet joint tropism, otherwise deformed facet joints, facet joint injuries, etc. These disorders lead to spinal stenosis, degenerative spondylolithesis, and/or isthmic spondylotlisthesis, pinching the nerves which extend between the affected vertebrae.

Current interventions for the treatment of facet joint disorders have not been found to provide completely successful results. Facetectomy (removal of the facet joints) may provide some pain relief; but as the facet joints help to support axial, torsional, and shear loads that act on the spinal column in addition to providing a sliding articulation and mechanism for load transmission, their removal inhibits natural spinal function. Laminectomy (removal of the lamina, including the spinal arch and the spinous process) may also provide pain relief associated with facet joint disorders; however, the spine is made less stable and subject to hypermobility. Problems with the facet joints can also complicate treatments associated with other portions of the spine. In fact, contraindications for disc replacement include arthritic facet joints, absent facet joints, severe facet joint tropism, or otherwise deformed facet joints due to the inability of the artificial disc (when used with compromised or missing facet joints) to properly restore the natural biomechanics of the spinal motion segment.

While various attempts have been made at facet joint replacement, they have been inadequate. This is due to the fact that prosthetic facet joints preserve existing bony structures and therefore do not address pathologies which affect facet joints themselves. Certain facet joint prostheses, such as those disclosed in U.S. Pat. No. 6,132,464, are intended to be supported on the lamina or the posterior arch. As the lamina is a very complex and highly variable anatomical structure, it is very difficult to design a prosthesis that provides reproducible positioning against the lamina to correctly locate the prosthetic facet joints. In addition, when facet joint replacement involves complete removal and replacement of the natural facet joint, as disclosed in U.S. Pat. No. 6,579,319, the prosthesis is unlikely to endure the loads and cycling experienced by the vertebra. Thus, the facet joint replacement may be subject to long-term displacement. Furthermore, when facet joint disorders are accompanied by disease or trauma to other structures of a vertebra (such as the lamina, spinous process, and/or transverse processes) facet joint replacement is insufficient to treat the problem(s).

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. Dynamic posterior stabilization systems typically fall into one of two general categories: (1) interspinous spacers and (2) posterior pedicle screw-based systems.

Examples of interspinous spacers are disclosed in U.S. Pat. Nos. Re. 36,211, 5,645,599, 6,695,842, 6,716,245 and 6,761,720. The spacers, which are made of either a hard or compliant material, are placed between adjacent spinous processes. Because the interspinous spacers involve attachment to the spinous processes, use of these types of systems is limited to applications where the spinous processes are uncompromised and healthy.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws which are positioned in the vertebral body through the pedicle. Certain types of these pedicle screw-based systems may be used to augment compromised facet joints, while others require removal of the spinous process and/or the facet joints for implantation. One such system, the Zimmer Spine Dynesys® employs a cord which is extended between the pedicle screws and a fairly rigid spacer which is passed over the cord and positioned between the screws. While this system is able to provide load sharing and restoration of disc height, because it is so rigid, it does not effective in preserving the natural motion of the spinal segment into which it is implanted. Other pedicle screw-based systems employ articulating joints between the pedicle screws.

There remains a need for minimally invasive methods and devices for bone stabilization procedures, including but not limited to spinal segment stabilization procedures such as dynamic spinal segment stabilization procedures. There is a need for procedures that are simple to perform and reliably achieve the desired safe and effective outcome. Goals of these new procedures and instruments include minimizing the size of the incision and reducing the amount of muscle dissection in order to shorten recovery times, improve procedure success rates and reduce the number of resultant adverse side effects.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 3A, 3B and 3C illustrate a side sectional view of a bone stabilization device, consistent with the present invention, placed between a first bone location and a second bone location and shown in various levels of rotation of a pivoting arm of the hinged assembly of the device.

FIG. 5 illustrates an exploded perspective view of a bone stabilization device consistent with the present invention.

FIGS. 6A through 6H illustrate multiple side sectional views of a method of placing a bone stabilization device in a minimally invasive percutaneous procedure, consistent with the present invention.

FIG. 9 illustrates a side schematic view of a hinged assembly consistent with the present invention wherein the pivoting arm includes a functional element along its length.

FIGS. 9A and 9B illustrate perspective views of hinged assemblies of the present invention in which a functional element includes a dynamic motion element, a tension-compression spring and a coiled spring respectively.

FIG. 9C illustrates a side sectional view of the bone stabilization device of the present invention with the hinged assembly of FIG. 9B shown in multiple stages of rotating its pivoting arm.

FIG. 16 illustrates a side sectional view of a method consistent with the present invention in which an already placed bone stabilization device is accessed for adjustment, removal or partial removal.

FIG. 29 and 29A show side and top views, respectively, of a frictional-fit engagement for a pivoting rod to attach to a seat of a bone anchor.

DETAILED DESCRIPTION

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1A:
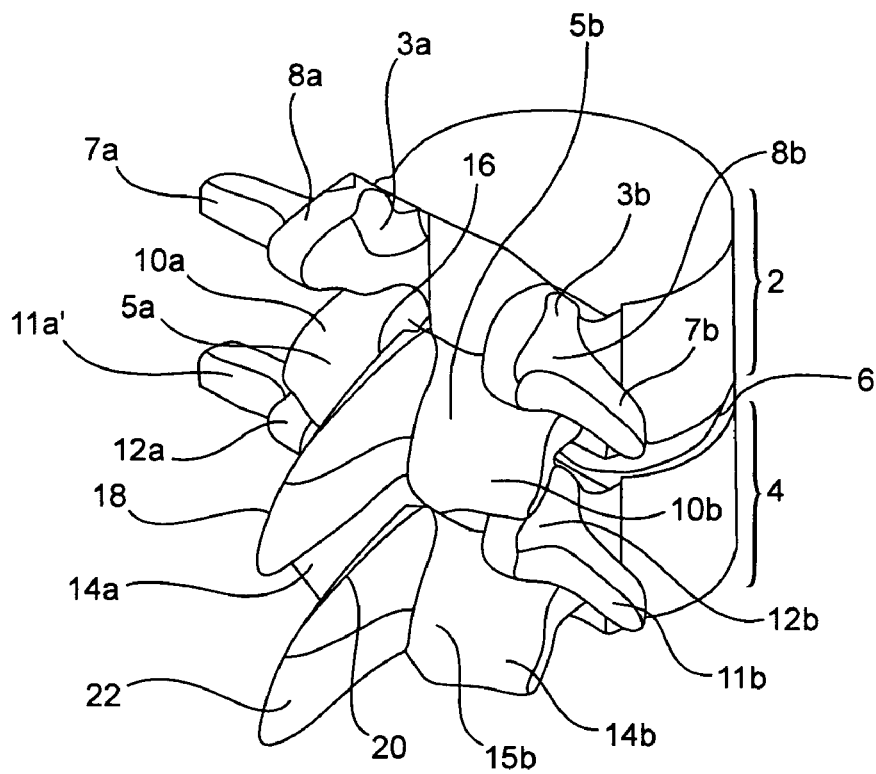
FIGS. 1A and 1B illustrate perspective views of a portion of the human spine having two vertebral segments, where the spinous process and the lamina of the superior vertebra have been resected in FIG. 1B.
Figure 1B:
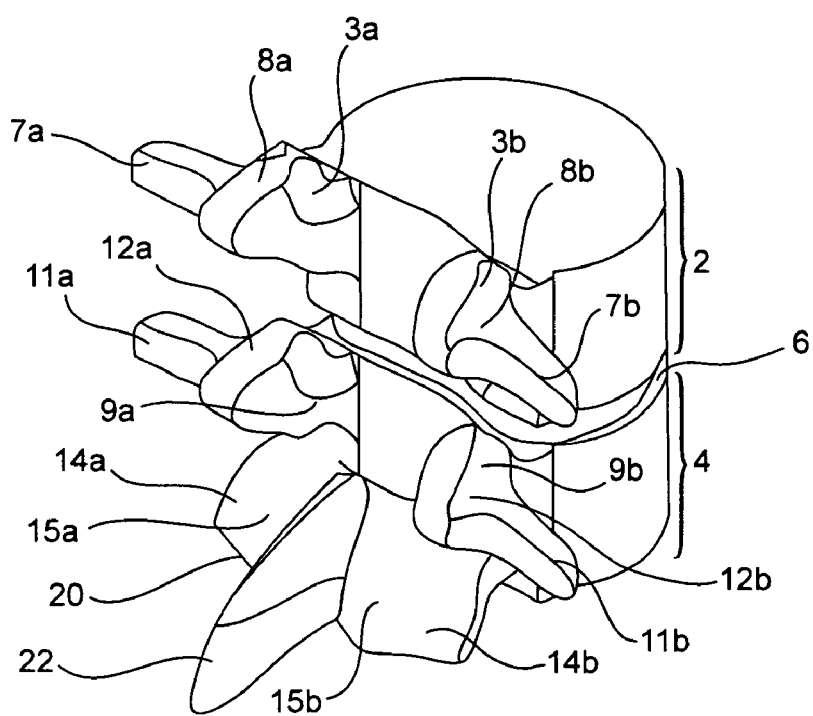
Figure 2A:
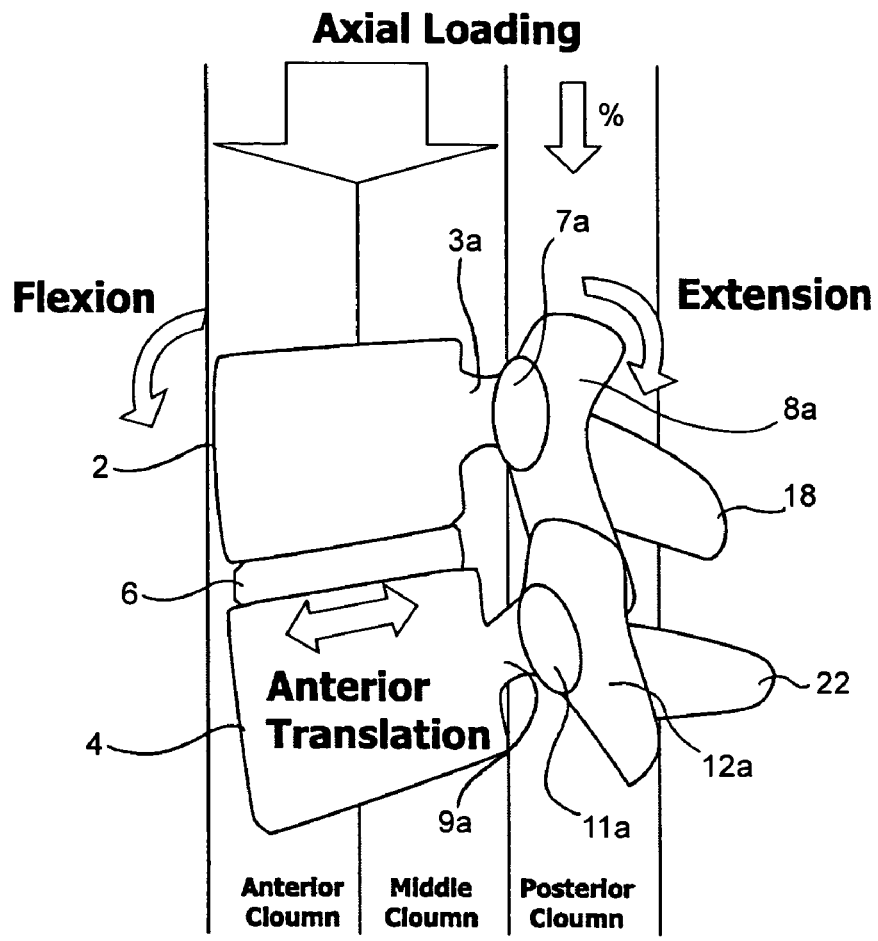
FIGS. 2A, 2B and 2C illustrate left side, dorsal and top views, respectively, of the spinal segments of FiG. IA under going various motions.
Figure 2B:
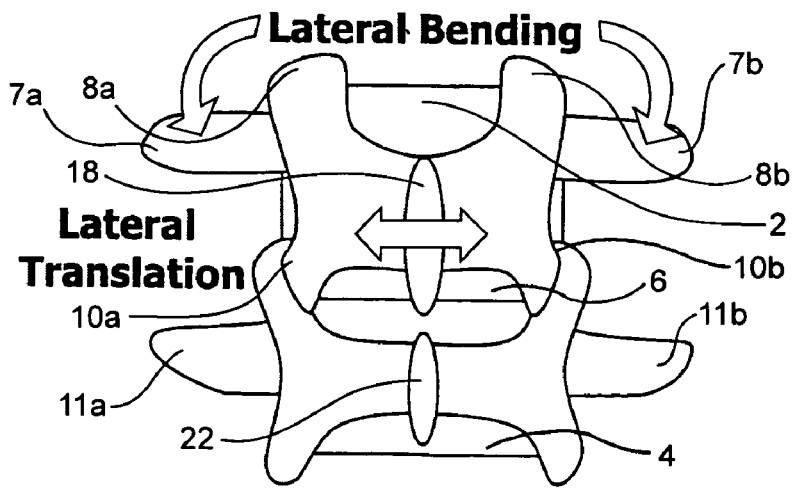
Figure 2C:
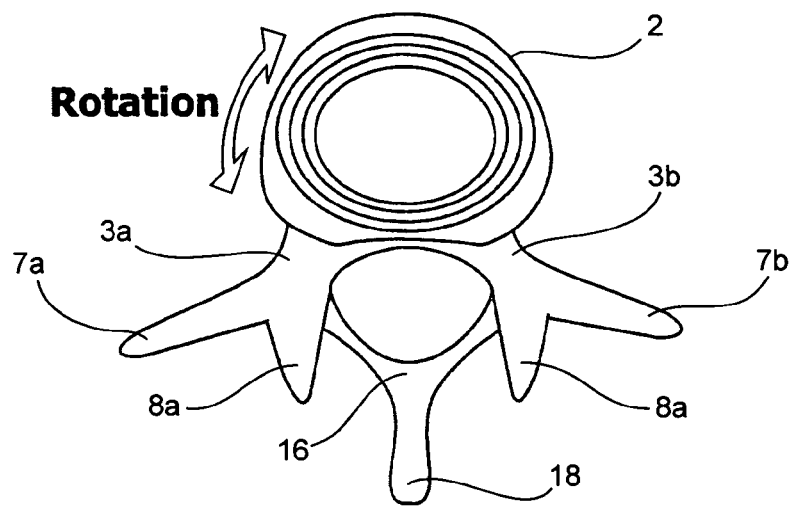

The present invention will now be described in greater detail by way of the following description of exemplary embodiments and variations of the systems and methods of the present invention. While more fully described in the context of the description of the subject methods of implanting the subject systems, it should be initially noted that in certain applications where the natural facet joints are compromised, as illustrated in FIG. 1B, inferior facets 10a and 10b, lamina 5a and 5b, posterior arch 16 and spinous process 18 of superior vertebra 2 of FIG. 1A may be resected for purposes of implantation of certain of the dynamic stabilization systems of the present invention. In other applications, where possible, the natural facet joints, lamina and/or spinous processes are spared and left intact for implantation of other dynamic stabilization systems of the present invention.

It should also be understood that the term "system", when referring to a system of the present invention, most typically refers to a set of components which includes multiple bone stabilization components such as a superior, cephalad or rostral (towards the head) component configured for implantation into a superior vertebra of a vertebral motion segment and an inferior or caudal (towards the feet) component configured for implantation into an inferior vertebra of a vertebral motion segment. A pair of such component sets may include one set of components configured for implantation into and stabilization of the left side of a vertebral segment and another set configured for the implantation into and stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween.

The superior and inferior components (and any medial components therebetween), when operatively implanted, may be engaged or interface with each other in a manner that enables the treated spinal motion segment to mimic the function and movement of a healthy segment, or may simply fuse the segments such as to eliminate pain and/or promote or enhance healing. The interconnecting or interface means include one or more structures or members that enables, limits and/or otherwise selectively controls spinal or other body motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result.

In certain embodiments, the multiple components, such as superior and inferior spinal components, are mechanically coupled to each other by one or more interconnecting or interfacing means. In other embodiments, components interface in an engaging manner, which does not necessary mechanically couple or fix the components together, but rather constrains their relative movement and enables the treated segment to mimic the function and movement of a healthy segment. Typically, spinal interconnecting means is a dorsally positioned component, i.e., positioned posteriorly of the superior and inferior components, or may be a laterally positioned component, i.e., positioned to the outer side of the posterior and inferior components. The structures may involve one or more struts and/or joints that provide for stabilized spinal motion. The various system embodiments may further include a band, interchangeably referred to as a ligament, which provides a tensioned relationship between the superior and inferior components and helps to maintain the proper relationship between the components.

Reference will now be made in detail to the present embodiments of the invention, examples of which are illustrated in the accompanying drawings. Wherever possible, the same reference numbers will be used throughout the drawings to refer to the same or like parts.

Figure 3A:
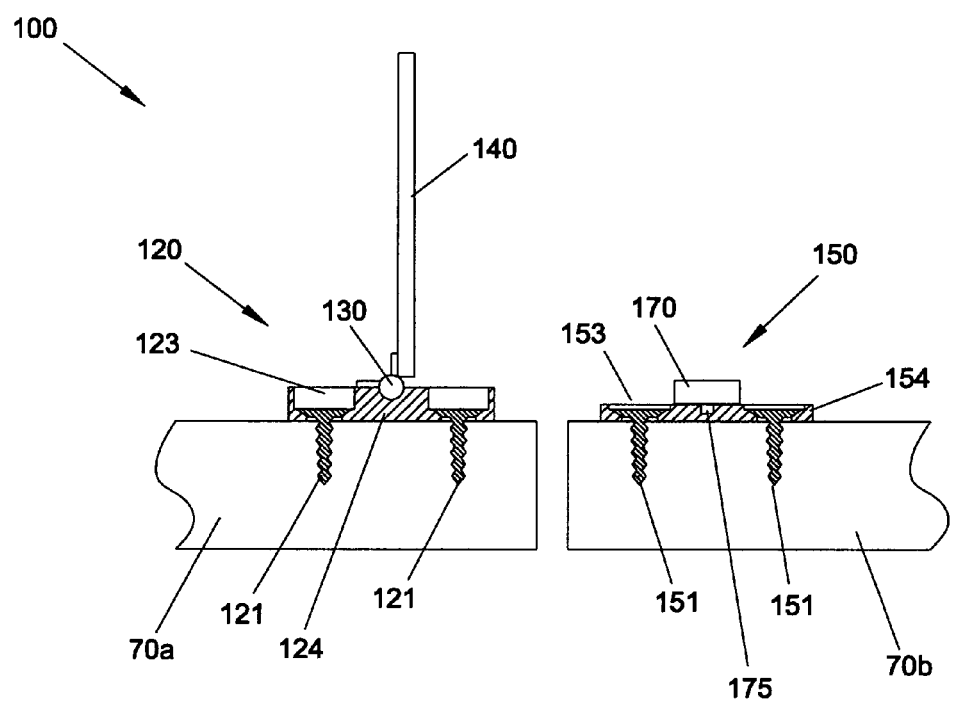

Referring now to FIGS. 3A-3C, there is illustrated a bone stabilization device 100 operatively implanted into a patient. Device 100 includes hinged assembly 120 which has been attached to first bone segment 70a, and a receiving assembly 150 which has been attached to second bone segment 70b. Bone segments 70a and 70b can take on numerous forms, such as two segments from a broken bone such as a femur, tibia and/or fibula of the leg, or the humerus, radius and/or ulna bones of the forearm. In a preferred embodiment, bone segments 70a and 70b are vertebrae of the patient, such as adjacent vertebra or two vertebra in relative proximity to each other. Device 100 may be implanted to promote healing, reduce or prevent pain, restore motion, provide support and/or perform other functions. Device 100 may be utilized to stabilize bone segments, to prevent or limit movement and/or to dynamically control movement such as to provide restoring or cushioning forces. Device 100, specifically applicable to uses wherein the bone segments 70*a* and 70*b* are vertebrae of the patient, may stabilize these segments yet dynamically allow translation, rotation and/or bending of these spinal segments, such as to restore an injured or diseased spinal segment to a near-healthy state. In an alternative embodiment, device 100 is inserted into a patient, such as a healthy or unhealthy patient, to enhance spinal motion, such as to increase a healthy patient's normal ability to support large amounts of weight, such as for specific military applications, and/or be conditioned to work in unusual environments such as the gravity reduced environments of locations outside earth's atmosphere or at high pressure locations such as in deep-water scuba diving.

Device 100 may be implanted for a chronic period, such as a period over thirty days and typically an indefinite number of years, a sub-chronic period such as a period greater than twenty-four hours but less than thirty days, or for an acute period less than 24 hours such as when device 100 is both placed and removed during a single diagnostic or therapeutic procedure. Device 100 may be fully implanted under the skin of the patient, such as when chronically implanted, or may exist both outside the skin and in the patient's body, such as applications where the stabilization components reside above the patient's skin and anchoring screws pass through the skin and attach these stabilization components to the appropriate bone structures.

Referring back to FIGS. 3A through 3C, hinged assembly 120 is anchored to bone segment 70*a* with two screws 121, such as bone screws or pedicle screws when bone segment 70*a* is a vertebra, passing through base 124. Screws 121 may be inserted in a pre-drilled hole, such as a hole drilled over a pre-placed guidewire with a cannulated bone drill and/or the screws may include special tips and threads that allow the screws to self-tap their insertion. The screws may include one or more treatments or coatings, such as including a Teflon layer that supports long-term removal of the screw from the bone, such as to replace an implanted component. In a preferred embodiment, screw 121 includes threads that include a surface configured to prevent anti-rotation or loosening, such as an adhesive surface or a grooved surface whose grooves are aligned to support rotation in a single direction only. In another preferred embodiment, the screws include expansion means, such as hydraulic or pneumatic expansion means, which allow the diameter of the thread assembly to slightly increase or decrease on demand to facilitate secure long-term attachment, as well as ease of removal.

Base 124 includes recess 123, which is a countersink that allows the tops of screws 121 to reside below the top surface of base 124 when anchored to bone segment 70*a*. In an alternative embodiment, an articulating element, not shown, is included allowing hinged assembly 120 to move relative to bone segment 70*a*. Attached to base 124 is hinge 130, which rotatably attaches base 124 to pivoting arm 140. Hinge 130 shown is a pin and bushing construction similar to a door hinge. Numerous alternatives may be employed, additionally or alternatively, some of which are described in detail in reference to subsequent figures, without departing from the spirit can scope of this application. Hinge 130 may include a ball and socket construction, or may simply consist of a flexible portion integral to pivoting arm 140, base 124 and/or a flexible element that couples base 124 to pivoting arm 140. Hinge 130 may be configured to allow one or more degrees of freedom of motion of pivoting arm 140 relative to base 124. Hinge 130 may be an attachable hinge, such as a hinge that is assembled by an operator during the surgical procedure but prior to passing hinged assembly 120 through the skin of the patient. Alternatively hinge 130 may be preattached, and may not be able to be disassembled by the operator during or subsequent to the implantation procedure.

Also depicted in FIGS. 3A through 3C is receiving assembly 150, which is configured to be securely attached to second bone segment 70*b* with attachment screws 151, which are preferably similar to attachment screws 121. Screws 151 are similarly passed through base 154 such that the head of screw 151 resides entirely within recess 153. In an alternative embodiment, an articulating element, not shown, is included allowing receiving assembly 150 to move relative to bone segment 70*b*. Securely attached to base 154 is cradle 170, configured to attach to the distal end of pivoting arm 140. Cradle 170 may be fixedly attached to base 154, or may include an articulating member, not shown, to allow a limited range of motion between cradle 170 and base 154. Cradle 170 includes threads 175 which are configured to receive a securing element, such as a set screw, to maintain pivoting arm 140 in a secured connection with receiving assembly 150.

Referring specifically to FIG. 3B, pivoting arm 140 has been rotated approximately forty-five degrees in a clockwise direction, such that the distal end of arm 140 has traversed an arc in the direction toward cradle 170. Referring specifically to FIG. 3*c*, arm 140 has been rotated approximately an additional forty-five degrees, a total of ninety degrees from the orientation shown in FIG. 3*a*, such that the distal end of arm 140 is in contact or otherwise in close proximity with cradle 170. A securing device, locking screw 171 has been passed through a hole in the distal end of arm 140 and threaded into threads 175 of cradle 170, such that a stabilizing condition has been created between first bone segment 70*a* and second bone segment 70*b*. This stabilizing condition, as has been described above, can take on a number of different forms, singly or in combination, such as fixed stabilization and dynamic stabilization forms. Dynamic stabilization provides the benefit of allowing motion to occur, such as normal back or other joint motions that a fixed stabilization device may prevent or compromise.

Cradle 170 of FIGS. 3A through 3C includes a "U" or "V" shaped groove, end view not shown, which acts as a guide and accepts the distal end of arm 140. Arm 140 is securely attached in a fixed connection shown through the placement of screw 171 through arm 140 and in an engaged position with threads 175 of cradle 170. In an alternative embodiment, dynamic stabilization between first bone segment 70*a* and second bone segment 70*b* is achieved by the creation of a dynamic or "movable" secured connection between the distal end of arm 140 and cradle 170. In an alternative or additional embodiment, dynamic stabilization between first bone segment 70*a* and second bone segment 70*b* is achieved via a dynamic secured connection between hinge 130 and base 124 of hinged assembly 120. In yet another additional or alternative embodiment, dynamic stabilization of first bone segment 70*a* and second bone segment 70*b* is achieved via pivoting arm 140, such as an arm with a spring portion, such as a coil or torsional-compress spring portion, or by an otherwise flexible segment integral to arm 140. Arm 140 may take on numerous forms, and may include one or more functional elements, described in detail in reference to subsequent figures. Arm 140 may include multiple arms, such as arms configured to perform different functions. In an alternative embodiment, described in detail in reference to FIG. 14*c*, arm 140 may include a hinge-like flexible portion, performing the function of and obviating the need for hinge 130.

Cradle 170 may also take on numerous forms, in addition or alternative to the grooved construction of FIGS. 3A through 3C. Cradle 170 performs the function of securing arm 140 to receiving assembly 150, such as via screw 171 engaging threads 175. In alternative embodiments, numerous forms of attaching a rod to a plate may be used, with or without a guiding groove, including retaining rings and pins, belts such as flexible or compressible belts, and other fixed or dynamic stabilization means. Screw 171 is placed by an operator, such as a clinician inserting and rotating screw 171 through a dilating cannula used in a minimally invasive percutaneous procedure, such that when screw 171 engages threads 175, pivoting arm 170 stabilizes hinged assembly 120 and receiving assembly 150 relative to each other, thus stabilizing first bone segment 70a and second bone segment 70b relative to each other. Insertion and engagement of screw 171 into threads 175 provides stabilization of hinged assembly 120 and receiving assembly 150 in two ways. First, motion between arm 140 and receiving assembly 150 is stabilized. Also, motion between arm 140 and base 124 of hinged assembly 120 is stabilized. In an alternative or additional embodiment, when pivoting arm 120 is pivoted, such as to the location shown in FIG. 3c, an automatic locking tab, not shown, is automatically engaged with further operation of the operator, such that pivoting arm 140 is prevented from pivoting back (in a counterclockwise direction as depicted in FIG. 3C). In another alternative or additional embodiment, described in detail in reference to FIGS. 20, 20A and 20B, an automatic engaging assembly is integral to cradle 170, such as a "U" shaped groove with a projection at the top of the "U" that allows arm 140 to snap in place into a secured configuration. Numerous other automatic or semi-automatic engaging mechanisms, such as those that limit rotation of arm 140 and/or secure the distal end of arm 140, may be employed in hinged assembly 120 and/or receiving assembly 150.

The components of system 100 of FIGS. 3A are configured to be used in an open surgical procedure as well as a preferred minimally invasive procedure, such as an over-the-wire percutaneous procedure. Hinged assembly 120 and receiving assembly 150 preferably can each be inserted through one or more cannulas previously inserted through relatively small incisions through the patient's skin. Devices and methods described in reference to FIGS. 4A, 4B and 4C, as well as FIGS. 6A through 6H include components with cannulated (including a guidewire lumen) bone anchors and other components with lumens and or slots that allow placement over a guidewire as well as one actions that can be completed with a guidewire in place, such actions including but not limited to: securing to bone, rotation of the pivoting arm, and securing of the pivoting arm to the receiving assembly.

Figure 4:
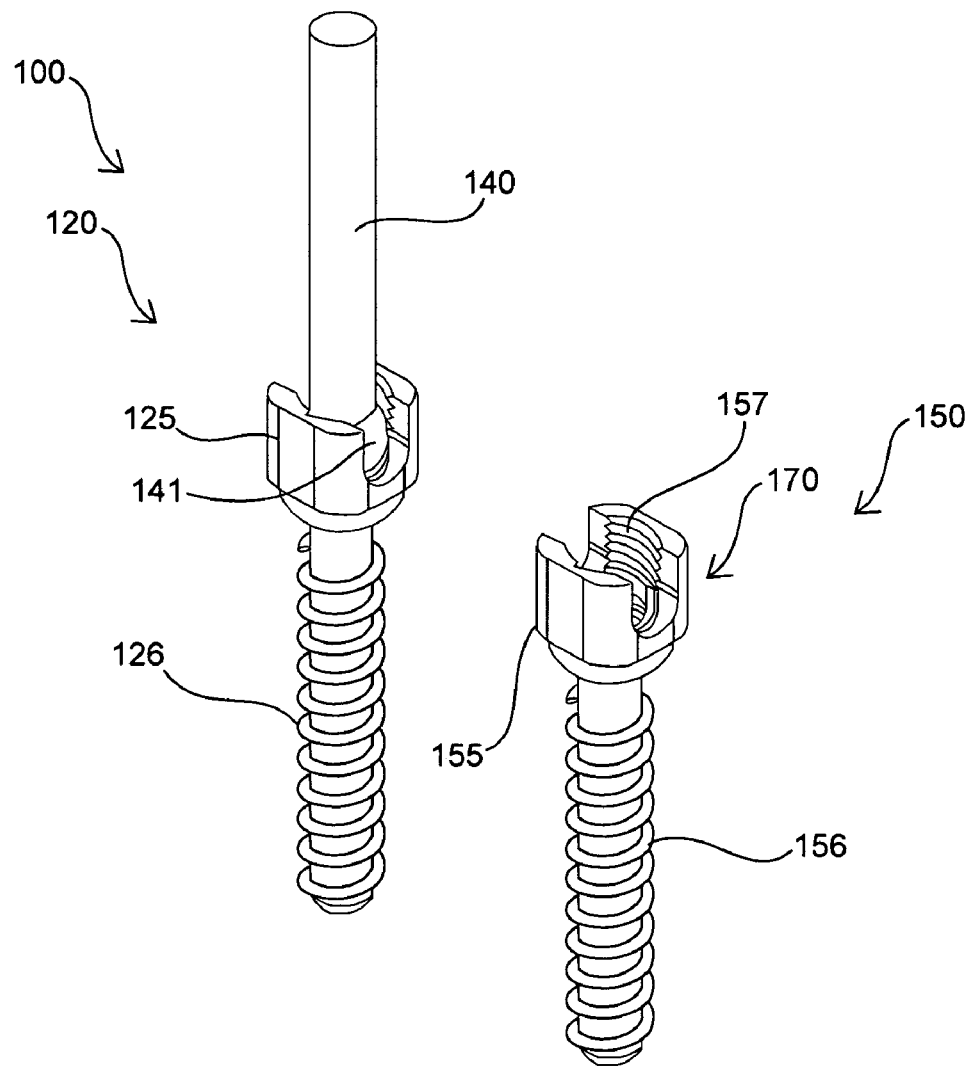
FIG. 4 illustrates a perspective view of a bone stabilization device consistent with the present invention.
Figure 4A:
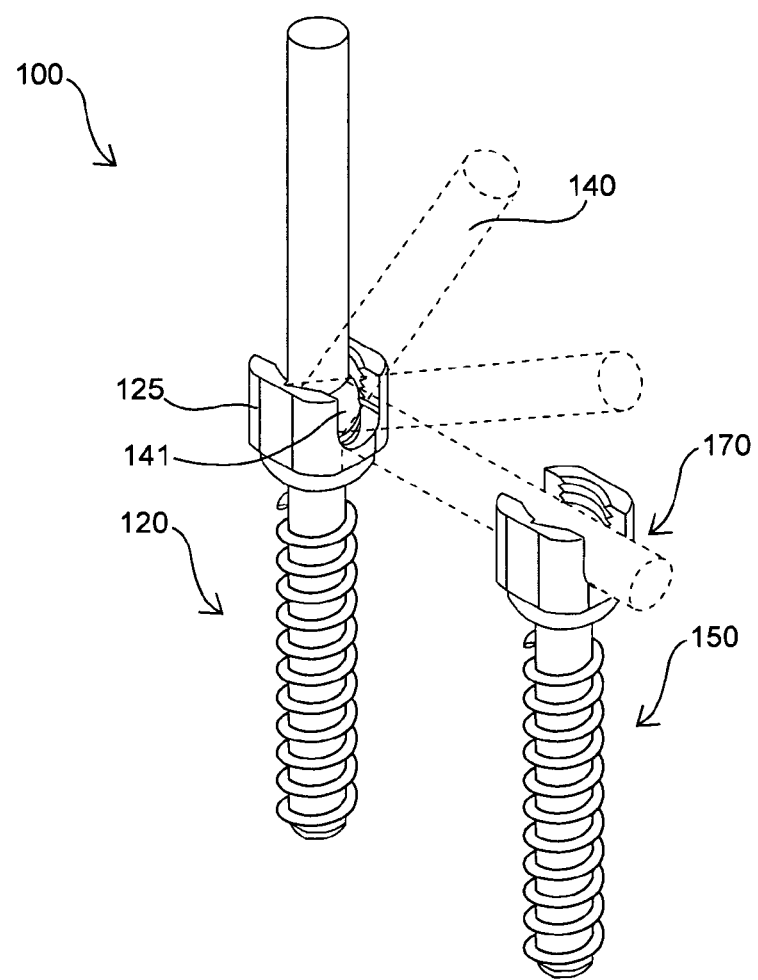
FIGS. 4A and 4B illustrate a perspective view of the bone stabilization device of FIG. 4 shown with the pivoting arm rotating through an arc and engaged with an attaching cradle, respectively.
Figure 4B:
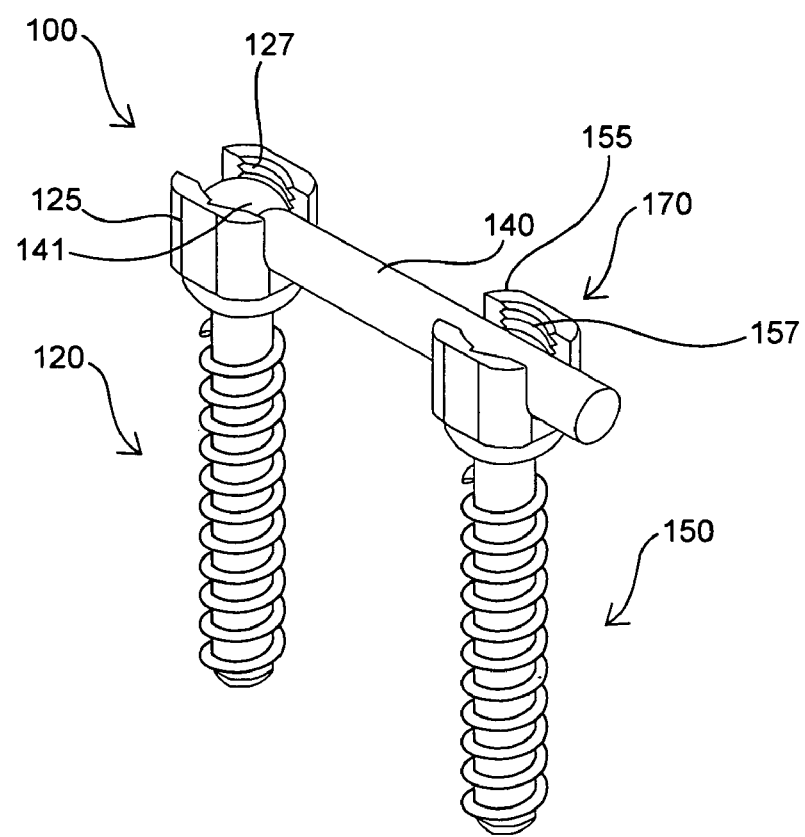

Referring now to FIGS. 4, 4A and 4B, a preferred embodiment of a bone stabilization device of the present invention is illustrated in which each of the hinged assembly and the receiving assembly include cannulated bone screws that are configured to anchor into bone as rotated (while placed over a guidewire), and the hinged assembly pivoting arm hinge comprises a ball and socket configuration. Device 100 includes hinged assembly 120 comprising pivoting arm 140 and a bone anchoring portion including screw head 125 and bone threads 126. Screw head 125 includes one or more surfaces configured to engage with a tool, such as a percutaneously inserted socket wrench or screwdriver, to engage and rotate hinged assembly 120. Screw head 125, and all the similar screws of the present invention, are preferable polyaxial screw heads, such as the heads included in polyaxial pedicle screws commonly used in spine surgery. A lumen, not shown, passes through arm 140 and inside the tube surrounded by threads 126 such that hinged assembly 120, in the orientation shown in FIG. 4, can be placed into the patient through a cannula and over a previously placed guidewire, such as a "K-wire" commonly used in bone and joint procedures.

At the end of arm 140 is ball end 141, which is rotationally received and captured by screw head 125. Arm 140 can be inserted into screw head 125 by an operator, or may be provided in a pre-attached state. Arm 140 can be removable from screw head 125, or may be permanently, though rotatably, attached, whether provided in a "to-be-assembled" or a pre-assembled state. The ball and socket design of FIG. 4 allows multi-directional rotation of pivoting arm 140. Alternative designs, may allow a single degree of freedom, and/or may allow more sophisticated trajectories of travel for the distal end of arm 140.

System 100 further includes receiving assembly 150, which similarly includes a bone anchor comprising screw head 155, preferably a polyaxial screw head, and bone threads 156. Within the tube surrounded by bone threads 156 is a guidewire lumen that is configured to allow carrier assembly 150 to be placed through a cannula and over a guidewire that has previously been placed into the bone of a patient. Screw head 155 includes one or more surfaces configured to engage with a tool, such as a percutaneously inserted socket wrench or screwdriver, to engage and rotate receiving assembly 150. Cradle 170 comprises a "U" shaped groove that is sized and configured to accept and capture the distal end of pivoting arm 140. Cradle 170 may include positive engagement means such as threads 157, or other securing means such as a projecting member that is configured to provide a snap fit, magnetic holding means, pivoting engagement means such as a rotatable holding arm, adhesive holding means, or other retention elements all not shown.

Referring specifically to FIG. 4A, pivoting arm 140 is shown in multiple stages of rotation, including the starting position of FIG. 4 in which pivoting arm 140 and threads 126 are linearly aligned to allow over-the-wire insertion. After threads 126 are properly engaged with bone, pivoting arm 140 is rotated, in a clockwise direction as shown, to a point in which it engages with receiving assembly 150, preferably a near ninety degree rotation as shown, but alternatively a smaller or greater angle as determined by the orientation of the two bone segments to be stabilized. Arm 140 may be rotated with the guidewire removed, or may include a slot, not shown, that allows arm 140 to "separate" from the guidewire as arm 140 is rotated. In an alternative embodiment, hinged assembly 120 includes a cannulated screw, but arm 140 is not cannulated, traveling along side the guidewire during insertion, and rotating about the guidewire during rotation and bone anchoring of threads 126. In this alterative embodiment, a slot is not required to rotate arm 140, in a direction away from central axis of the in-place guidewire.

Referring now specifically to FIG. 4B, pivoting arm 140 has been rotated and engaged with cradle 170 of receiving assembly 150. In the preferred method of placing system 100 components through cannulae and over previously placed guidewires, pivoting arm 140 distal end passes through an arc that resides under the skin of the patient. Rotation of arm 140 is preferably accomplished with one or more pivoting tools, such as a percutaneous tool placed through the in-place cannula through which hinged assembly 120 was inserted. Detailed descriptions of a preferred percutaneous insertion method is described in reference to FIGS. 6a through 6h described herebelow. In the embodiment of FIG. 4B, both screw head 125 and screw head 155 include securing means, threads 127 and 157 respectively, into each of which a set screw, not shown, is placed to "lock in place" pivoting arm 140 and provide high levels of stabilization forces, including axial forces, radial forces and torsional forces. Threads 127 and 157 as well as the corresponding set screws, are configured to provide sufficient anti-rotation properties to prevent loosening over time, such as anti-rotation achieved with specific thread patterns and/or included adhesive. In an alternative embodiment, the engagement shown in FIG. 4B, without additional set screws into either threads 127 or threads 157, provides the necessary stabilization forces. In another alternative embodiment, an automatic anti-rotation mechanism engages when sufficient rotation of arm 140 is achieved, simplifying the procedure for the operator, such as by simplifying the placement of a set screw into threads 157 with an already locked in place pivoting arm 140.

Referring now to FIG. 5, an exploded view of a preferred construction of the bone stabilization device of the present invention is provided. Hinged assembly 120 includes multiple components captured by the dashed line of FIG. 5. Pivoting arm 140 includes ball end 141 at its proximal end. Ball end 141 is sized and configured to be received by screw head 125 such that a rotatable hinge is formed, allowing the distal end of arm 140 to be rotated in numerous directions. Ball end 141 may be inserted by the operator, such as during a sterile procedure prior to insertion into the patient, or be provided pre-assembled by the manufacturer. Hinged assembly 120 further includes a bone anchor comprising an elongate tube with bone threads 126, ball end 128 and thru lumen 161, a lumen sized and configured to facilitate placement of hinged assembly 120 over a guidewire, such as a guidewire placed into a bone segment to be stabilized. Ball end 128 is sized and configured to be securely engaged with pivoting element 129, which in turn securely engages with screw head 125, such that polyaxial rotation of screw head 125 is achieved, such as rotation which simplifies insertion of hinged assembly 120 in a vertebra or other bone structure during an over-the-wire, through-a-cannula, percutaneous procedure.

The bone stabilization device of FIG. 5 further includes receiving assembly 150, also including multiple components captured by the dashed line of FIG. 5. Receiving assembly 150 includes cradle 170, an attachment point for the distal end of pivoting arm 140 of hinged assembly 120. Cradle 170 comprises screw head 155 that includes a "U" shaped groove for slidingly receiving the distal end of arm 140. In a preferred embodiment, the geometry of the "U" shape groove provides a snap fit to (permanently or temporarily) maintain the pivoting arm in place such as behind held in place during a further securing event. Receiving assembly 150 further includes a bone anchor comprising an elongate tube with bone threads 156, ball end 158 and thru lumen 162, a lumen sized and configured to facilitate placement of receiving assembly 150 over a guidewire, such as a guidewire placed into a bone segment to be stabilized. Ball end 158 is sized and configured to be securely engaged with pivoting element 159, which in turn securely engages with screw head 155, such that polyaxial rotation of screw head 125 is achieved, such as rotation which simplifies insertion of hinged assembly 120 in a vertebra or other bone structure during an over-the-wire, through-a-cannula, percutaneous procedure.

Screw head 155 of receiving assembly 150 includes means of securing the distal end of pivoting arm 140, threads 157 which are configured to accept a set screw after arm 140 is slidingly received by the groove of screw head 155, thus locking the distal arm in place. Set screw 171 can be inserted and engaged by an operator into threads 157, such as in an over-the-wire placement procedure through the lumen of screw 171 shown, Additional stabilization can be attained by inserting an additional set screw, set screw 142, into threads 127 of screw head 125 of the hinged assembly. Set screw 142 is also configured to be delivered in an open surgical procedure, or preferably an over-the-wire percutaneous procedure as placed through a similar lumen in screw 142. When threads 126 of hinged assembly 120 and threads 156 of receiving assembly 150 are anchored in bone, and pivoting arm 140 is secured within cradle 170, stabilization between hinged assembly 120 and receiving assembly 150 is achieved. In a preferred embodiment, pivoting arm 140 is configured to provide one or more of numerous parameter of stabilization, including but not limited to: rigid or fixed stabilization, and dynamic stabilization such as stabilization that allows controlled or limited motion in one or more directions. Pivoting arm 140 may be rigid, or have some degree of flexibility. Pivoting arm 140 may include one or more functional elements, such as a spring to resists but permits motion. Functional elements may include one or more engaging surfaces, such as surfaces that permit motion in one or more directions, yet limit motions in other directions, or surfaces which allow motion in a particular direction within a finite distance. Functional elements may provide other functions, such as an agent delivery element which provides an anti-infection agent or an agent targeted at reducing bone growth that otherwise would limit motion. These and other functions of pivoting arm 140 are described in detail in reference to subsequent figures herebelow.

Figure 6A:
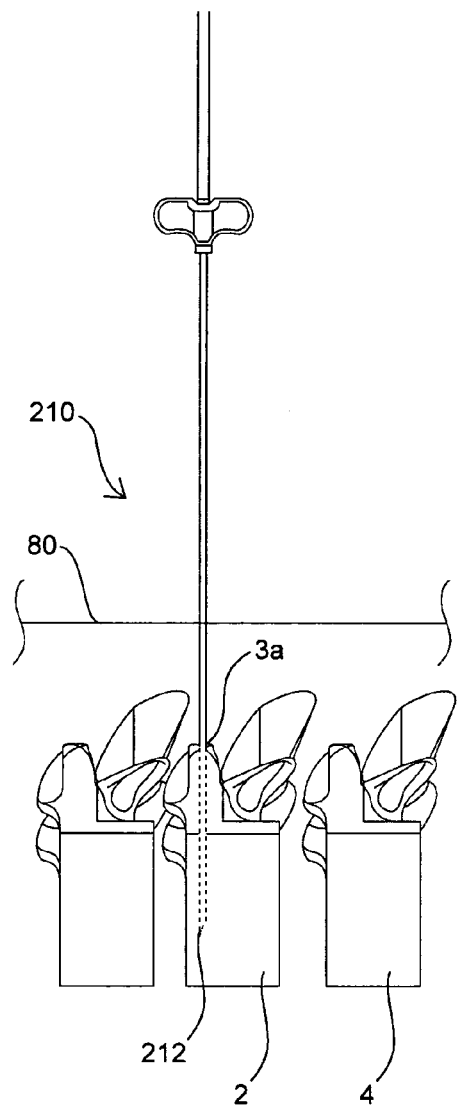
Figure 6B:
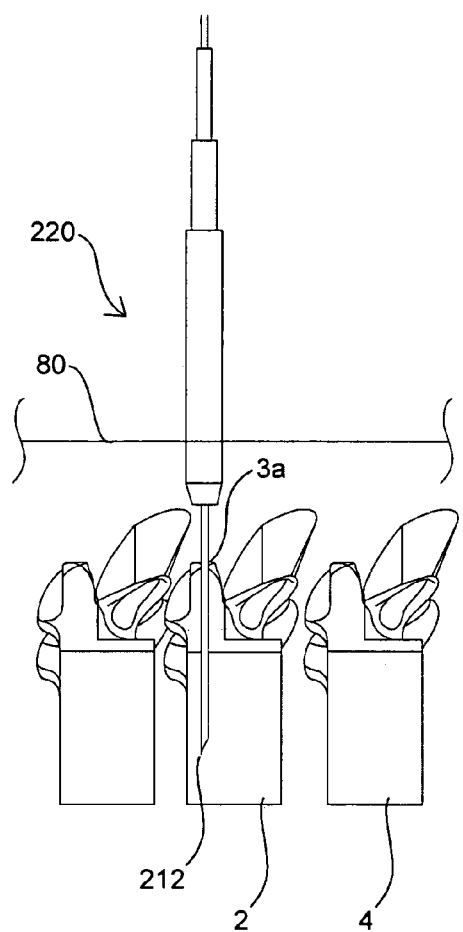

Referring now to FIGS. 6A through 6H, a preferred method of stabilizing one or more patient bone segments, specifically vertebral segments, is illustrated. Referring to FIG. 6a, a guidewire placement procedure is illustrated in which a puncture has been made through the patient's skin 80, and into the pedicle 3a of patient vertebra 2. A guidewire 212, such as a K-wire, is shown in place, allowing subsequent devices to be passed over guidewire 212, using standard over-the-wire techniques. Referring now to FIG. 6b, a sequential dilation is being performed for the purpose of having a sufficiently sized cannula, dilating cannula 220, in place over guidewire 212. Dilating cannula 220 is positioned above, and with its central axis aligned with, vertebra 2 such that additional devices can be inserted over guidewire 212 and within a lumen of cannula 220 to access pedicle 3a and surrounding areas. The sequential dilation is performed to minimize tissue trauma that would result from initial insertion of the final, large sized cannula to be used.

Figure 6C:
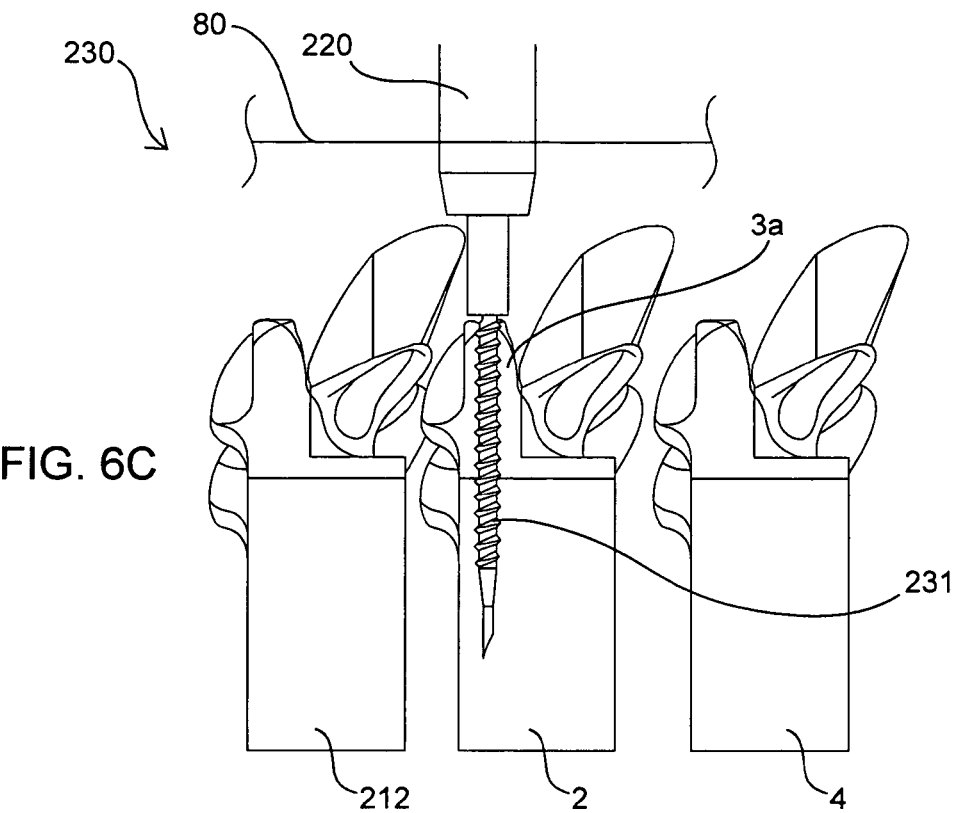
Figure 6D:
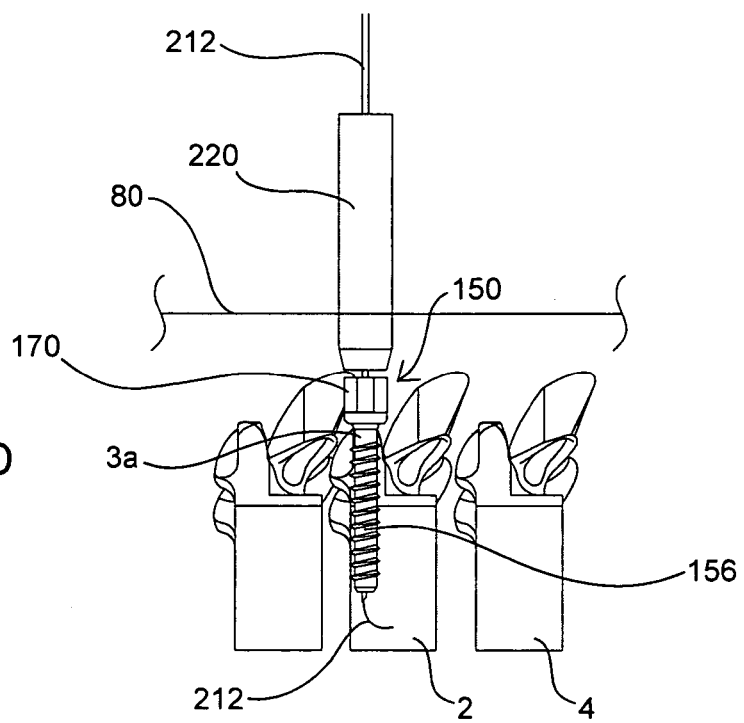

Referring now to FIG. 6C, a cannulated drill bit 231 has been placed through cannula 220, over guidewire 212 and is in operable connection with cannulated drill 230. Drill bit 231 is near completion of drilling an appropriately sized hole into pedicle 3a of vertebra 2, such that an anchoring screw can be placed in a subsequent step. Referring now to FIG. 6D, cannulated drill bit 231 has been removed, using an over-the-wire removal or exchange technique, and receiving assembly 150 of the bone stabilization device of the present invention has been placed through cannula 220 and over guidewire 212. Receiving assembly 150 has been inserted with its bone anchoring portion and its attaching cradle 170 in an aligned, linear configuration. Guidewire 212 has been passed through a lumen, not shown but within both the anchoring portion and attaching cradle 170 of receiving assembly 150. In an alternative embodiment, guidewire 212 passes through a lumen of the anchoring portion, but then passes alongside attaching cradle 170 of receiving assembly 150. Receiving assembly 150 has been rotated, such as with a screwdriver tool or socket wrench tool passed through cannula 220 and engaging one or more portions of receiving assembly 150, tool not shown, such that its threads 156 are fully engaged with pedicle 3a of vertebra 2. In a preferred embodiment, these rotating tools include a thru lumen and are also inserted and manipulated over-the-wire.

Figure 6E:
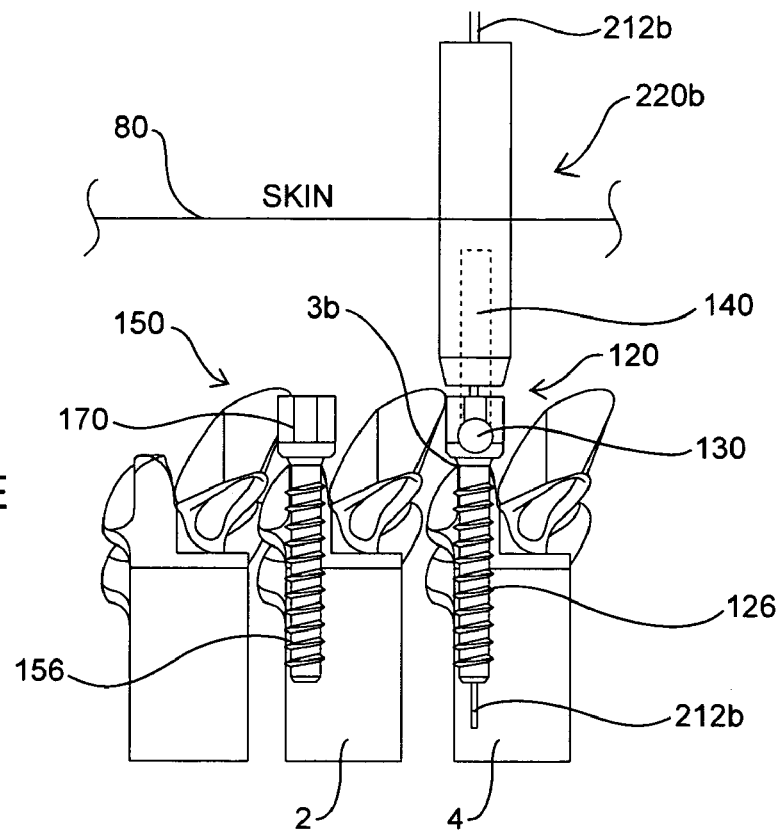

Referring now to FIG. 6E, an adjacent vertebra, patient vertebra 4, has undergone similar access techniques, including guidewire placement, sequential dilation and pedicle drilling. As shown, receiving assembly 150 remains in place with threads 156 anchoring receiving assembly 150 to vertebra 2, and cradle 170 positioned to receive one or more pivoting arms of the present invention. Dilating cannula 220b has been inserted, such as the same cannula as previous figures or an additional cannula with cannula 220 remaining in place, not shown but as depicted in FIG. 6D. Guidewire 212b, preferably a K-wire, passes within cannula 220b, through the patient's skin 80 and into pedicle 3b of patient vertebra 4. Vertebra 4 is shown as an adjacent vertebra but in an alternative embodiment, vertebra 4 may be separated from vertebra 2 by one or more additional vertebrae, with the associated pivoting arm sized accordingly.

Referring back to FIG. 6E, cannula 220b is positioned above, and with its central axis aligned with, vertebra 4 such that additional devices can be inserted over guidewire 212b and within a lumen of cannula 220b to access pedicle 3b and surrounding areas. Hinged assembly 120 has been inserted with its bone anchoring portion, its pivoting arm 140 and hinge 130 in an aligned, linear configuration as shown. Prior to its insertion, hinged assembly 120 may have been assembled by the operator, such as an operator in the sterile field connecting the pivoting arm to the anchor portion, or may have been provided by the manufacturer in an assembled state. Guidewire 212b has been passed through a lumen, not shown but within both the anchoring portion and pivoting arm 140 of hinged assembly 120. In an alternative embodiment, guidewire 212b passes through a lumen of the anchoring portion, but then passes alongside attaching pivoting arm 140 of hinged assembly 120. Hinged assembly 120 has been rotated, such as with a screwdriver tool or socket wrench tool passed through cannula 220b and engaging one or more portions of hinged assembly 120, tool not shown, such that its threads 126 are fully engaged with pedicle 3b of vertebra 4. In a preferred embodiment, these rotating tools include a thru lumen and are also inserted and manipulated over-the-wire. In another preferred embodiment, the rotating tool includes an open lumen on its distal end sized to slide over the distal end of pivoting arm 140 and engage one or more engagable surfaces integral to hinged assembly 120 and located at or near hinge 130.

Figure 6F:
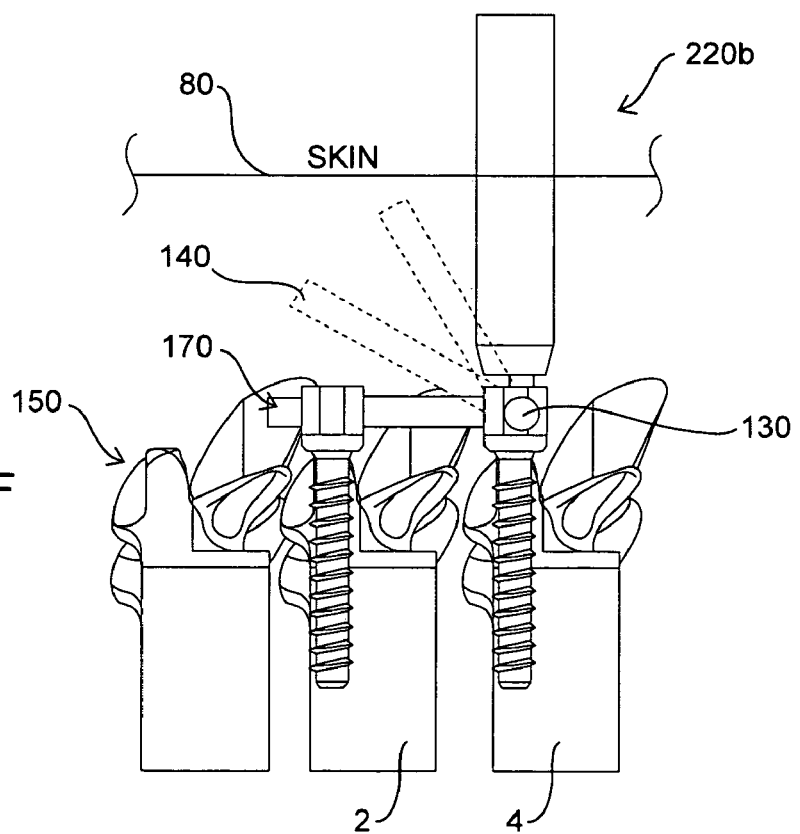

Referring now to FIG. 6F, hinged assembly 130 is securely attached to vertebra 4, an pivoting arm 140 is being rotated, such that the distal end of arm 140 forms an arc that remains under patient's skin 80, and is slidingly received into a groove of attaching cradle 170 of receiving assembly 150. Pivoting arm 140 may rotably pass through a slot in cannula 220b, not shown but described in detail in reference to FIGS. 7 and 7a. Alternatively, cannula 220b can be retracted a sufficient distance to allow pivoting arm 140 to swing below the distal end of cannula 220b. In the embodiment shown in FIG. 6f, guidewire 212b has been removed to allow pivoting arm 140 to freely swing toward cradle 170. In an alternative embodiment, pivoting arm 140 includes a slot from its thru lumen to it's outer surface such that arm 140 can be pivoted away from a guidewire. In another alternative embodiment, hinged assembly 120 is inserted such that pivoting arm 140 is not over-the-wire, i.e. does not include a guidewire lumen and is inserted with pivoting arm alongside the guidewire. In this embodiment, arm 140 can also be rotated with the guidewire in place.

Figure 6G:
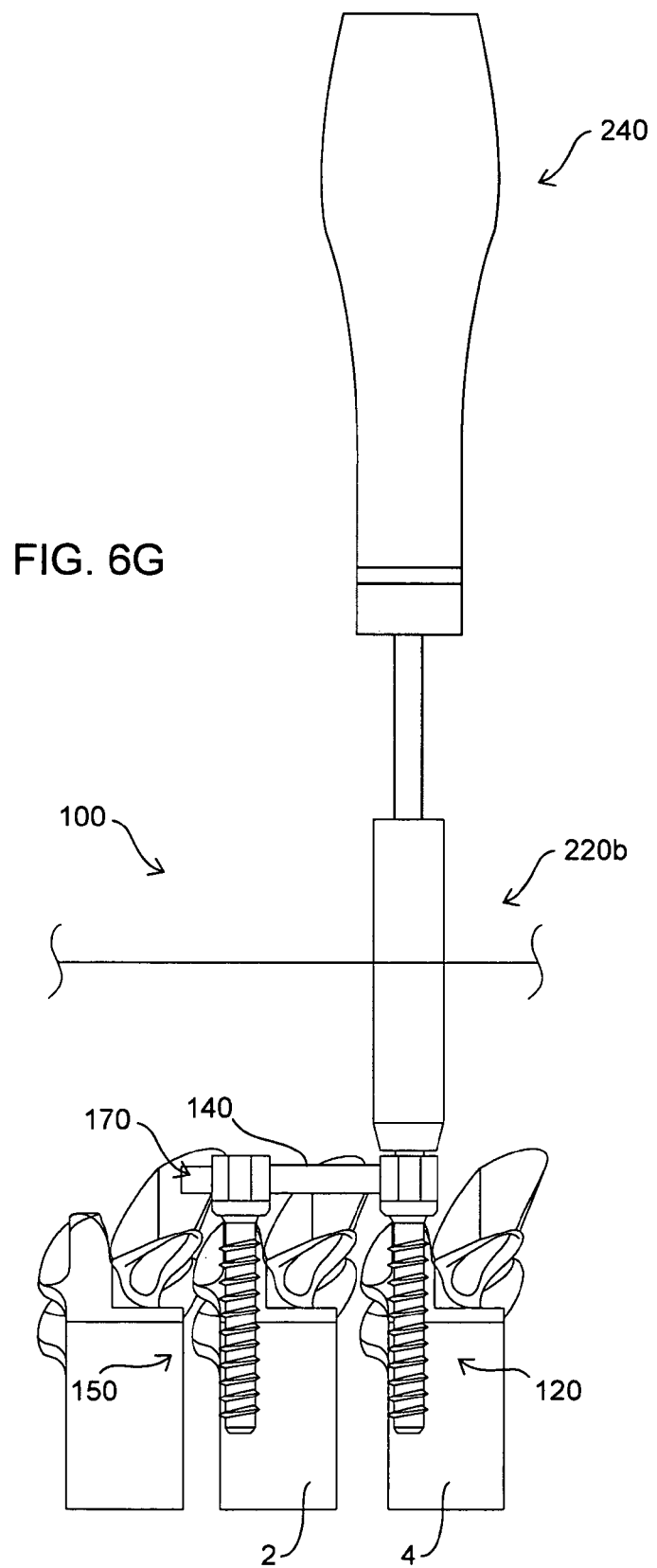

Referring now specifically to FIG. 6G, a percutaneous screwdriver 240 of the present invention has been inserted within the lumen of cannula 220b and is rotatably engaging a set screw, now shown but as has been described in reference to FIG. 5 hereabove, to secure pivoting arm 140 to prevent or limit rotation. In a preferred embodiment, screwdriver 240 and inserted set screws include lumens such that each can be inserted over an in-place guidewire. In another preferred embodiment, not shown, percutaneous screwdriver 240 is similarly inserted within the lumen of cannula 220, not shown but aligned with receiving assembly 150 as shown in FIG. 6D, such that another engaging set screw can be inserted, into cradle 170, to securely attach pivoting arm 140 to cradle 170. Referring now to FIG. 6H, the cannulae and guidewires have all been removed, and bone stabilization device 100 is implanted in the patient. Receiving assembly 150 is securely attached to vertebra 2, and hinged assembly 120 is securely attached to vertebra 4. Pivoting arm 140 is securely attached to receiving assembly 150 thus providing stabilization between vertebra 2 and vertebra 4. The type and amount of stabilization achieved between the two vertebrae can take on the various forms described throughout this application, including but not limited to: fixed or fused stabilization, and dynamic stabilization.

Figure 7:
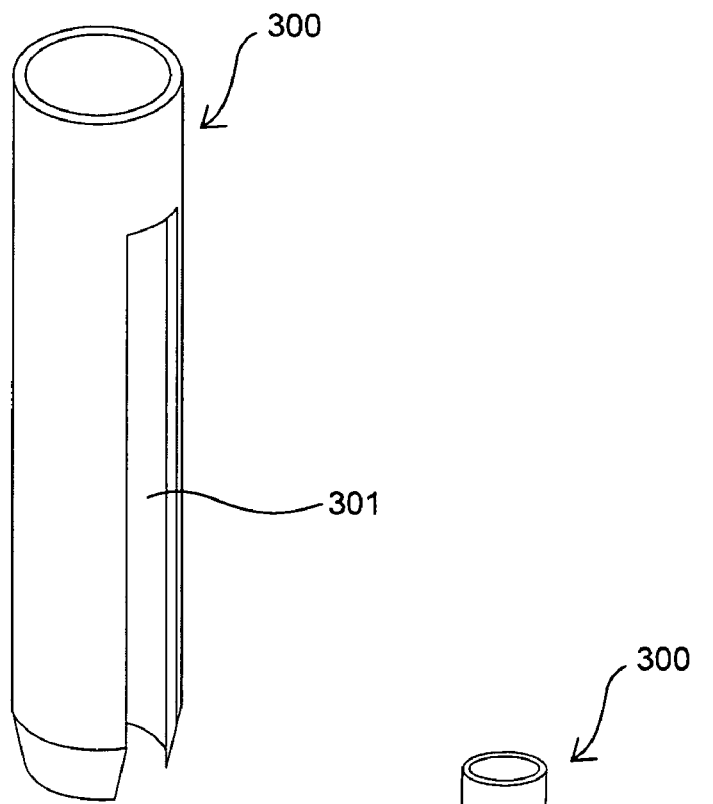
FIG. 7 illustrates a perspective view of a slotted cannula consistent with the present invention.
Figure 7A:
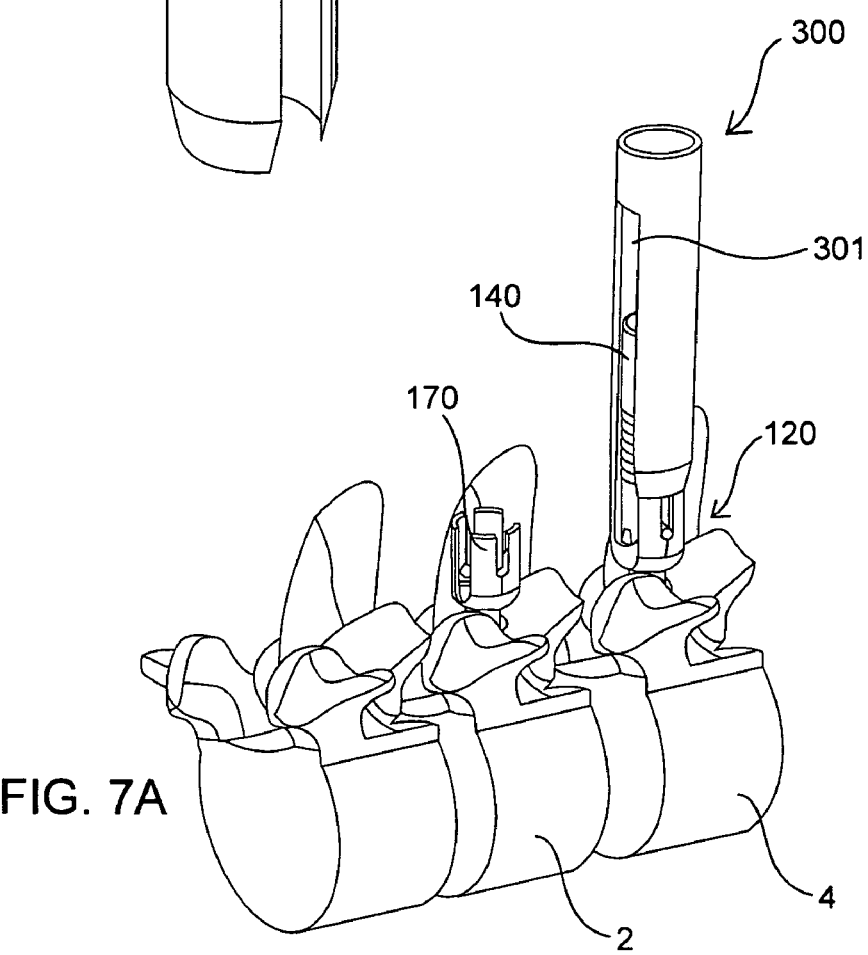
FIG. 7A illustrates a perspective view of the slotted cannula of FIG. 7 positioned to access or place a device at a vertebral segment of a patient.

Referring now to FIG. 7, a slotted cannula of the present invention is illustrated. Slotted cannula 300, preferably a sequential dilating cannula, additional sliding tubes not shown, includes a longitudinal slot, starting from its distal end, the end that is inserted into the patient, and extending proximally. Slot 301, and any additional slots included in any slidingly received tubes not shown, are sized and positioned such that a device contained within cannula 300 can be passed through the slot, such as to a location within the body of a patient. Referring now to FIG. 7A, slotted cannula 300 is shown passing through the skin of a patient, skin not shown, and aligned with vertebra 4 of the patient. Hinged assembly 120 of the present invention is included within the lumen of cannula 300 and has been securely attached to vertebra 4. Also shown is the receiving assembly of the present invention with attaching cradle 170 having been securely attached to vertebra 2 of the patient. Slot 301 of cannula 300 has been aligned such that pivoting arm 140 of hinged assembly 120 can be rotated to the orientation in which the distal end of arm 140 is slidingly received by the groove of cradle 170 without having to reposition cannula 300. In a preferred embodiment, the proximal end of slotted cannula 300 includes one or more markings that indicate the location of slot 301 such than when inserted in the body, slot 301 position can be oriented and/or confirmed. In an alternative embodiment, dilator 300 includes multiple slots along its length.

Figure 8:
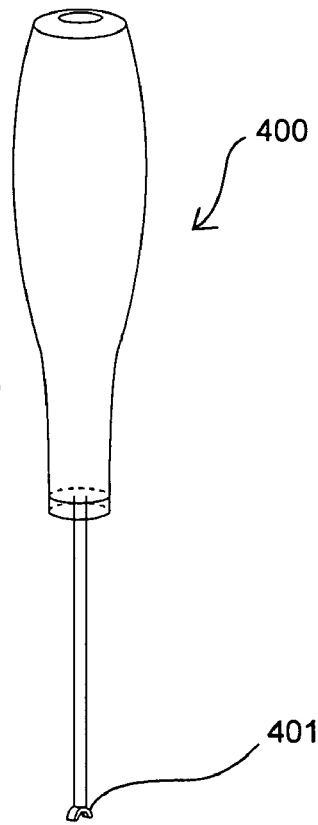
FIG. 8 illustrates a perspective view of a pivoting tool consistent with the present invention.
Figure 8A:
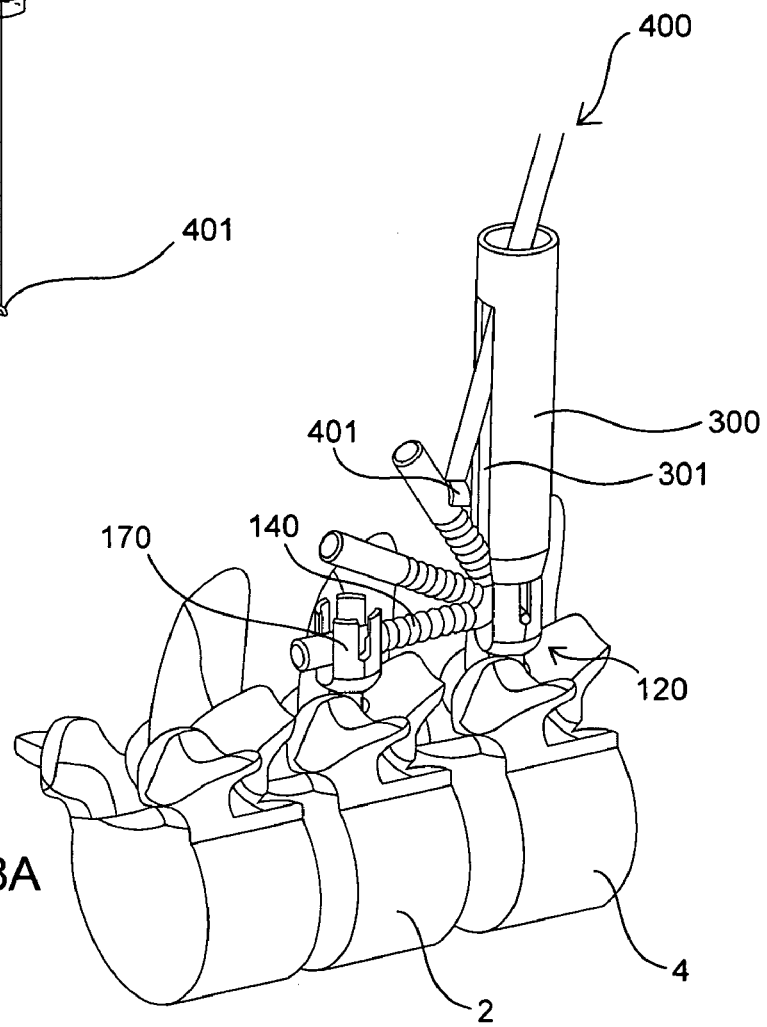
FIG. 8A illustrates a perspective view of the pivoting tool of FIG. 8 positioned to rotate a pivoting arm of a hinged assembly of the present invention.

Referring now to FIG. 8, a pivoting tool of the present invention is illustrated. Pivoting tool 400 includes engagement end 401, configured to operably engage a pivoting arm of the present invention, such as to rotate the pivoting arm through one or more cannulae during a percutaneous procedure. Referring now to FIG. 8A, slotted cannula 300 is shown passing through the skin of a patient, skin not shown, and aligned with vertebra 4 of the patient. Hinged assembly 120 of the present invention is included within the lumen of cannula 300 and has been securely attached to vertebra 4. Also shown is the receiving assembly of the present invention with attaching cradle 170 having been securely attached to vertebra 2 of the patient. Slot 301 of cannula 300 has been aligned such that pivoting arm 140 of hinged assembly 120 can be rotated using pivoting tool 400 to the orientation in which the distal end of arm 140 is slidingly received by the groove of cradle 170. Pivoting arm 140 is rotated by first engaging end 401 of pivoting tool 400 with arm 140, and then advancing and potentially pivoting end 401 until arm 140 is engaged with cradle 170. In a preferred embodiment, the proximal end of pivoting tool 400 includes one or more markings that indicate the orientation of engaging end 401, such as when engaging end 401 has an non-symmetric geometry.

Referring now to FIG. 9, another preferred embodiment of the bone stabilization device of the present invention is illustrated. FIG. 9 depicts a schematic view of bone stabilization device 100 comprising hinged assembly 120 and receiving assembly 150. Hinged assembly 120 includes a bone anchoring portion including bone threads 126, that is fixedly or rotatably attached to hinge 130. Hinge 130 provides a rotatable connection, such as a single or multi-axis rotatable connection, to pivoting arm 140. Receiving assembly 150 includes a bone anchoring portion including bone threads 156, that is fixedly or rotatably attached to cradle 170. Cradle 170 is configured to be securely attached, intraoperatively, to pivoting arm 140 to achieve stabilization between a first bone location and a second bone location. The type and amount of stabilization can be greatly specific and customized as is provided in the multiple embodiments of the present invention.

As depicted in the schematic representation of FIG. 9, pivoting arm 140 includes functional element 145, depicted at the midpoint of pivoting arm 140 but existing anywhere along its length or comprising the entirety of pivoting arm 140. Also included in pivoting arm 140 is adjustment means 144, shown as part of functional element 145 but alternatively a separate component or components of functional element 145. Adjustment means 144 is an engageable assembly, preferably engageable via cannulae as has been described in reference to FIGS. 6A through 6H, placed during the procedure implanting bone stabilization device 100 or a subsequent procedure in which bone stabilization device 100 is to be adjusted. Numerous parameters of device 100 may require adjustment, at the time of implantation or thereafter, including but not limited to: force adjustments such as forces resisting translation, rotation and bending of vertebral segments; length adjustments; position adjustments; and combinations thereof. In a preferred embodiment, pivoting arm 140 is slidable within a component of device 100 or includes two slideable arms, and adjustment means 144 is a screw driven assembly that causes controlled sliding and resultant length adjustment of pivoting arm 140. In another preferred embodiment, device 100 includes one or more springs which provide compressive forces for stabilization, and adjustment means 144 is a screw driven assembly to adjust the forces exerted by the springs. In yet another preferred embodiment, device 100 includes one or more pneumatic or hydraulic assemblies and adjustment means 144 is a screw driven assembly to adjust those assemblies.

Functional element 145 can provide functions that enhance therapeutic benefit and/or reduce complications and adverse side effects. In a preferred embodiment, functional element 145 comprises one or more flexible joints and provides dynamic stabilization to mimic a health joint such as a vertebral segment. In another preferred embodiment, functional element 145 comprises an artificial facet or partial facet, and serves the function of replacing or supporting a facet of a patient's vertebral segment. In yet another preferred embodiment, functional element 145 provides a function selected from the group consisting of: single axis flexion; multi-axis flexion; force translation such as providing a force to hinder motion in or more directions; motion limiting such as limiting a maximum relative motion between the first location and the second location; agent delivery such as anti-bone proliferation drugs; radiation delivery percutaneous access; facet replacement; facet enhancement; and combinations thereof. In yet another preferred embodiment, functional element 145 provides multiple functions such as those described above. Drug delivery or radiation exposure might be advantageous to limit the body's reaction to the surgery and/or the implant, such as bone proliferation which may limit joint movement that has been dynamically stabilized. Drug delivery, such as a coating on one or more components of device 100, or an eluding drug depot such as a refillable drug depot integral to functional assembly 145 or another component, may alternatively or additionally be used to deliver an agent such as an anti-biotic delivered to prevent infections not uncommon to implants and implant procedures. In another preferred embodiment, functional element 145 is a flexible band, such as a band that provides a tensioning force between the two bone locations to be stabilized. In another preferred embodiment, the band is included to provide a ligament function. In yet another preferred embodiment, functional element 145 provides multiple functions, such as two or more functions selected from the numerous functions described immediately hereabove.

In another preferred embodiment, device 100 includes a valve assembly, such as a valve assembly integral to adjustment means 144. The valve assembly can be used to provide one-way fluid access to one or more components of device 100, such as to refill a drug depot, adjust a hydraulic or pneumatic assembly, or other valve function. In an alternative embodiment, a valve is included which opens at a pre-determined pressure, such as a pressure relief valve which opens to prevent undesirable forces from being generated by device 100.

Referring now to FIG. 9A, a bone stabilization device of the present invention is depicted with a functional element configured to provide dynamic stabilization. Hinged assembly 120 includes axle 122, a pin projecting from pivoting arm 140 that is captured and rotatably received a receiving hole in screw head 125 to form a single degree of freedom hinge. Pivoting arm 140, shown secured with set screws to cradle 170 of receiving assembly 150, includes a functional element along its length, torsion-compression spring 146*a* that is configured to provide appropriate torsion and compressive forces for dynamic stabilization of two bone structures.

Referring now to FIG. 9B, another preferred hinge assembly of the present invention is depicted. Hinge assembly 120 includes hinge 130, of similar construction to the hinge of FIG. 9*a*, and pivoting arm 140, which includes a functional element, compression spring 146*b* along its length. Compression spring 146*b* is configured to provide appropriate forces for dynamic stabilization of two bone structures when Hinge assembly 120 and pivoting arm 140 are securedly attached to a receiving assembly of the present invention.

Referring now to FIG. 9C, device 100, consisting of the hinge assembly 120 of FIG. 9B, is shown secured to vertebra 4 of a patient. Also implanted is receiving assembly 150 shown secured to vertebra 2 of the patient. Pivoting arm 140 is shown in various rotational positions, rotating clockwise, as shown, until fully engaged with cradle 170. Pivoting arm 140 includes compression spring 146*b* along its length to provide dynamic stabilization between vertebra 4 and vertebra 2 of the patient.

Figure 10A:
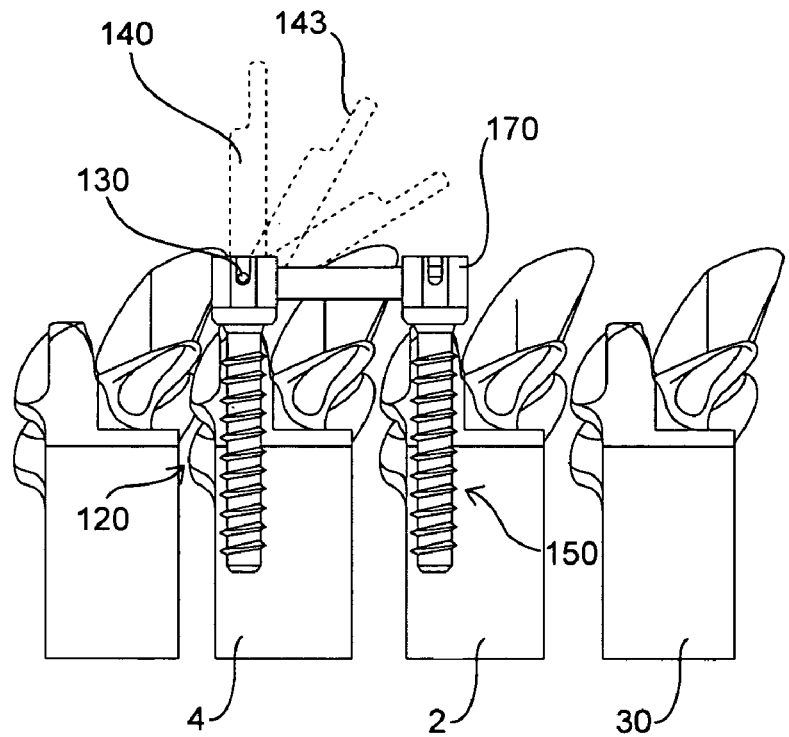
FIGS. 10A, 10B and 10C show side sectional views of a stabilization method consistent with the present invention in which multiple vertebral segments are stabilized.
Figure 10B:
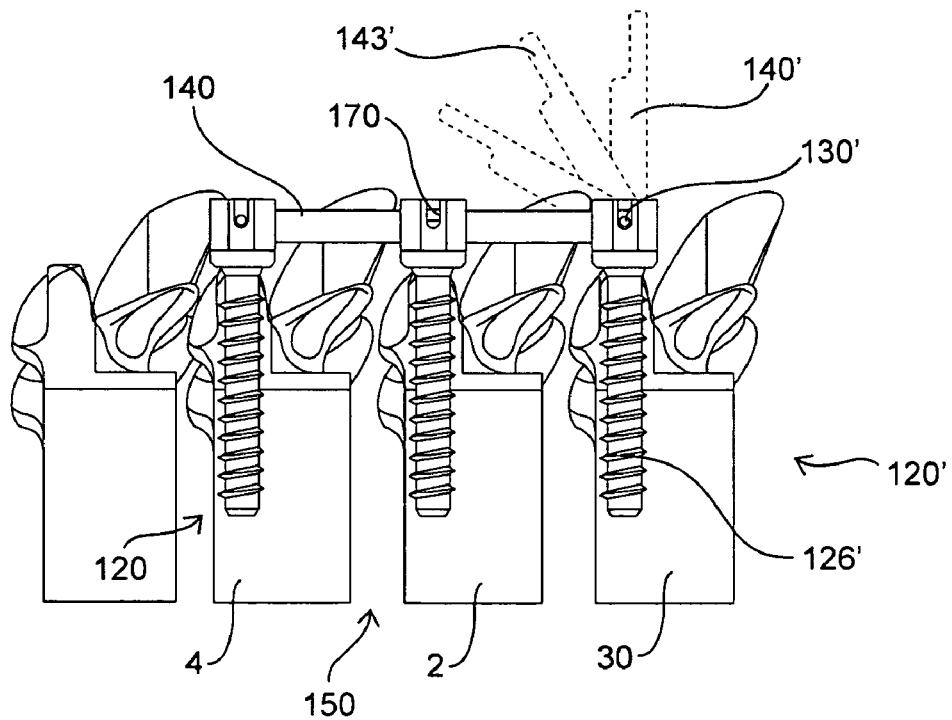
Figure 10C:
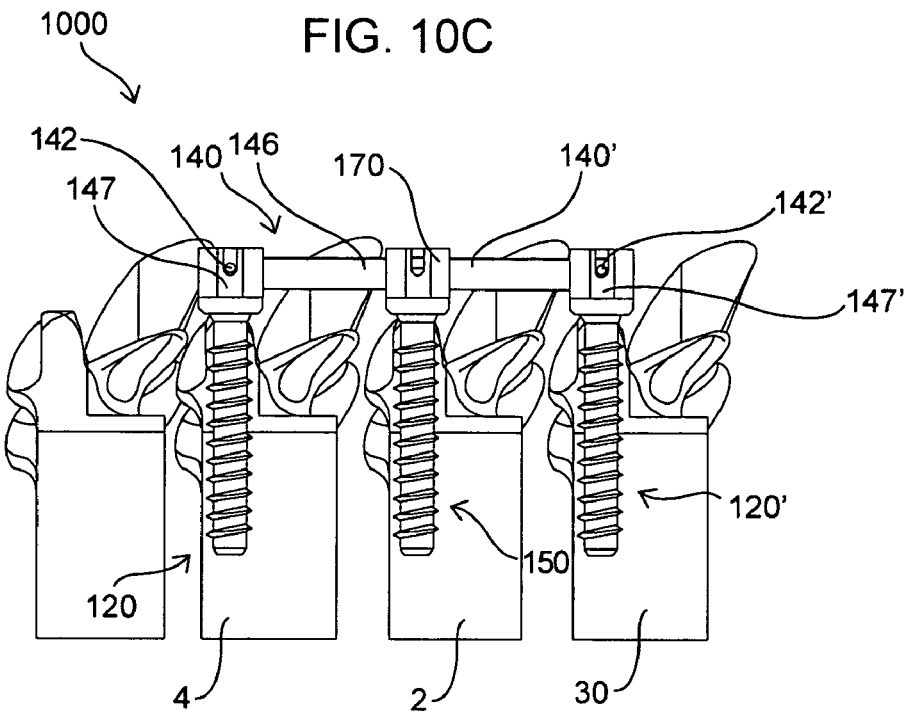

Referring now to FIGS. 10A, 10B and 10C, another preferred device and method of the present invention is illustrated in which three vertebral segments are stabilized relative to each other. Referring specifically to FIG. 10A, a hinged assembly 120 has been securely attached to vertebra 4 and a receiving assembly 150 has been securely attached to adjacent vertebra 2, such as by using similar percutaneous tools and techniques described in reference to FIGS. 6A through 6H. Pivoting arm 140 is being rotated in a clockwise direction, as shown, via hinge 130, to a location in which it's distal end resides within cradle 170 of receiving assembly 150. In the preferred embodiment of FIGS. 10A and 10B, the distal end of pivoting arm 140 includes a reduced segment, recess 143, which is configured to geometrically mate with an end portion of a separate pivoting arm. Referring now to FIG. 10B, a second hinged assembly, hinged assembly 120' has been inserted into a vertebra 30, a vertebra adjacent to vertebra 2 but opposite the side adjacent to vertebra 4, such as by using similar percutaneous tools and techniques described in reference to FIGS. 6A through 6H. Hinged assembly 120' is shown with its pivoting arm 140' being rotated in a counter-clockwise direction, as shown, via hinge 130' to a location in which it's distal ends also resides within cradle 170 of receiving assembly 150. The distal end of pivoting arm 140' also includes a reduced segment, recess 143', which is configured to geometrically mate with the end portion of recess 143 of pivoting arm 140 of hinged assembly 120.

Referring now specifically to FIG. 10C, poly-segment (more than two segments) bone stabilization device 1000 includes first hinged assembly 120, second hinged assembly 120' and receiving assembly 150. Receiving assembly 150 has slidingly receiving and is not securely attached to the distal ends of pivoting arm 140 and pivoting arm 140' or hinged assembly 120 and hinged assembly 120' respectively. Stabilization, such as dynamic stabilization or fixed stabilization, has been achieved between vertebra 4 and vertebra 2 and vertebra 30. The numerous enhancements, such as functional elements including one or more spring included in a pivoting arm, or other enhancements, can be included in first hinged assembly 120, second hinged assembly 120' and/or receiving assembly 150 to provide more therapeutic benefit, improve safety and/or longevity of the implanted device.

The distal ends of the pivoting arms 140 and 140' each have a reduced segment such that the combined cross-sections is relatively equivalent to the cross-section of either arm prior to the reduction. This mating portion allows a similar cradle 170 to be used that would be used to securedly engage a single pivoting arm without a reduced segment. Various geometries of the reduced cross sections can be employed. In a preferred embodiment, a fixation means, such as a set screw, not shown, is placed through each reduced portion and into cradle 170 to secure both pivoting arms to the receiving assembly.

Figure 11A:
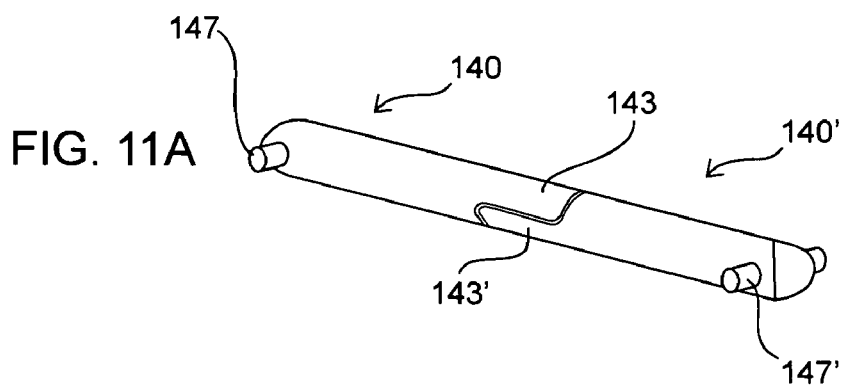
FIGS. 11A and 11B illustrate perspective views of pairs of pivoting arms consistent with the present invention, shown with "stacked" and "side-by-side" configurations, respectively, for poly-segment (more than two segment) bone stabilization.
Figure 11B:
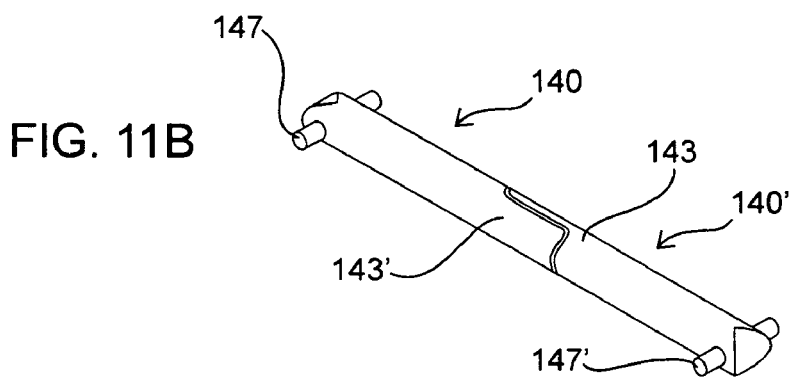

Referring now to FIGS. 11A and 11B, two preferred geometries of the reduced portions of FIGS. 10A through 10C are illustrated. A pair of pivoting arms is shown, pivoting arm 140 and pivoting arm 140'. On each proximal end, a pin, axle 147 and axle 147' extends radially out from the tubular structure, each pin configured to rotate in a bushing of the appropriate hinge assembly to perform a hinge function. FIG. 11A represents a geometry including two half-circular cross sections that are stacked on top of each other, when engaged, as viewed from the top of the cradle (looking down on the anchoring means). FIG. 11B represents a geometry also consisting of two half-circular cross sections, these sections aligned in a side-by-side orientation as viewed from the top of the cradle.

Figure 12A:
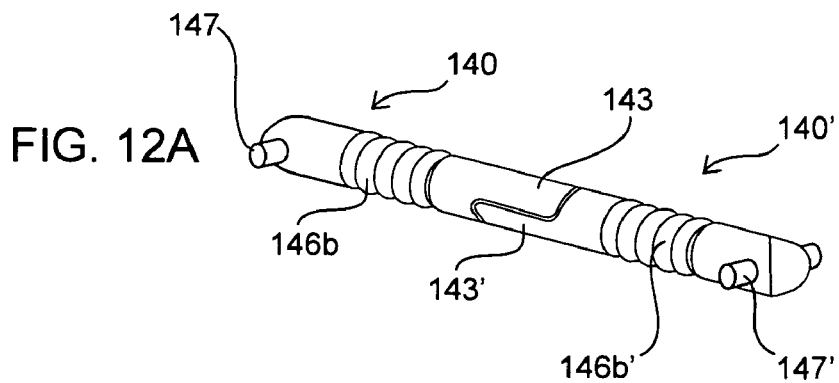
FIGS. 12A and 12B illustrate perspective views of pairs of pivoting arms consistent with the present invention, shown with "stacked" and "side-by-side" configurations, respectively, for poly-segment bone stabilization, wherein each pivoting arm includes an integral coiled spring.
Figure 12B:
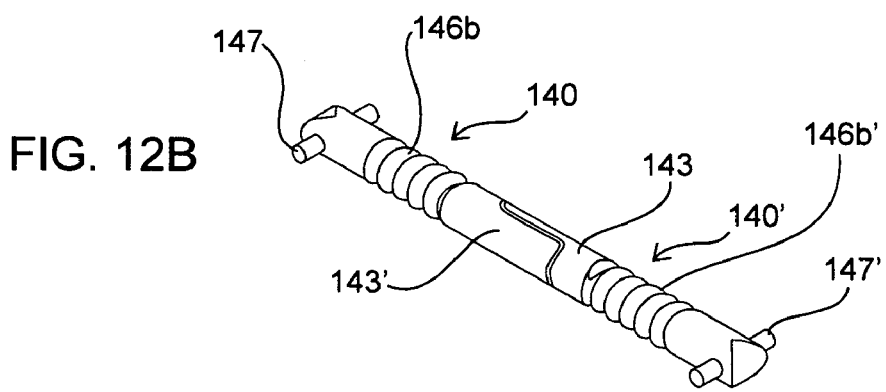
Figure 13:
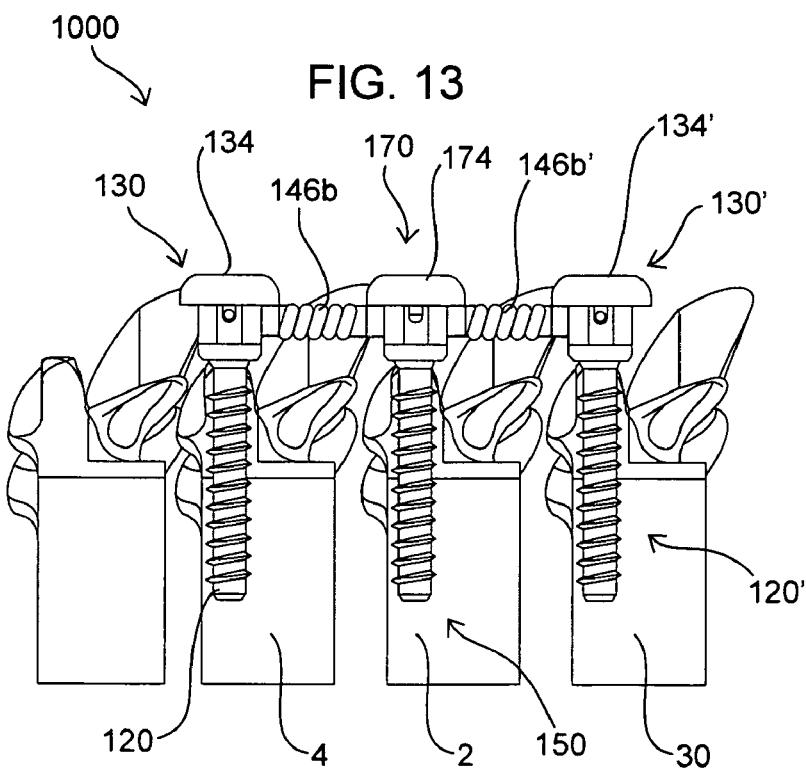
FIG. 13 illustrates a side sectional view of a poly-segment bone stabilization system consistent with the present invention, in which the pivoting arm pair of FIGS. 12a or 12b has been secured to vertebrae and engaged at their midpoint with a receiving assembly, also secured to a vertebra.

Referring now to FIGS. 12A and 12B, two additional preferred geometries of pairs of pivoting arms are illustrated. The cross sectional geometries of pivoting arms 140 and 140' are the same as those of arms 140 and 140' of FIGS. 11A and 11B respectively. The pivoting arms of FIGS. 12A and 12B further each include a functional element, coil springs 146b and 146b', along their length, to provide dynamic stabilization forces when a poly-segment stabilization device of the present invention is implanted. Referring now to FIG. 13, poly-segment bone stabilization device 1000 includes first hinged assembly 120 and second hinged assembly 120' which include the pivoting arms 140 and 140' of FIGS. 12A and/or 12B. In the preferred embodiment of FIG. 13, multiple caps are placed on engagable portions of components of device 1000, such as cap 134 placed on top of the hinge of hinged assembly 120, cap 174 placed on top of cradle 170 of receiving assembly 150, and cap 134' placed on top of the hinge of hinged assembly 120'. These caps are made of a biocompatible metal or plastic, and prevent tissue in-growth and other contamination from entering engagement means such as slots and other engagable surfaces. The caps are preferably a pressure fit or screw cap, and can be easily removed with minimally invasive means. In an alternative embodiment, one or more of the caps are biodegradable.

Figure 14A:
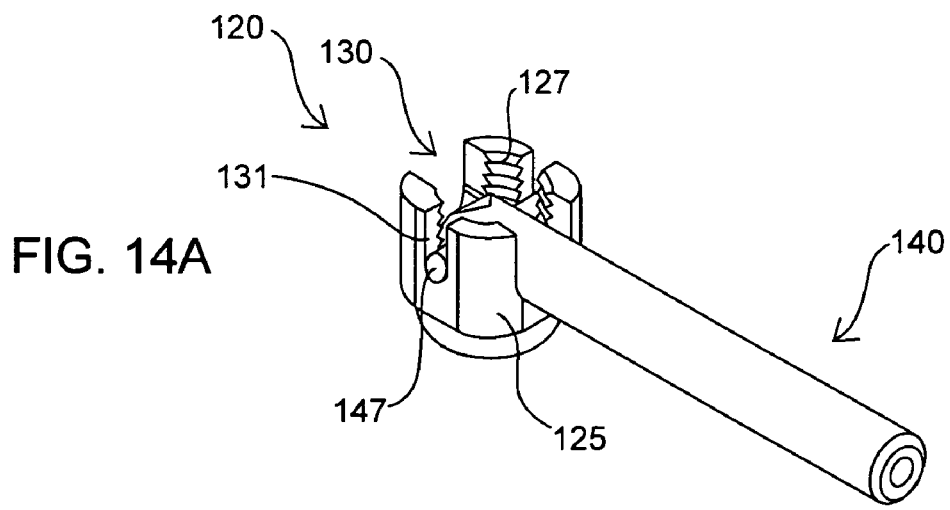
FIGS. 14A, 14B and 14C illustrate hinged assemblies consistent with the present invention including, respectively, a pivoting arm with "snap-in" axle, a pivoting arm with a captured axle, and a pivoting arm with a flexible segment.
Figure 14B:
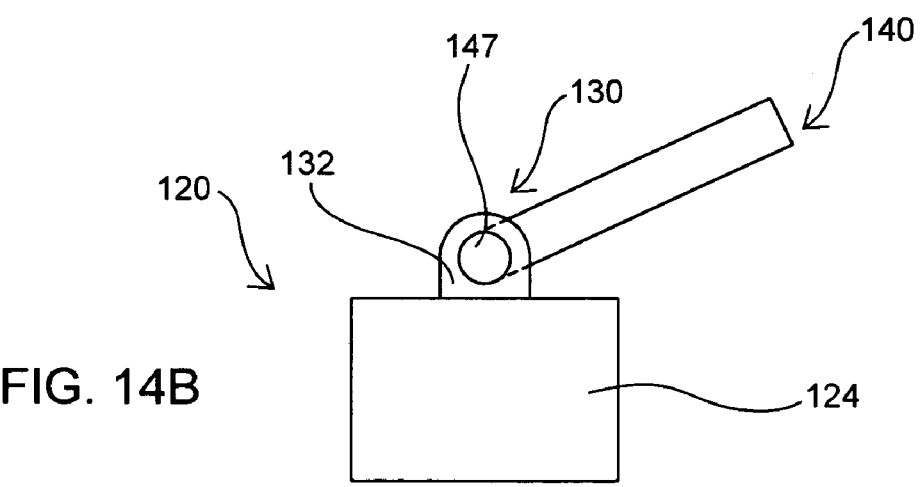
Figure 14C:
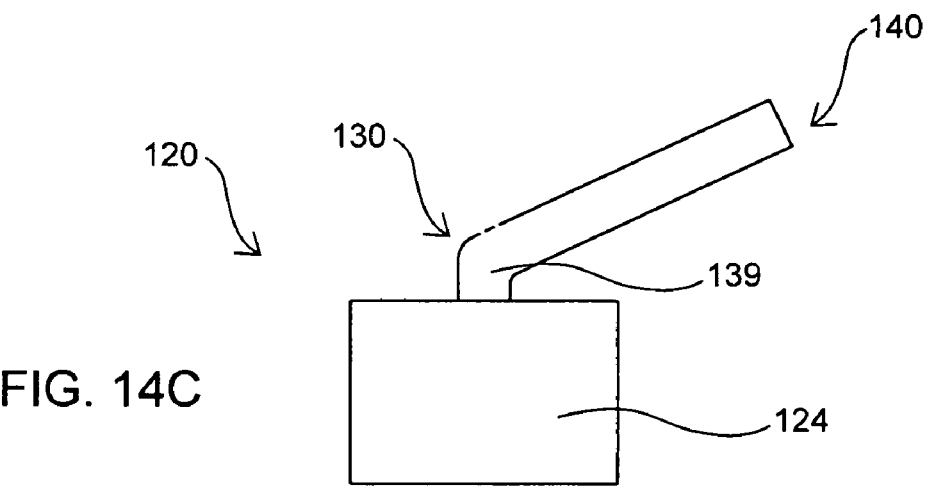

Referring now to FIGS. 14A, 14B and 14C, hinge mechanisms of the hinged assemblies of the present invention are illustrated. Referring specifically to FIG. 14A, an operator assembled hinge is illustrated. Hinge 130 includes a projecting pin, axle 147, that extends from pivoting arm 140. Axle 147 is configured to be snapped in place into slot 131 of screw head 125. Screw head 125 is fixedly or rotatably connected to an anchoring portion of hinge assembly 120, anchor portion not shown. Screw head 125 further includes threads 127, which are configured to accept a set screw to prevent inadvertent disassembly of hinge 130. Threads 127 can also be used to lock-down, or otherwise prevent rotation of arm 140. A set can be partially inserted to capture the pin yet allow rotation, such as prior to implantation in the patient, or a set screw can be inserted after insertion into the body of the patient.

Referring specifically to FIG. 14B, another preferred embodiment of a hinge of the present invention is illustrated. Hinged assembly 120 includes pivoting arm 140, which is pivotally attached to base 124 via hinge 130. Pivoting arm 140 includes a projecting pin 147, which is permanently captured by a bushing included in housing 132. Pivoting arm 140 can be fixed in place by one or more mechanisms described in detail throughout this application.

Referring specifically to FIG. 14C, an alternative embodiment of a hinge is provided in which a portion of pivoting arm 140 includes a flexible portion, such as two metal rods connected with a elastic or otherwise deformable section. Pivoting arm 140 is fixedly mounted to base 124, and hinge 130 consists of flex point 139 of arm 140. Pivoting arm 140 and flex point 139 may be resiliently biased, either in the final secured position, or starting (linearly aligned with the anchor portion) position, or a position in between. Alternatively, pivoting arm 140 may be plastically deformable, changing its biased position as it is rotated.

Figure 15A:
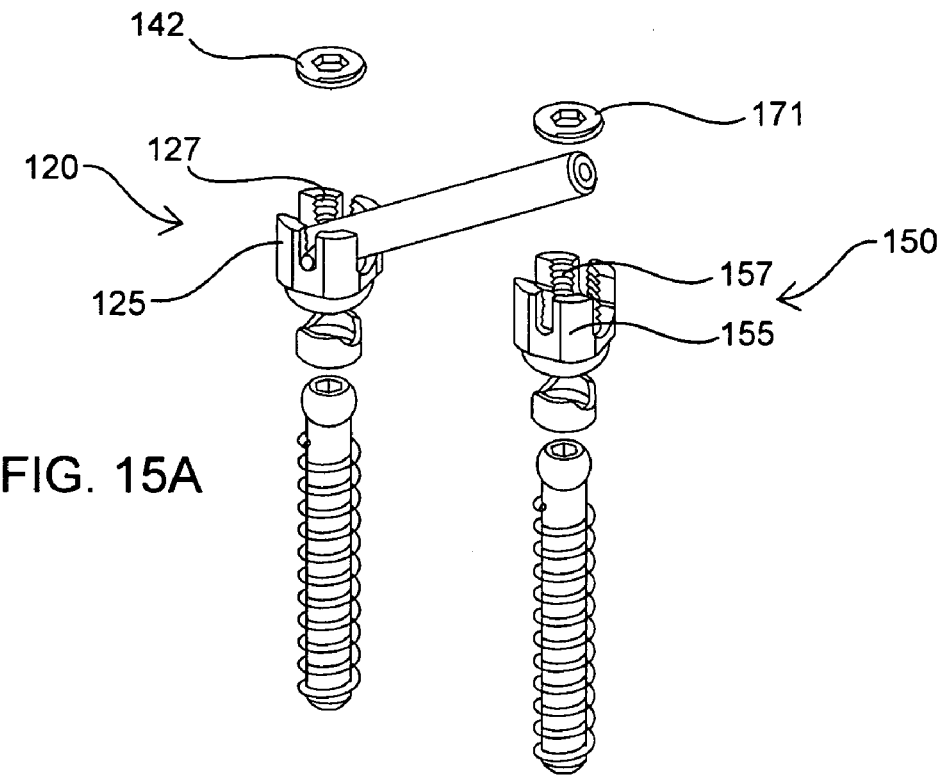
FIGS. 15A and 15B illustrates perspective views of bone stabilization devices consistent with the present invention wherein additional set screws are placed to secure the pivoting arm.
Figure 15B:
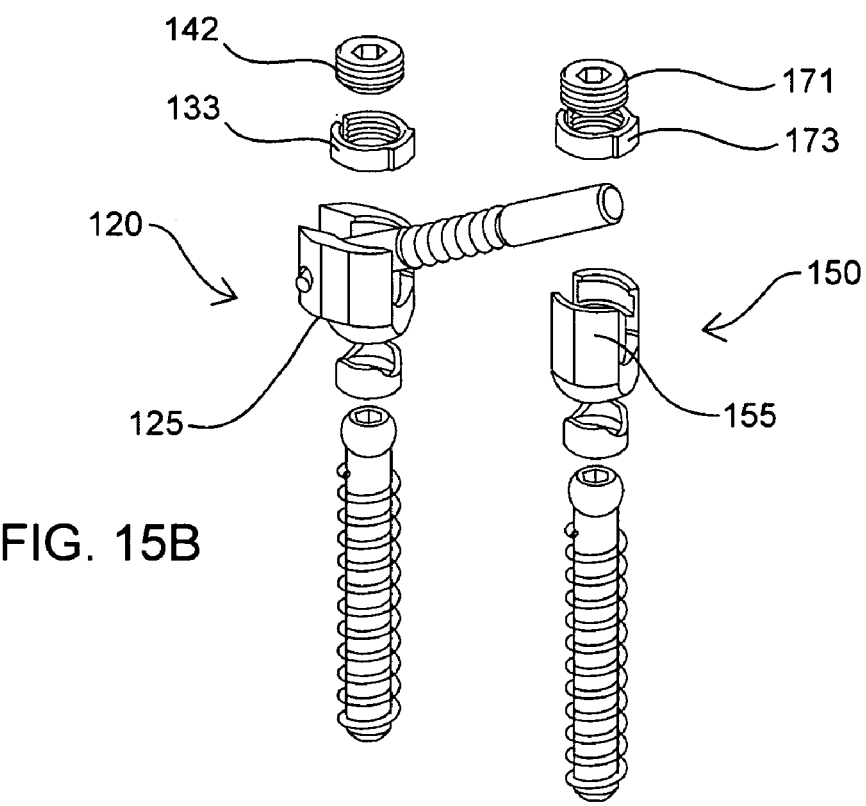

Referring now to FIGS. 15A and 15B, means of securing the pivoting arm of the present invention are illustrated. FIG. 15A illustrates sets screws 142 and 171, configured to be operatively engaged with threads 127 and 157 respectively. Threads 127 are integral to screw head 125 of hinged assembly 120 and threads 157 are integral to screw head 155 of receiving assembly 150. Both screw 142 and 171 include a thru-lumen, which allows over-the-wire insertion, such as insertion performed by an operator using an over-the-wire screwdriver of the present invention. Referring now to FIG. 15B, an alternative securing means is illustrated, including a two-piece assembly comprising a screw and an expandable ring. Ring 133 is inserted to screw head 125 of hinge assembly 120 after which screw 142 is rotatably engaged with ring 133, causing ring 133 to radially expand and provide a high compression, reliable connection. Similarly, ring 173 is inserted into screw head 155 of receiving assembly 150 after which screw 171 is rotatably engaged with the threads of ring 173, causing ring 173 to radially expand and provide high compression, reliable connection.

Referring now to FIG. 16, a method of accessing a bone stabilization device is illustrated. Two cannula, cannula 220a and 200b are shown as having been inserted through the patient's skin 80 at locations directly above vertebra 4 and vertebra 2 respectively. A poly-segment hinged assembly device 1000 of the present invention has been planted at an earlier date, such as a time period of months or more earlier. Device 1000 is configured to stabilize vertebra 4, vertebra 2 and vertebra 30 in a fixed or fused configuration, or in a dynamically stabilized configuration. Device 1000 includes a first hinged assembly 120 securely attached to vertebra 4, a receiving assembly 150 securely attached to vertebra 2 and a second hinged assembly 120 securely attached to vertebra 30. Pivoting arm 140' of hinged assembly 120' is shown in secure attachment with cradle 170 of receiving assembly 150. Hinge 130' is covered with cap 134' attached during the original implantation procedure of device 1000. Caps that were originally attached in the original implantation procedure, such as a cap on hinge assembly 130 and cradle 170 have been removed in the accessing procedure of FIG. 16. Percutaneous grasping and ply tools, as well as percutaneous rotational tools such as screwdrivers are preferably used to detach these caps and extract through either cannula 220a or 220b.

The method depicted in FIG. 16 involves the unsecuring of pivot arm 140, already completed, and the reverse rotation of pivot arm 140, depicted as partially rotated by using lifting tool 233 inserted through cannula 220b. Screwdriver 232 has been inserted through cannula 220a and used to loosen and/or remove engagement means such that pivoting arm 140 can rotate, engagement means already removed and not shown. Subsequent steps may include the complete removal of hinge assembly 120, and reinsertion of a new hinged assembly, such as when hinged assembly 120 is damaged or when a hinged assembly with different properties, such as a differently configured pivoting arm 140 is desirable. In an alternative embodiment, hinge 120 is adjusted, and pivoting arm 140 again secured to cradle 170. Numerous combinations of adjustments and replacements of one or more components of system 1000 can be accomplished utilizing the percutaneous tools and methods depicted in FIG. 16. Use of one or more caps, such as cap 134', make subsequent engagement of tools with system 1000 components easier to accomplish since the covered surfaces are free from material that would compromise engagement.

Figure 17:
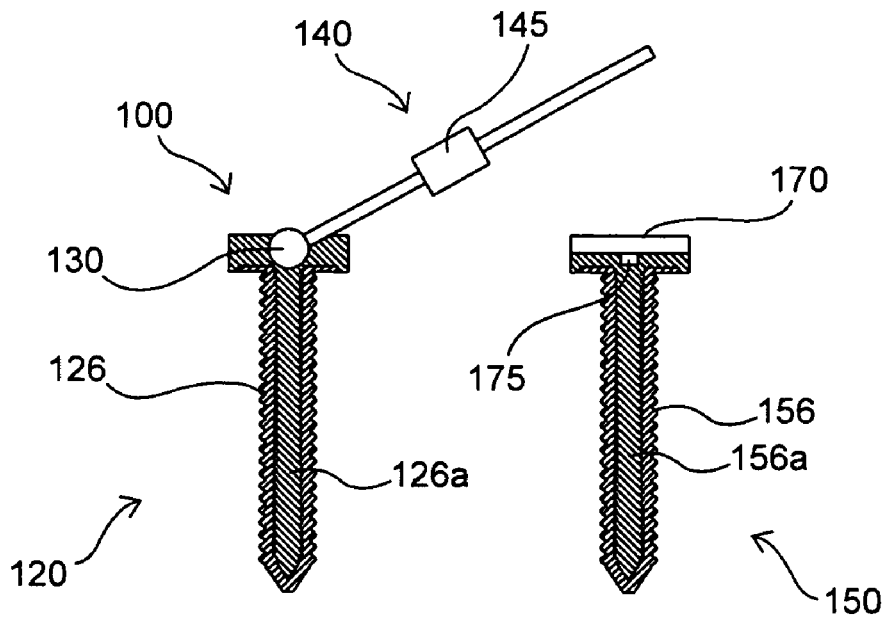
FIG. 17 illustrates a side sectional view of a bone stabilization device consistent with the present invention in which each bone anchor includes a removable and/or replaceable threaded core and the pivoting arm includes a functional element.

Referring now to FIG. 17, another preferred embodiment of bone stabilization device of the present invention is illustrated wherein anchor portions consist of an outer tube and a removable core. Device 100 includes hinged assembly 120 including a bone anchor and pivoting arm 140 which attaches to the bone anchor portion via hinge 130. Pivoting arm 140 includes function element 145, such as a spring or other flexible element that provides a flexion point for dynamic stabilization of two bone structures. Device 100 further includes receiving assembly 150 which includes a bone anchor portion which is attached to surface 170. Surface 170 is configured to securely attach to the distal end of pivoting arm such as via a screw, not shown, but preferably inserted through the distal end of arm 140 and into threads 175. Both the hinged assembly 120 and receiving assembly 150 include anchor portions which have external threads for engaging and securing in bone, and a removable inner core, configured to be removed via one or more means such as the threaded engagement depicted in FIG. 17. Internal threads 126a and internal threads 156a of the hinged assembly and receiving assembly anchor portions respectively, allow the remaining portion of these assemblies to be removed, such as after a period of implantation, while leaving the outer threaded portions in place, such as for insertion of a subsequent assembly or otherwise.

Figure 18:
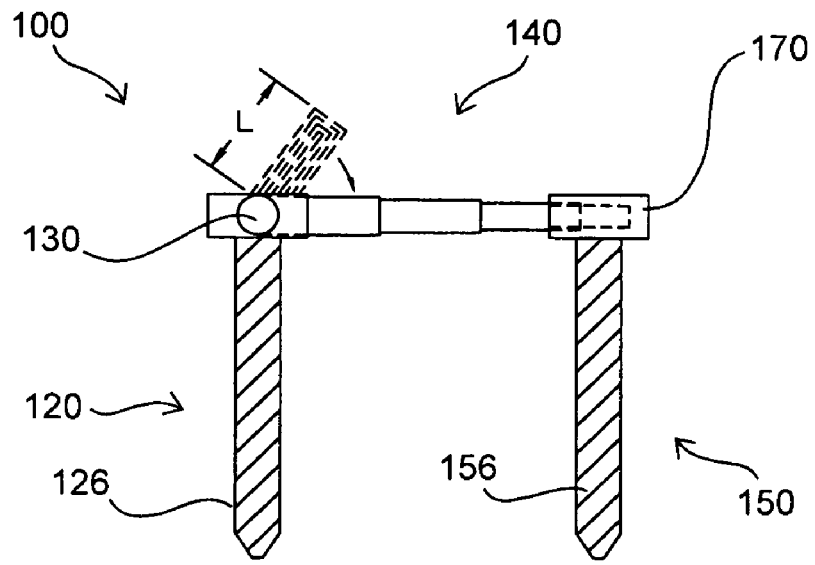
FIG. 18 illustrates a side view of a bone stabilization device consistent with the present invention in which the pivoting arm comprises a telescoping assembly such that the radius of the arc during rotation of the pivoting arm is greatly reduced.

Referring now to FIG. 18, another preferred embodiment of the bone stabilization device of the present invention is illustrated wherein the pivoting arm can be telescopically extended or retracted, such as to rotate with a minimal radius of curvature. Device 100 includes hinged assembly 120 including a bone anchor and pivoting arm 140 which attaches to the bone anchor portion via hinge 130. Device 100 further includes receiving assembly 150 which includes a bone anchor portion which is attached to cradle 170. Cradle 170 is configured to securely attach to the distal end of pivoting arm such as by the various engagement means described throughout this application. Both hinged assembly 120 and receiving assembly 150 include anchor portions which have external threads for engaging and securing in bone, external threads 126 and 156 respectively. Pivoting arm 140 consists of a series of interlocking slidable tubes configured to telescopically be advanced, such as to be long enough to engage with cradle 170. In a preferred embodiment, hinged assembly 120 is percutaneously inserted into the body, and pivoting arm 140, in a telescopically retracted state, is pivoted an amount such that its axis is pointing at the engagement portion of cradle 170, such as a ninety degree rotation in the configuration shown. Subsequently, using a push tool, an integral extending assembly such as a hydraulic or pneumatic extending assembly, or other means, the distal end of an inner, such as the innermost, telescopic section is advanced until properly seated for engagement in cradle 170. The telescoping tubes of pivoting arm 170 are preferably made of a rigid metal, sufficient to provide sufficient force to achieve the desired stabilization.

Figure 19:
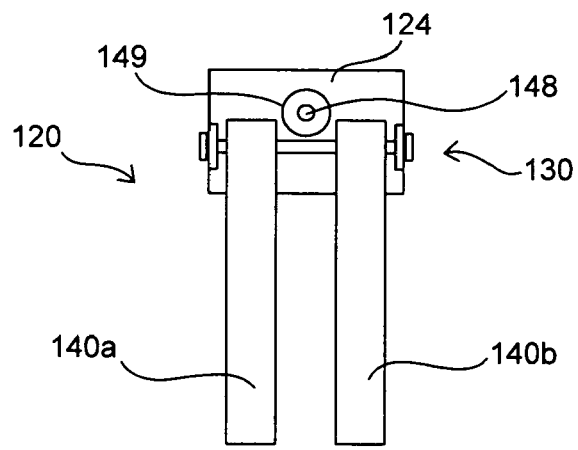
FIG. 19 illustrates a top view of a hinged assembly consistent with the present invention in which the hinged assembly comprises multiple pivoting arms.
Figure 19A:
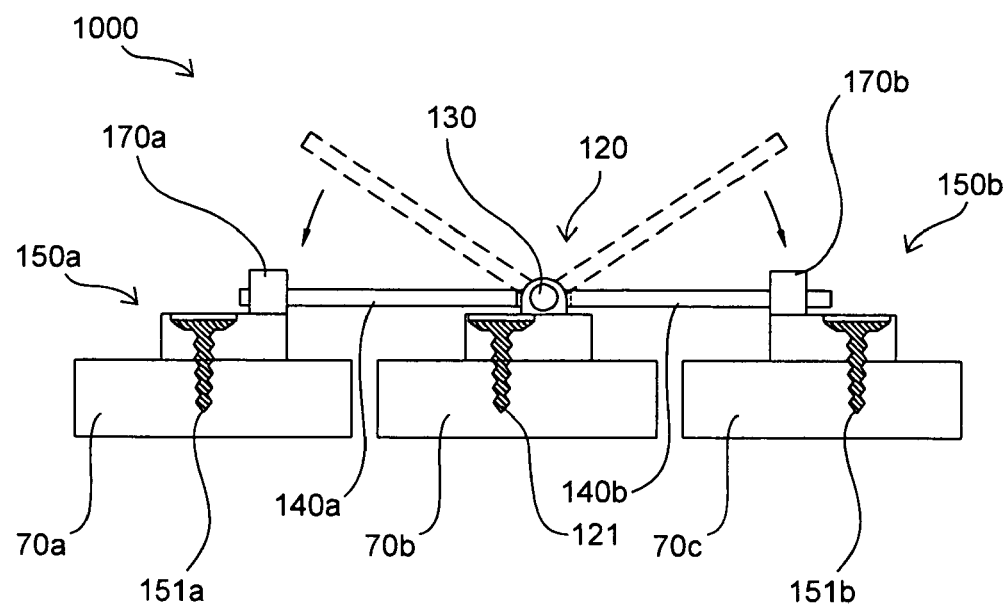
FIG. 19A illustrates a side sectional view of a bone stabilization device of the present invention in which the hinged assembly of FIG. 19 is anchored to a bone segment, and the first pivoting arm rotates to a first receiving assembly and the second pivoting arm rotates to a second receiving assembly.

Referring now to FIG. 19, a preferred embodiment of the hinged assembly of the present invention is illustrated wherein multiple pivoting arms are included. Hinged assembly 120 includes thru lumen 148, such as a lumen for a guidewire and/or bone screw, and recess 149 which can accommodate the screw head of such a bone screw. Hinged assembly 120 further includes hinge 130, which rotatably attaches base 124 to two pivoting arms, 140a and 140b. In an alternative embodiment, more than two pivoting arms are rotatably attached by hinge 130. These multiple arms can be used to stabilize the particular bone segment to which hinged assembly 120 is attached to a single additional bone segment, or multiple bone segments wherein each arm is connected by an operator to a component on the different bone segments. Referring now to FIG. 19a, a preferred configuration of a poly-segment stabilization device 1000 and attachment method is illustrated. Device 1000 includes the dual arm hinged assembly 120 of FIG. 19, and two receiving assemblies 150a and 150b. Hinged assembly 120 is securely attached via screw 121 to second bone segment 70b, such as a fractured bone in the patient's arm or leg, or a vertebra of the patient's spine. Receiving assembly 150a is securely attached to bone segment 70a with screw 151a and receiving assembly 150b is securely attached to bone segment 70c with screw 151b, the three bone segments aligned as shown. Hinged assembly 120, preferably inserted in the over-the-wire percutaneous technique described in reference to FIGS. 6a through 6h, such as wherein one or none of the pivoting arms includes a thru lumen for advancement of the percutaneous guidewire. As shown, pivoting arm 140a is rotated such that it can be securely engaged with cradle 170a of receiving assembly 150b and pivoting arm 140b is rotated such that it can be securely engaged with cradle 170b of receiving assembly 150b. Upon dual engagement of each pivoting arm, fixed or dynamic stabilization is achieved between the three bone segments, 70a, 70b and 70c. Additional dual arm and single arm hinged assemblies, as well as dual or single cradle receiving assemblies, can be added, in the linear arrangement shown, and/or with hinged assemblies and/or receiving assemblies placed in a side-by-side configuration. These poly-component (more than 2) devices and methods can be useful in treating complex bone fractures and other poly-location stabilization procedures. In an alternative embodiment, the multiple arms of the hinged assembly have different lengths, such as to securedly engage with components separated from the hinged assembly by different displacements. Each of the multiple arms can rotate to a single receiving assembly, or different receiving assemblies.

Figure 20:
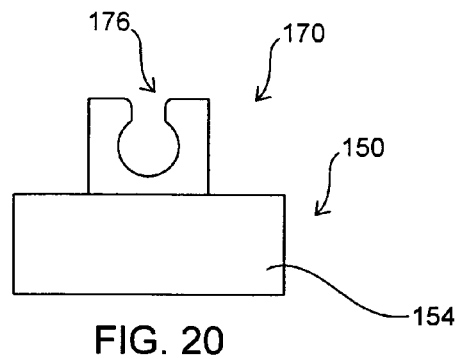
FIG. 20 illustrates an end view of receiving assembly consistent with the present invention in which the cradle includes a projection that is configured to capture a pivoting arm.
Figures 20A, 20B:
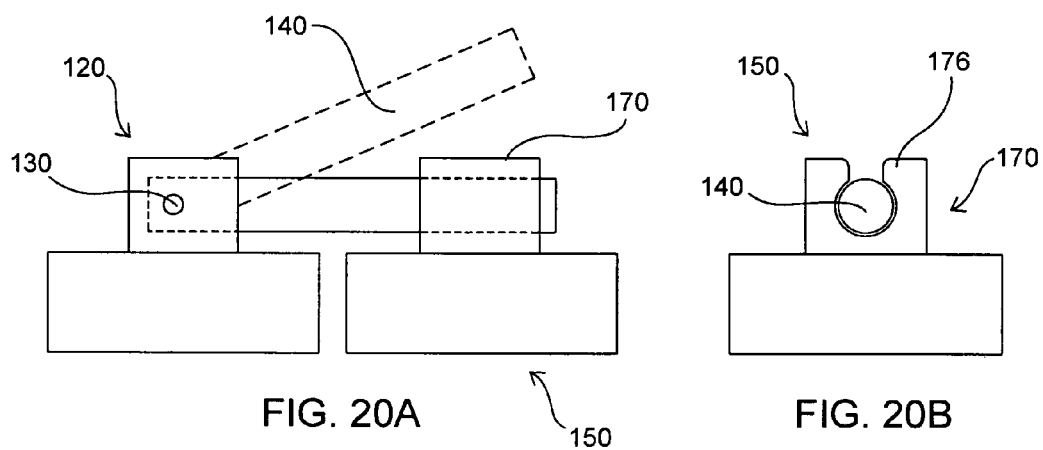
FIGS. 20A and 20B illustrate side and end views, respectively, of a bone stabilization device consistent with the present invention using the receiving assembly of FIG. 20 and shown with the pivoting arm captured by the cradle of the receiving assembly.

Referring now to FIGS. 20, 20A and 20B, a preferred embodiment of the present invention is illustrated wherein the receiving assembly automatically engages the pivoting arm of the hinged assembly. Referring specifically to FIG. 20, an end view of hinged assembly 150 is shown wherein cradle 170 is securedly mounted to plate 154, via fixed or movable engagement means. Cradle 170 includes a circular notch for maintaining a pivoting arm of the present invention, the diameter chosen to be slightly larger than the diameter of the appropriate pivoting arm. At the top of the notch is projection 176, wherein the size of notch 176 and the materials of construction of cradle 170 are chosen such that the distal end of a pivoting arm can snap into place, being maintain in place by projection 176 under certain load conditions. In a preferred embodiment, the forces are chosen such that no additional securing means are required to achieve the desired therapeutic function (stabilization of bone structures). In an alternative, also preferred embodiment, an additional securing function is included, such as the retraining set screws described throughout this application. Referring to FIG. 20A, pivoting arm 140 of hinged assembly 120 is shown rotating in a clockwise direction about hinge 130. Receiving assembly 150, of FIG. 20, is included and provides a snap-fit function that retains the distal end of arm 140 when full rotated to be constrained within cradle 170 as shown in FIG. 20B.

Figure 21:
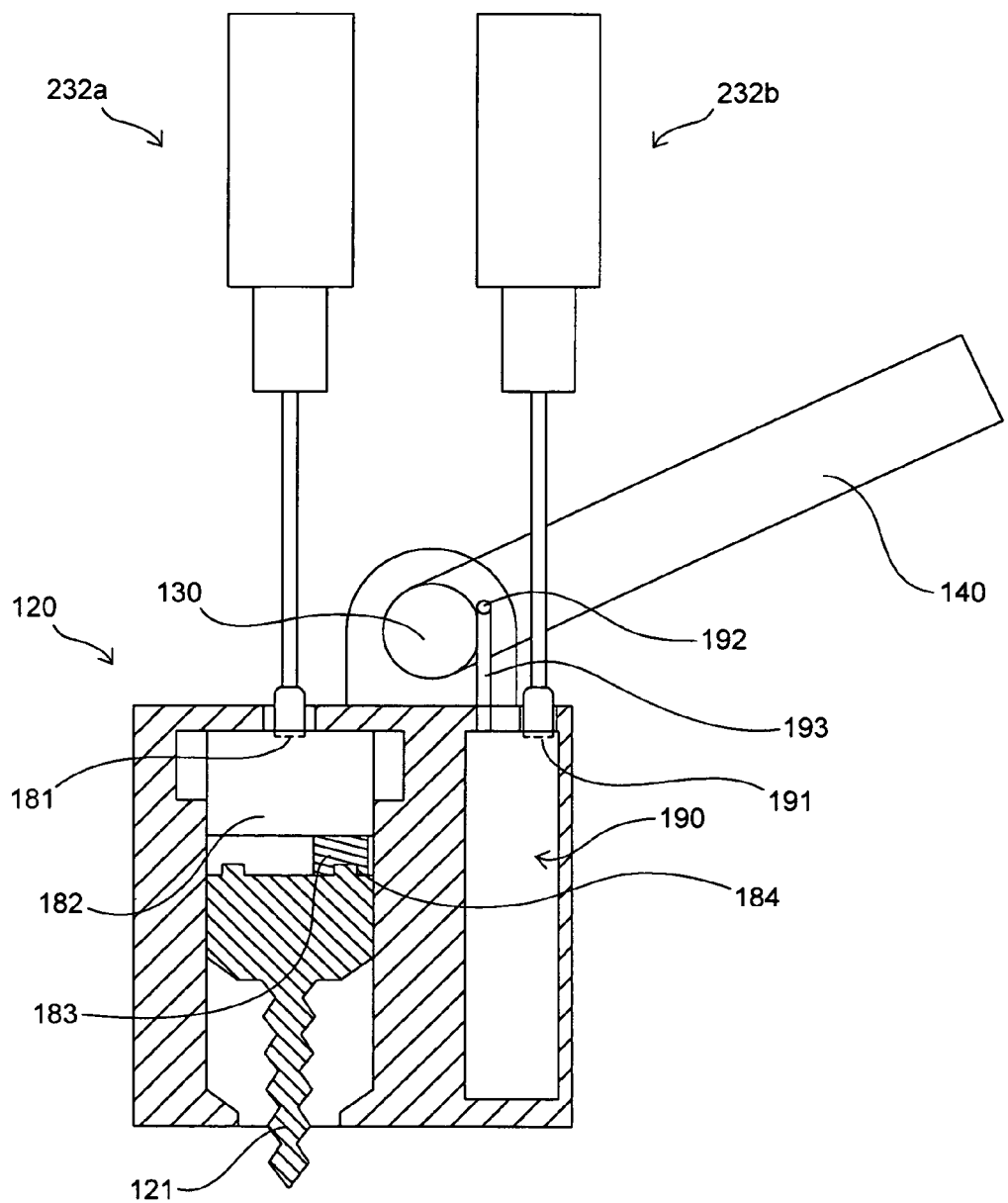
FIG. 21 illustrates a side sectional view of a hinged assembly consistent with the present invention in which two mechanical advantage elements are integral to the hinged assembly.

Referring now to FIG. 21, a preferred embodiment of the hinged assembly of the present invention is illustrated wherein assemblies are included that provide a mechanical advantage to perform one or more functions, such as functions performed during or post implantation. Hinged assembly 120 includes pivoting arm 140, which is rotatably attached to hinge 130. Pivoting arm 140 is also rotatably attached to piston 193 via pin 192. Piston 193 is a hydraulically or pneumatically driven piston of piston assembly 190. Piston assembly 190 includes engagable activation means 191, shown in operable attachment to screwdriver 232b, such as a percutaneous screwdriver than can be advanced through a percutaneous cannula. Rotation of means 191 is used to advance and retract piston 193, which in turn causes pivoting arm 140 to rotate in counterclockwise and clockwise directions, respectively. Hydraulic and pneumatic assemblies can be used to generate large amounts of force, perform precise movements, and provide other mechanical advantages.

Hinged assembly 120 further includes another mechanical advantage assembly, a precision, high-torque screw advancement and/or screw retraction assembly including linear advancement element 182, rotational element 183, and engagement means 181. The screw advancement assembly is shown as engaged by percutaneous screwdriver 232a on its input end, and engages screw 121, preferably a screw configured for advancement into bone, such as a screw with polyaxial head pedicle screw construction. Linear advancement element 182 includes an expandable bellows construction, expandable via an internal gear train mechanism, not shown, such that as screwdriver 232a is engaged and rotated, the bottom surface of element 182 expands in the direction opposite the surface including hinge 130. Rotation element 182 is operably engaged with a circular array of teeth integral to screw 121, teeth 184. Rotation of screwdriver 232a when engaged with engagement means 181 causes both downward expansion of element 182, and rotation of screw 121 via rotational element 182's engagement with teeth 184. Configuration of the included gear train can provide numerous benefits, including but not limited to: high levels of torque; precise advancement and/or rotation of screw 121; and other advantages.

It should be appreciated that numerous forms and varied configurations of mechanical advantage assemblies can be incorporated, to provide one or more functions, especially to overcome the limitations imposed by small implantable assemblies that are preferably accessed with miniaturized tools. Hydraulic and pneumatic assemblies can be employed to generate large forces and provide other benefits. Gear trains and lever arm assemblies can be employed to create precision control of motion and also provide other benefits. These mechanical advantage assemblies of the present invention can be integrated into one or more components of the bone stabilization device, such as the hinged assembly, the receiving assembly, or a separate component also configured to be implanted. These mechanical advantage assemblies can perform numerous functions including but not limited to: rotation of the pivoting arm; extension such as telescopic extension of the pivoting arm such as a hydraulically advanced pivoting arm; rotation and/or longitudinal advancement of a bone anchoring component such as a bone screw, application of one or more forces to a bone segment, such as a variable force stabilizing function such as a shock absorber for two bone segments; and combinations thereof.

Figure 22A:
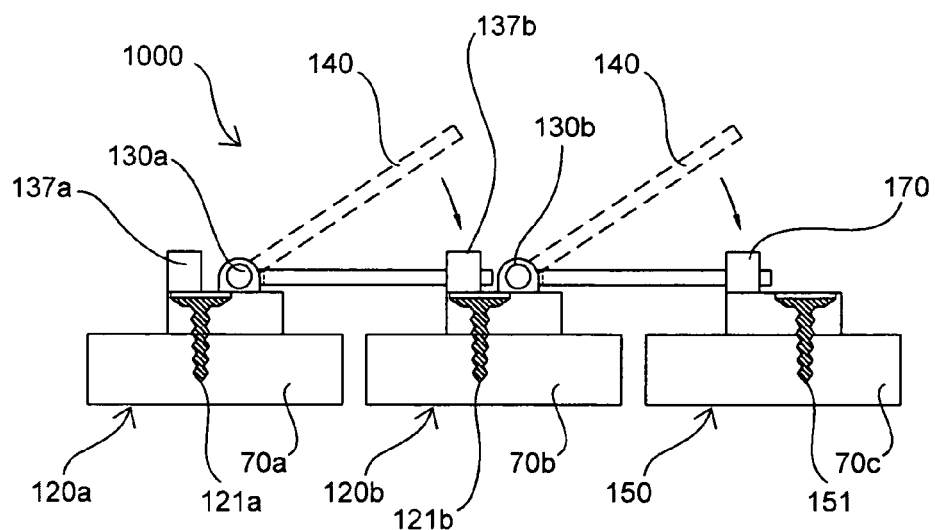
FIG. 22A and 22B illustrate side sectional and top views of a bone stabilization device of the present invention in which two hinged assemblies are secured to bone in an adjacent, connecting configuration with a receiving assembly secured at one end.
Figure 22B:
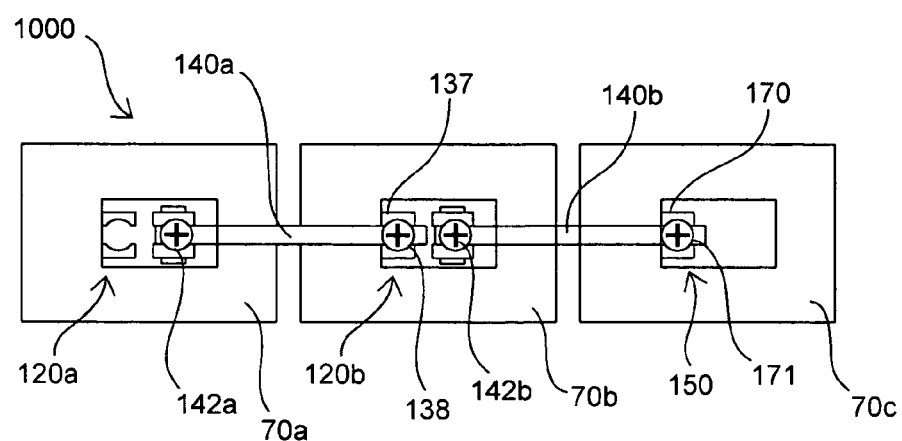
Figure 23:
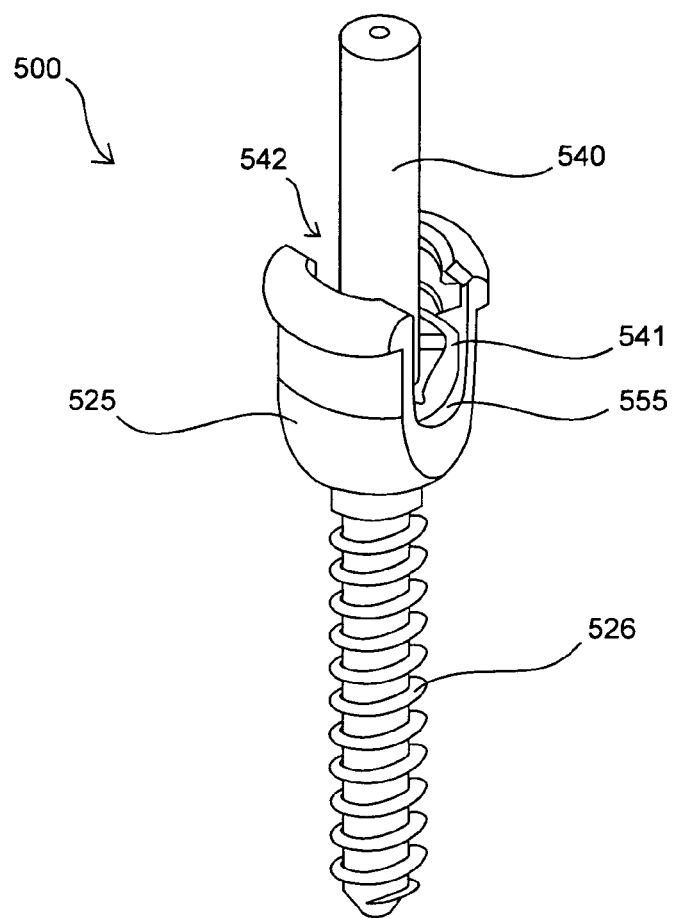
FIG. 23 illustrates a perspective view of a bone stabilization device according to an embodiment of the present invention in which a mechanism is provided for driving the screw despite the presence of the rod.

Referring now to FIGS. 22A and 22B, another poly-segment bone stabilization device and method of the present invention is illustrated, in which two hinged assemblies are implanted at adjacent locations, and at least one hinged assembly includes an attaching cradle for receiving a pivoting arm of the other hinged assembly. System 1000 includes first hinged assembly 120a securely attached to first bone segment 70a via attachment screw 121 a, second hinged assembly 120b attached to second bond segment 70b via attachment screw 121b, and receiving assembly 150 attached to third bone segment 70c via attachment screw 151. Bone segments 70a, 70b and 70c, such as three adjacent vertebra of a patient, receive device 1000 in order to provide stabilization between the segments. Both hinged assembly 120a and 120b include means of receiving a pivoting arm, the receiving means comprising cradles 137a and 137b respectively. In the figure shown, hinged assembly 120b receives, in cradle 137b, the pivot arm of hinged assembly 120a. Cradle 137a of hinged assembly 130a is implanted with no secured pivoting arm, an acceptable configuration especially as it would result in fewer variations of components (hinged assemblies with and without cradles).

The pivoting arm of hinged assembly 120b is received by cradle 170 of receiving assembly 150 as shown. Each of the receiving arms can provide fixed or dynamic stabilization, through inclusion of one or more flexing means as has been described in detail hereabove. In an alternative embodiment, a single component, a universal component consisting of a hinged assembly with a cradle, and a detachable (or attachable) pivoting arm, can be used, in multiplicity, to recreate the three-segment scenario depicted in FIGS. 22A and 22B, as well as any other two-segment or poly-segment stabilization scenario such as the other embodiments described hereabove. In a preferred embodiment, this universal component includes multiple types of pivoting arms, such as arms that provide different amounts and/or directions of stabilizing forces and or limit ranges of motions in varied distances and orientations.

It should be understood that numerous other configurations of the systems, devices and methods described herein may be employed without departing from the spirit or scope of this application. The pivoting arm of the stabilization device can be attached to bone anchors at its proximal, hinged end, and/or at its translating distal end, with a secured connection that is static (fixed), or it can be secured with a movable, dynamic connection. The pivoting arm and securing connections can be configured to prevent motion of the bone segments, limit motion such as limiting a specific direction or type of motion, or apply specific resistive forces to motion.

The components of the devices of the present invention are preferably configured for percutaneous placement, each device sized for placement through a percutaneous cannula. Each device preferably includes a lumen or sidecar through which a guidewire can be placed, or allowing placement along side a percutaneously placed guidewire. The pivoting arm of the present invention can preferably be rotated, such as with the inclusion of a slot allowing the guidewire to exit a lumen, while a guidewire is in place. The pivoting arm and attached components are preferably configured such that the pivoting arm can be secured, such as with insertion of multiple set screws, also with a guidewire in place. Other components may include slot exits from guidewire lumens such as to allow over-the-wire delivery and subsequently escape the guidewire while leaving the guidewire in place. The devices and methods of the present invention are configured to be inserted without resection of tissue, however procedures including or requiring resection are also supported.

The pivoting arm of the present invention preferably includes one or more functional elements. In a preferred embodiment, an artificial facet or facet portion is included and built into the pivoting arm or other component of the bone stabilization device. Each component may include one or more articulating surfaces, such as one located at the end of the pivoting arm and one on either the receiving assembly or hinged assembly of the present invention, such that pre-defined motion between the two attached bone segments can be achieved.

One difficulty occasionally associated with driving bone screws according to certain embodiments of the present invention is that the pre-assembly of the rod onto the head of the screw eliminates or severely limits the use of current driving mechanisms, as the head of the screw is generally rendered difficult to access or non-accessible.

Certain other embodiments of the invention address this difficulty. It should be noted that such embodiments may in particular refer to assemblies such as element 100 of FIG. 4, but that the same may also be employed in the receiving assembly of element 150.

Referring in particular to FIGS. 23-26, a device 500 includes a pivoting arm 540 and a bone anchoring portion including a seat 525. Seat 525 may be a polyaxial seat, such as the seats included in polyaxial pedicle screws commonly used in spine surgery. A lumen 561 (shown in FIG. 24) passes through arm 540 and inside the tube surrounded by screw 526 such that the assembly may be passed, in the orientation shown in FIG. 24, into a patient through a cannula and over a previously-placed guidewire, such as a "K-wire" commonly used in bone and joint procedures.

At the end of arm 540 is ball end 541, which is rotationally received and captured by seat 525. The arm 540 can be inserted into seat 525 by an operator, or may be provided in a pre-attached state. The arm 540 can be removable from seat 525, or may be permanently, though rotatably, attached, whether provided in a "to-be-assembled" or a pre-assembled state. The ball and socket design of FIG. 23 allows multi-directional rotation of pivoting arm 540. Alternative designs may allow a single degree of freedom, or may allow more sophisticated trajectories of travel for the distal end of arm 540. "U"-shaped grooves 542 are provided to allow the rod 540 to be pivoted in a perpendicular (or other angular) fashion relative to screw 526.

Figure 24:
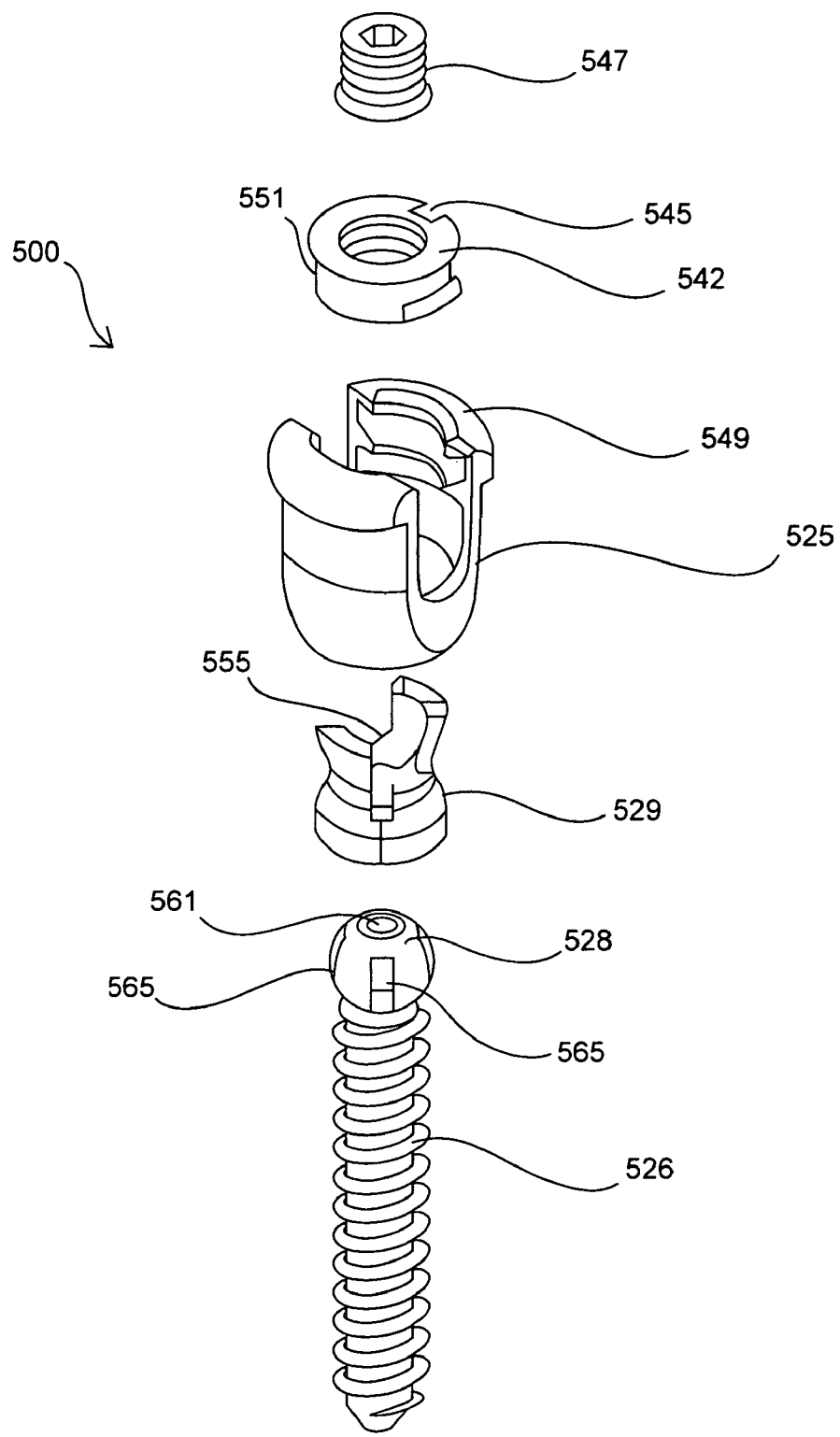
FIG. 24 illustrates an exploded view of the device of FIG. 23.
Figure 25:
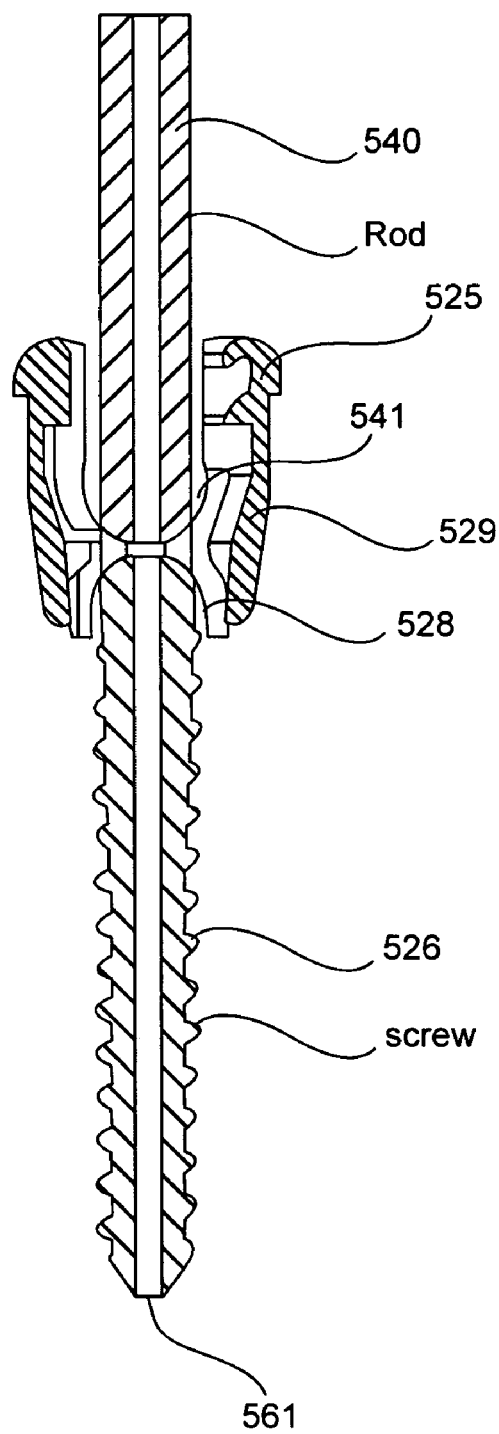
FIG. 25 illustrates a side sectional view of the device of FIG. 23.
Figure 26:
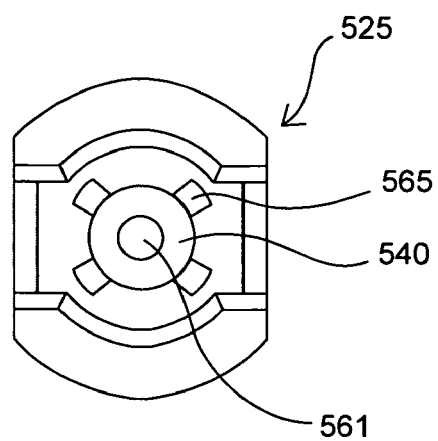
FIG. 26 illustrates a top view of the device of FIG. 23.

Referring now to FIG. 24, an exploded view of a construction of the bone stabilization device is shown. The system 500 includes screw 526 with screw head 528 which matingly engages with a pivoting element or coupler 529 in, e.g., a ball-and-socket arrangement. The pivoting element 529 engages with the seat 525 via a friction-fit, as seen in FIG. 25. Other ways in which the pivoting element 529 can engage the seat 525 include a snap-fit or other such clearance fit. The pivoting element 529 can also be captured by other means, including a C-ring. In general, any geometric features which can cooperatively engage may be employed, including lugs, recesses, etc. The pivoting element 529 is provided with a hole therethrough to accommodate a guidewire within lumen 561. The pivoting element 529 has two partially-spherical voids formed within, as seen in FIG. 25, to accommodate the base 541 of the rod 540 and the screw head 528.

After the rod has been pivoted to a position for use in a patient, the rod may be held in that position by use of a closure element or cap 542 and a set screw 547. The closure element 542 may be snap-fitted into the seat 525 by interaction of closure element tabs 551 and seat grooves 549. Instead of grooves and tabs, lugs may also be employed. Lugs have the benefit of preventing the seat from splaying and releasing the rod. Furthermore, besides the snap-fit of closure element 542, the same may also be dropped in and captured with set screws or other capture devices. One particular other such capture device includes an integral locking nut/plug combination, which eliminates the need for a plug and set screw set.

A closure element slot 545 may be disposed in the closure element 542 so that the same may be further tightened along the groove 549. Of course, various other techniques may also be used to keep closure element 542 within seat 525. The set screw 547 may then be tightened to secure the rod 540 against movement.

The screws such as screw 526 are generally driven into place in the bone when the rod 540 is in the position shown in FIG. 25, that is, coaxial with respect to the axis of the screw thread. The top of the screw head 528 is then rendered inaccessible, although that is where slots for the driving of such screws are generally disposed. For this reason, at least one peripheral slot 565 may be disposed so that a driver with a cooperating element may be used to rotate the screw 526. As even peripheral slots 565 would be rendered inaccessible by the above-described assembly, one or more corresponding pivoting element slots 555 may be disposed in the pivoting element 529.

In use, the screw 526, the pivoting element 529, the seat 525, the rod 540, and the corresponding intermediate elements, e.g., couplers or rod-capturing elements, are assembled prior to implantation in the patient. The device is inserted over the guidewire. The screw is then driven into the desired bone by use of a driver (not shown) generally having one or more protrusions which are long enough to pass through the seat 525, through intermediate elements, couplers, or rod-capturing elements, and to cooperatively engage with peripheral slots 565. The configuration of the driver protrusions is such that the same can cooperatively engage or mate with corresponding peripheral slots 565. Any number of protrusions and slots may be employed. In certain embodiments, 2, 3, 4, or 5 slots 565 and a corresponding number of protrusions on the driver may be employed. The slots 565 may be equidistantly disposed about the screw head 528 or may be otherwise disposed arbitrarily. Once the screw is driven into the bone, the rod 540 may be pivoted and the closure element 542 and set screw 547 applied.

Further details of the above embodiment may be seen by reference to the previously-described embodiments, in which similar elements have similar descriptions and functions. In particular, over-the-wire drivers may be employed such as described above in connection with FIG. 6.

In some of the embodiments shown in FIGS. 3-22 above, the bone stabilization system was seen to include a first bone anchor with a pivoting rod pre-attached. It should be noted that in some embodiments, the first bone anchor may be inserted without the pivoting arm attached. Once the bone anchor is installed, or at a point during the installation thereof, the pivoting arm may be attached.

Attachment of the pivoting arm may be accomplished using any of the configurations described above. Generally, such attachment is preferably performed in a manner in which minimal force is applied to the bone anchor. One method is to employ a "snap-ring" disposed into the seat to retain the pivoting rod after the same is installed in the seat. In this method, application of the snap-ring into the seat should not put undue or an otherwise significant amount of pressure on the bone anchor.

Various advantages inure to this non-pre-attached pivoting rod embodiment. In particular, the same allows customization of various properties of the assembly, including: length, diameter, curvature, dynamic stabilization performance characteristics, etc., to meet the requirements of the patient's spine.

Figure 27:
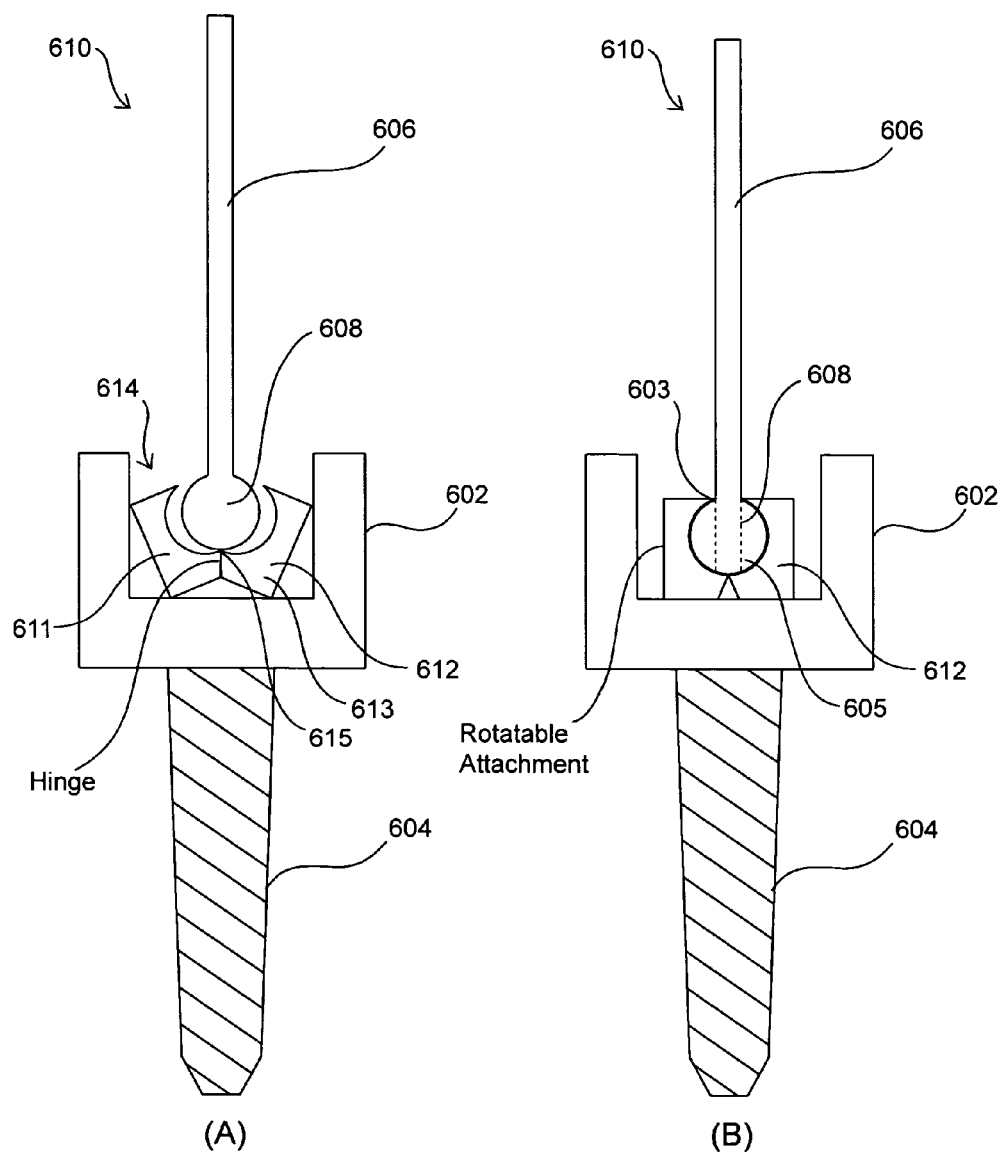
FIG. 27(A) and (B) show a clam-shell capture mechanism for a pivoting rod to attach to a bone anchor.

Besides snap-fit or other sorts of frictional attachment mechanisms to connect the pivoting arm to the first bone anchor, a "clam-shell" capture mechanism may also be employed. Referring to FIG. 27, a system 610 is shown with a bone screw 604, a seat 602 having a void 614 formed therein, and a pivoting rod 606 having a distal end 608. Prior to, during, or following installation of the bone screw 604 into the desired bone segment, the distal end 608 is inserted into the void 614 and more particularly into a clam-shell capture mechanism 612. Clam-shell capture mechanism 612 includes a first shell 611, a second shell 613, and a hinge 615 for connecting the first shell 611 and the second shell 613. The first shell 611 and the second shell 613 are coupled to the seat 602 within its void 614.

The shells may be attached to the seat via various means. There may be a cap over the shell. The shell may be slitted to allow expansion for a snap-fit. The shell may also be attached via a friction-fit or hinge, or via a combination of these techniques and devices.

FIG. 27(A) shows the system during installation of the pivoting rod 606 into the clam-shell capture mechanism 612, and FIG. 27(B) shows the system following installation. To allow a degree of pivot, the clam-shell capture mechanism 612 may have a varying shape and size of the outlet 603 through which the pivoting rod 606 extends. The overall shape of the interior of the clam-shell capture mechanism 612, when closed, must be such that the pivoting rod 606 is held in a secure fashion. However, the same may be provided with a slit (seen as dotted line 605) through which the rod can pivot. The outlet 603 may also be somewhat larger than the diameter of rod 606 so a degree of movement is provided in the plane of the figure, if desired.

Figure 28:
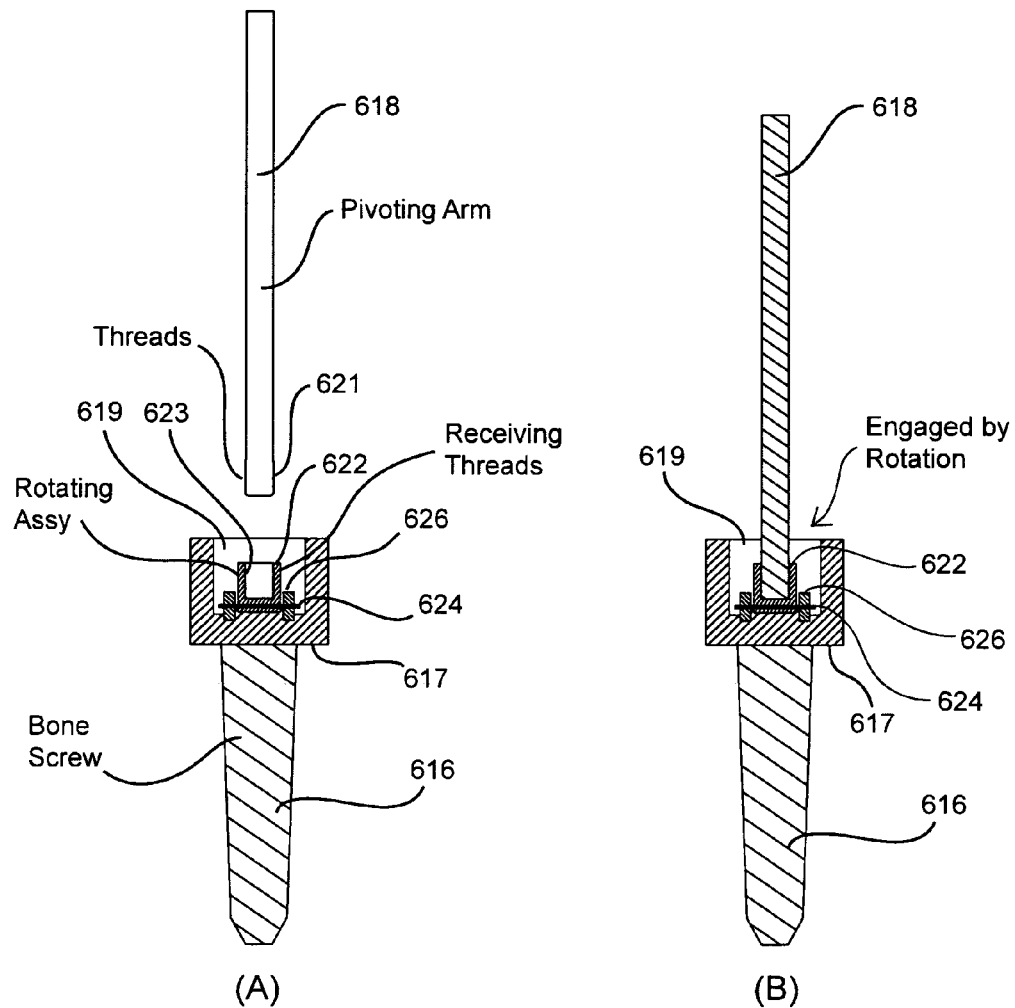
FIG. 28(A) and (B) show a screw-thread capture mechanism for a pivoting rod to attach to a bone anchor.

In another system, shown in FIG. 28(A) and (B), a system is shown with a bone screw 616, a seat 617 having a void 619 formed therein, and a pivoting rod 618 having a threaded distal end 621. Prior to, during, or following installation of the bone screw 616 into the desired bone segment, the threaded distal end 621 is inserted into the void 619 and more particularly into a threaded receiving assembly 622. Threaded receiving assembly 622 includes receiving threads 623, bearings 626, and an axle 624 about which the assembly rotates on the axle. Alternatively, lugs which mate with recesses may be employed. The threaded receiving assembly 622, and in particular bearings 626, are coupled to the seat 617 within its void 619 in known fashion.

FIG. 28(A) shows the system prior to installation of the pivoting rod 618 into the threaded receiving assembly 622, and FIG. 28(B) shows the system following installation. Following installation, the pivoting arm 618 may rotate and its distal end captured by a receiving assembly as described above.

FIG. 29(A) and (B) show top and side views of a frictional-fit engagement for a pivoting rod 634 to attach to a seat 628 of a bone anchor (not shown). Pivoting rod 634 is shown with a small axle 636 therethrough. Of course, axle 636 could also be constituted of two small pins (or one pin which passes all the way through) disposed on opposing sides of the pivoting rod 634. Seat 628 has a void 632 formed therein, with press-fit slots 638 on two sides thereof. Pivoting arm 634, and in particular axle 636, press-fits into the slots 638 and is held in place by the frictional engagement of the axle and the slots. Despite being held in place, the placement of the axle and the slots allows a rotational degree of freedom, in this case out of the plane of the figure. The pivoting arm may then be captured by a receiving assembly as described above.

The slots may have a larger separation opening at the bottom to allow the rod to "snap-in". In addition, the slots may have a larger separation at the top for ease of insertion. In either case, the slots may be tapered to the larger separation. Both of these tapering may be employed in combination or separately.

FIG. 30(A) and (B) show top and side views of a related embodiment of a bayonet-fit engagement for a pivoting rod 644 to attach to a seat 642 of a bone anchor (not shown). Pivoting rod 644 is shown with a small axle 646 therethrough, the nature of which is similar to axle 636 above. The seat 642 has two entry slots 645 and 647, which are respectively adjacent receiving ramps 641 and 643. Pivoting arm 644, and in particular axle 646, is disposed in the entry slots 645 and 647 and then twisted to securedly engage the seat 642, in a bayonet-fit fashion. Despite being held in place, the placement of the axle and the slots allows a rotational degree of freedom, in this case out of the plane of the figure. The pivoting arm may then be captured by a receiving assembly as described above (the ramps have a hole in the middle to accommodate rotation of the rod).

FIG. 31(A)-(D) show assemblies for frictional-fit engagements for a pivoting rod to attach to a seat of a bone anchor, where the degree of range of motion is controllably adjusted. The degree of range of motion may be in travel, angle, or other sort of motion.

Figure 31:
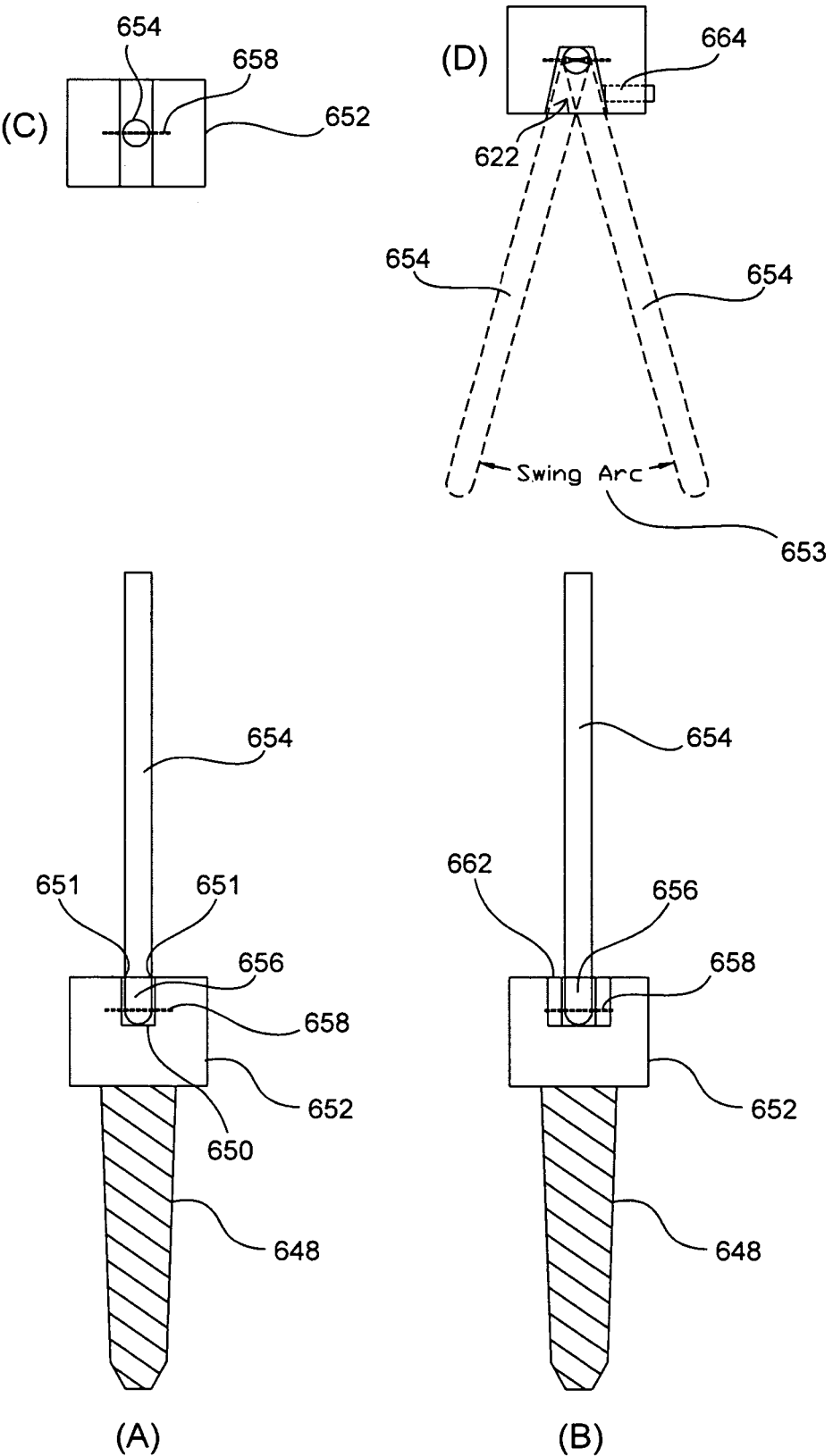
FIG. 31(A)-(D) show assemblies for frictional-fit engagements for a pivoting rod to attach to a seat of a bone anchor, where the degree of range of motion is controllably adjusted.

In particular, referring to FIG. 31(A), pivoting rod 654 is shown with a small axle 658 through a distal end 656 thereof.

Figure 30:
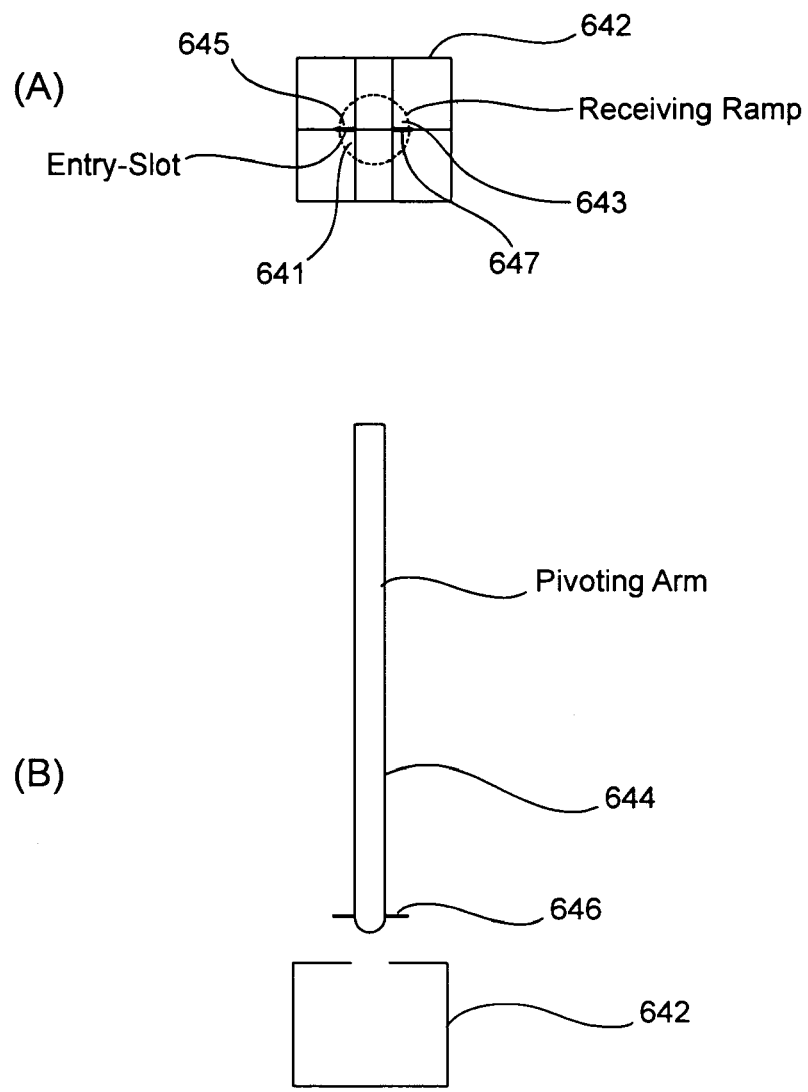
FIG. 30(A) and (B) show top and side views of an alternative embodiment of a frictional-fit engagement for a pivoting rod to attach to a seat of a bone anchor.

In a manner similar to that of FIGS. 29 and 30, the pivoting rod is securely attached to a seat 652, within a groove 650, which in turn is attached to bone screw 648. The side walls 651 of groove 650 may be closely fit to the distal end 656 of the pivoting rod 654 or they may be spaced more apart. If they are closely-fit, as shown in FIG. 31(A) and (C), then the swing of pivoting rod 654 is substantially limited to a single plane. On the other hand, if the side walls 651 of groove 650 are spaced apart to form a void 662 in which sits the distal end 656 of the pivoting rod 654, as shown in FIG. 31(B) and (D), then the swing of pivoting rod 654 has considerably more movement or motion. In this case, the swing of pivoting rod 654 is defined by an arc 653. A set-screw 664 may be disposed to control the size of arc 653. Note that the void 662 may be generally trapezoidal in shape, and that the size of the slots in which the axle 658 is disposed may also be somewhat enlarged to accommodate movements of the axle and rod.

Further, while production of an arc-allowed movement for a pivoting rod is shown, analogous alterations in the side walls and axles and slots would allow additional movements such as: flexion, extension, axial rotation, lateral bending, etc.

Figure 32:
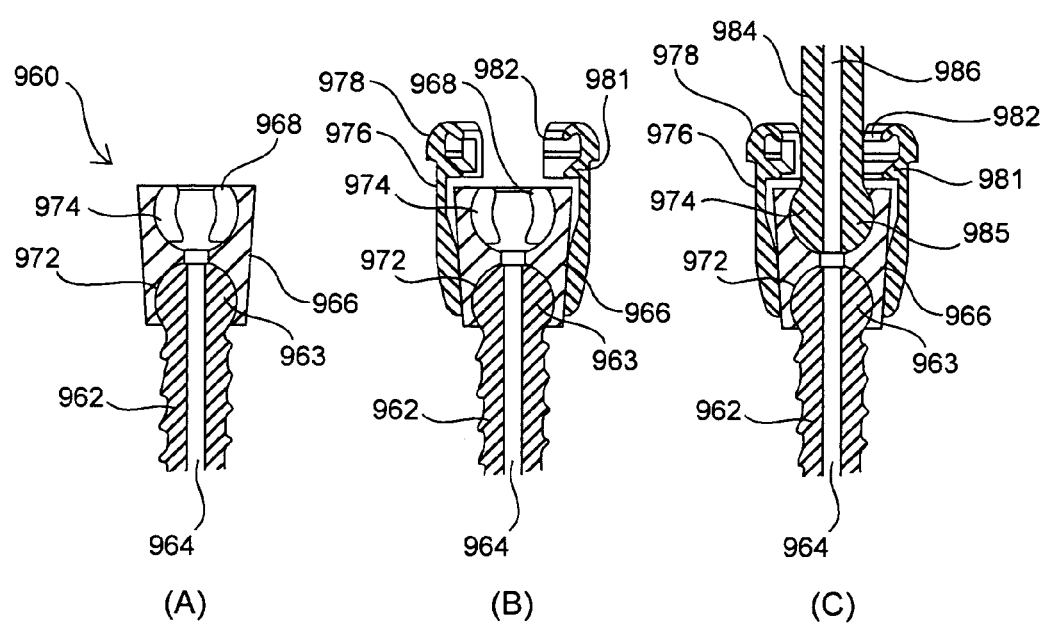
FIG. 32(A)-(C) show assemblies for frictional-fit engagements for a pivoting rod to attach to a seat of a bone anchor.

Referring ahead to FIG. 32(A)-(C), another way of frictionally engaging a pivoting rod to a seat of a bone anchor is shown, as well as a way of frictionally engaging a seat to a bone anchor.

Referring to FIG. 32(A), a system 960 is shown where a bone screw 962 has a guide lumen 964. Following, during, or before installation of the bone screw 962, a snap-in tapered screw retainer 966 is attached to the bone screw 962, in particular by frictionally engaging the screw head 963 to a first screw void 972 formed in screw retainer 966. In one embodiment, slots (not shown) may be formed in the screw retainer 966 around first screw void 972 in order to allow a portion of the screw retainer 966 to "flare" outwards to accept and frictionally engage the screw head 963. A second screw void 974 is formed in the screw retainer 966 generally opposite the first void. The second screw void 974 is configured to accept a pivoting rod following, during, or before installation of the bone screw 962. The second screw void 974 includes an elastic member 968 to assist the securing of the pivoting rod.

Following installation of the screw head 963 into the screw retainer 966, the screw retainer 966 is inserted into a seat 976. Seat 976 includes two lips, lip 981 for securing the screw retainer and lip 982 for securing the pivoting rod. The top end of the screw retainer 966, due to its inherent elasticity, compresses somewhat as it passes lip 981. Following insertion, the top end springs back to its original configuration. The screw retainer 966 outer diameter is greater than the inner diameter of the seat 976, preventing the screw retainer from coming out of the seat. Moreover, a force pulling the screw downward would likewise cause the first void to tighten around the screw head because the first void would itself be caused to decrease in radius due to the inner diameter of the seat. In other words, a force pulling the screw downward also prevents the screw from coming out because any such force pulls the capturing element in such a way as to make the capturing element tighten around the head of the screw, preventing removal.

Once the seat is installed, the pivoting rod 984 with guide lumen 986 and ball end 985 can then be snap-fit into the second void 974. A clearance or space is provided adjacent the second void such that the same can flare out and securely accept the rod.

Figure 33:
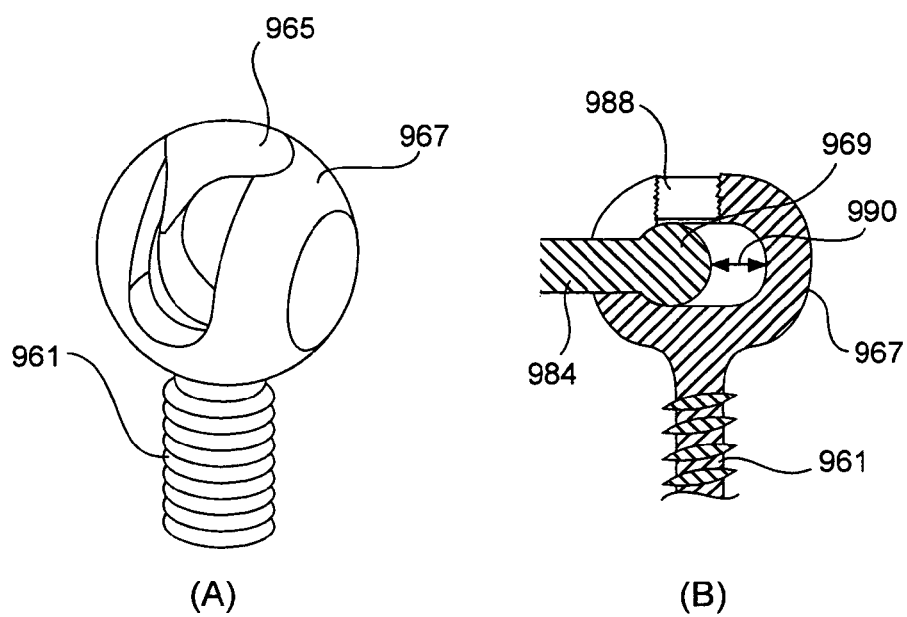
FIG. 33(A) and (B) show an alternative embodiment of a rod and bone anchor assembly.

FIG. 33(A) and (B) show an alternative embodiment of a rod and bone anchor assembly. In particular, referring to FIG. 33(A), a bone screw 961 is shown with a seat 967 having a void 965 therein. Referring to FIG. 33(B), a pivoting rod 984 with ball end 969 has been disposed into the void 965 of the seat 967. A plug 988, which may have threads that engage corresponding threads on the opening of the void, is used to secure the pivoting rod in place. The rod is disposed such that a space 990 is left within void 965 which allows the rod to slide back and forth once the rod is rotated into position, approximately at a 90 degree angle with the screw 961.

Figure 34:
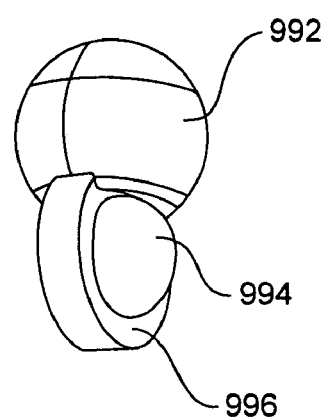
FIG. 34 shows a device that may be employed in an embodiment of a rod and bone anchor assembly.

FIG. 34 shows a device that may be employed in the above embodiments of a rod and bone anchor assembly. In particular, a connector 991 is shown having a tip 992 for capturing a rod (not shown) or a screw retainer which then in turn connects to a rod (not shown). Connector 991 also has a tip 994 having ridge 996 that connects to a bone screw. The ridge 996 allows a rotational force to be transmitted through to the bone screw if desired.

Systems according to the invention may also include those that can provide a degree of flexibility to allow a more convenient capture of a pivoting rod. Referring to FIGS. 35(A)-(C), a system 920 includes two bone screws 922 and 924 that are shown with respective screw heads 926 and 928. Each screw head is disposed in a first void formed in respective retaining members 932 and 934. Retaining members or seats 932 and 934 each have a second void formed therein substantially opposite the first void. The second void contains the ball-shaped ends 942 and 944 of rod 946. Seats 936 and 938 contain respective retaining members 932 and 934. Seats 932 and 934 perform functions similar to those shown in FIG. 32.

The ability of the retaining members or seats to pivot and rotate about the screw head allows the retaining members or seats to be disposed in a number of different positions relative to the axis of the screws. This is important as the screw axes are generally non-parallel as the same depends on the orientation of the pedicle in which they are installed. The retaining members or seats can thus be oriented arbitrarily and independently, and can in particular be oriented such that the pivoting rod can be conveniently installed. In so orienting the retaining members or seats, a degree of compression or distraction is often imparted to the spinal segments.

In an actual installation, typically the rod would be disposed between the retaining members or seats, and a set screw would be started in each to retain the rod. Then a degree of distraction or compression would be imparted to better seat the rod, and the set screw would then be tightened. In this way, the set screw is always properly placed in the retaining members.

Figure 35:
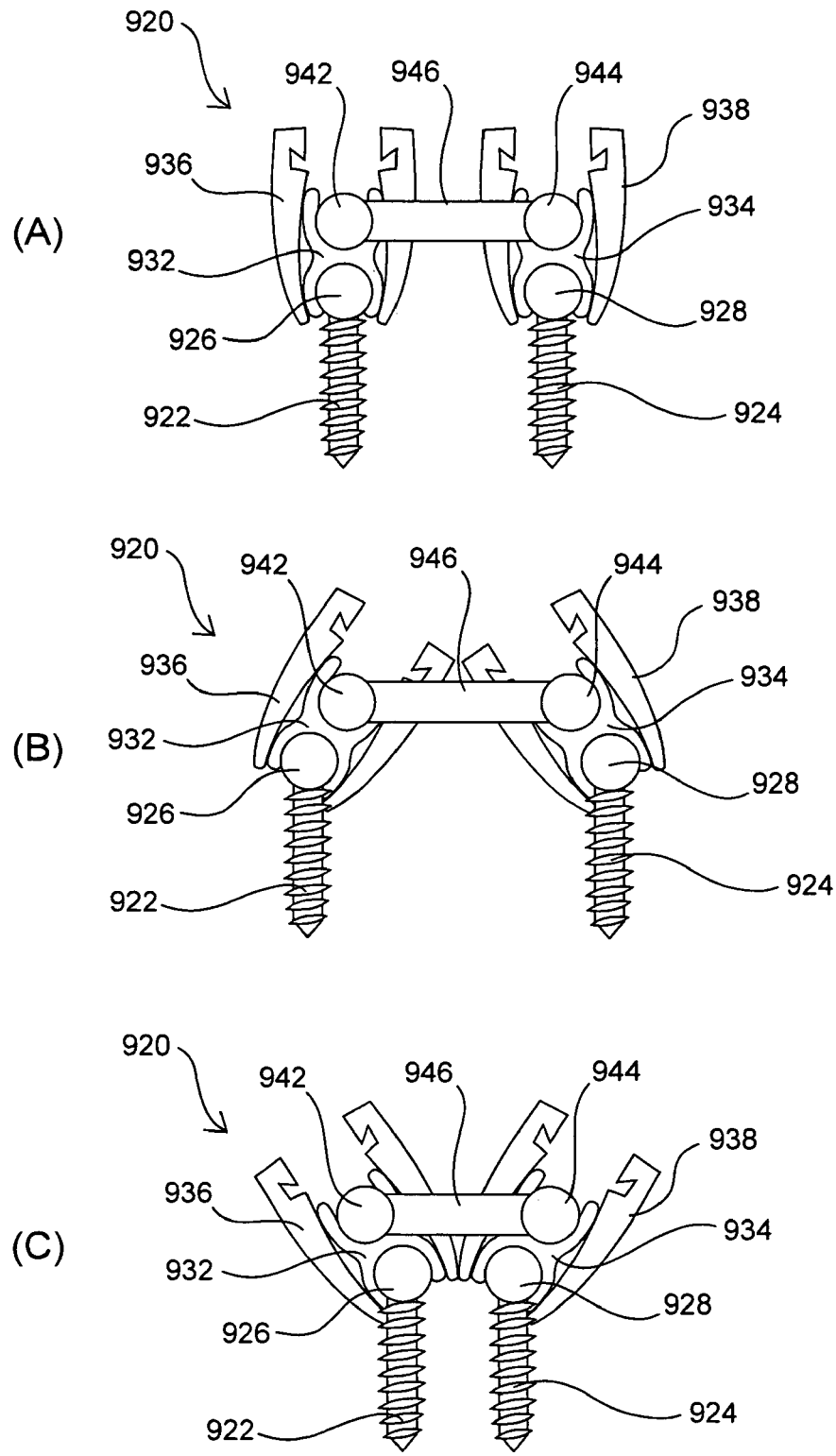
FIG. 35(A)-(C) show a system for automatic distraction or compression.
Figure 36:
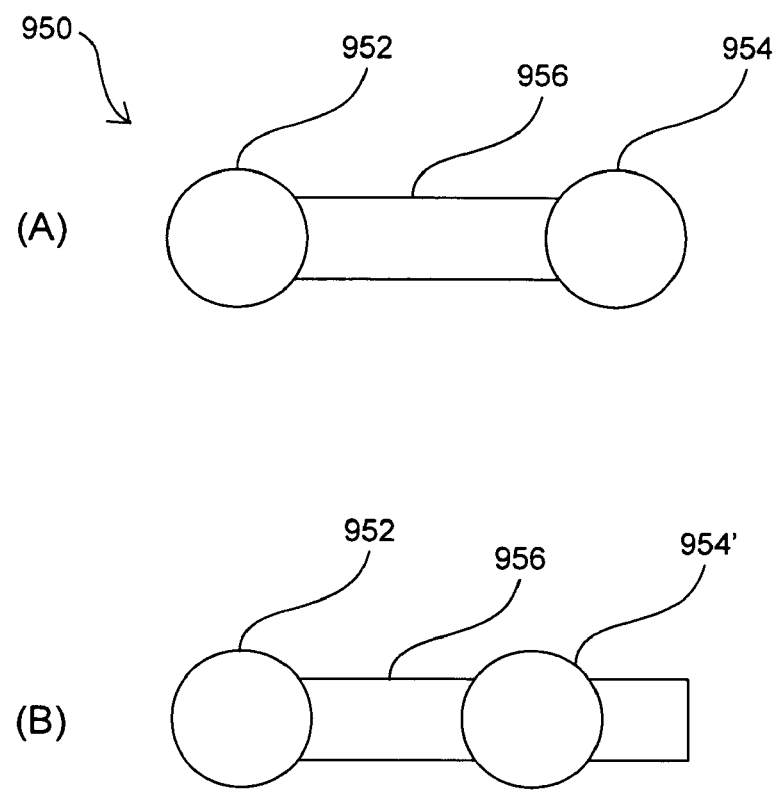
FIG. 36(A) and (B) show an embodiment related to that of FIG. 49(A)-(C) in which one ball end of a pivoting rod is movable.

FIG. 36(A) and (B) show an alternative embodiment 950 of a rod 956 that may be employed in the system of FIG. 35. Rod 956 has a stationary ball end 952 and a movable ball end 954. Movable ball end 954 can slide back-and-forth along rod 956. The same can be secured by methods and devices described here, including set screws, friction-fits, crimping, etc. As the ball end 954 must still be disposed in the void within retaining member 934 (which in turn sits within seat 938), retaining member 934 and seat 938 may be configured with a slot substantially opposite to the slot facing seat 936. This slot, opposite to the slot facing seat 936, allows an excess rod portion 955 to exit the retaining member 934 and seat 938 in the case where the ball end 954 is not at the extremity of the rod 956.

It should be noted with respect to this embodiment that the ball end 954 may be deployed such that it can slide easily along rod 956, or can slide with effort along rod 956, or cannot slide along rod 956. Moreover, a universal joint-type end may be situated at either ball end, or may also be disposed at an intermediate position along rod 956.

While numerous varieties of pivoting rod have been disclosed above, even more types may also be employed. For example, a locking cone system, as shown in FIG. 18 above, may allow a single device to accommodate a continuous range of sizes of pivoting rods.

Further, while numerous varieties of capture and receiving assemblies have been disclosed above, even more types may also be employed. For example, the pivoting rod may be swaged into place or otherwise captured. In any case, the initial attachment of the pivoting rod to the initial seat may be permanent or detachable. Moreover, the secondary attachment of the pivoting rod to the capture seat or other receiving assembly may also be permanent or detachable. Following rotation of the pivoting rod, the same may be fixed in place with, e.g., set screws or other means.

Figure 37:
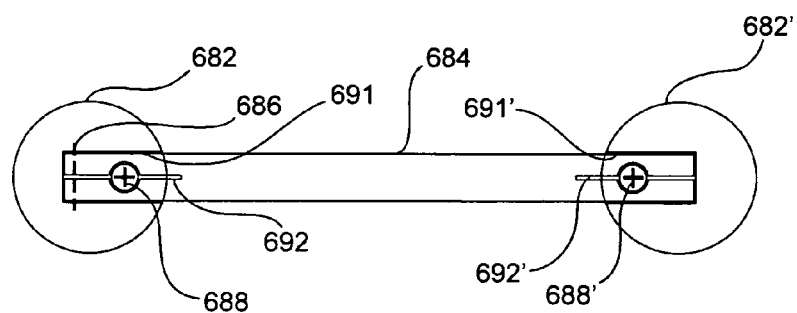
FIG. 37 shows a top view of a rod and seat system in which screws are used to widen a slot, frictionally securing the rod to the seat.

As another example, referring to FIG. 37, a system is shown with a pivoting rod 684 which pivots about axle 686 such that the pivoting rod 684 extends from a seat 682 to a seat 682'. Slots 692 and 692' are provided in the pivoting rod 684 at extremities thereof. A screw 688 is disposed which intersects slot 692, and correspondingly a screw 688' is disposed which intersects slot 692'. When the pivoting rod 684 is in a deployed configuration, as shown, screws 688 and 688' may be tightened, which in turn widens slots 692 and 692' respectively. As the slots widen, the extremities of rod 684 bow outward and are forced against sidewalls 691 and 691', frictionally engaging the same. Once the frictional engagement is great enough, pivoting rod 684 is secured between the seats, and bone stabilization occurs. Again, it is noted that the screws 688 and 688' need not provide a force normal to the plane of the figure, frictionally securing the rod against the seat. Rather, the screws bow the rod ends outward, parallel to the plane of the figure, frictionally securing the rod against the sidewalls.

Of course, a set screw may also be used that does provide a force normal to the plane of the figure, frictionally securing the rod against the seat.

As noted above in connection with the discussion corresponding to FIGS. 10-13, 16, 19, and 22, embodiments of the invention may not only be used to provide stabilization to two adjacent vertebrae, but indeed can be used in a multi-level fashion to stabilization three or more vertebrae. Additional details concerning these designs may be seen by reference to FIGS. 38-43.

Figure 38:
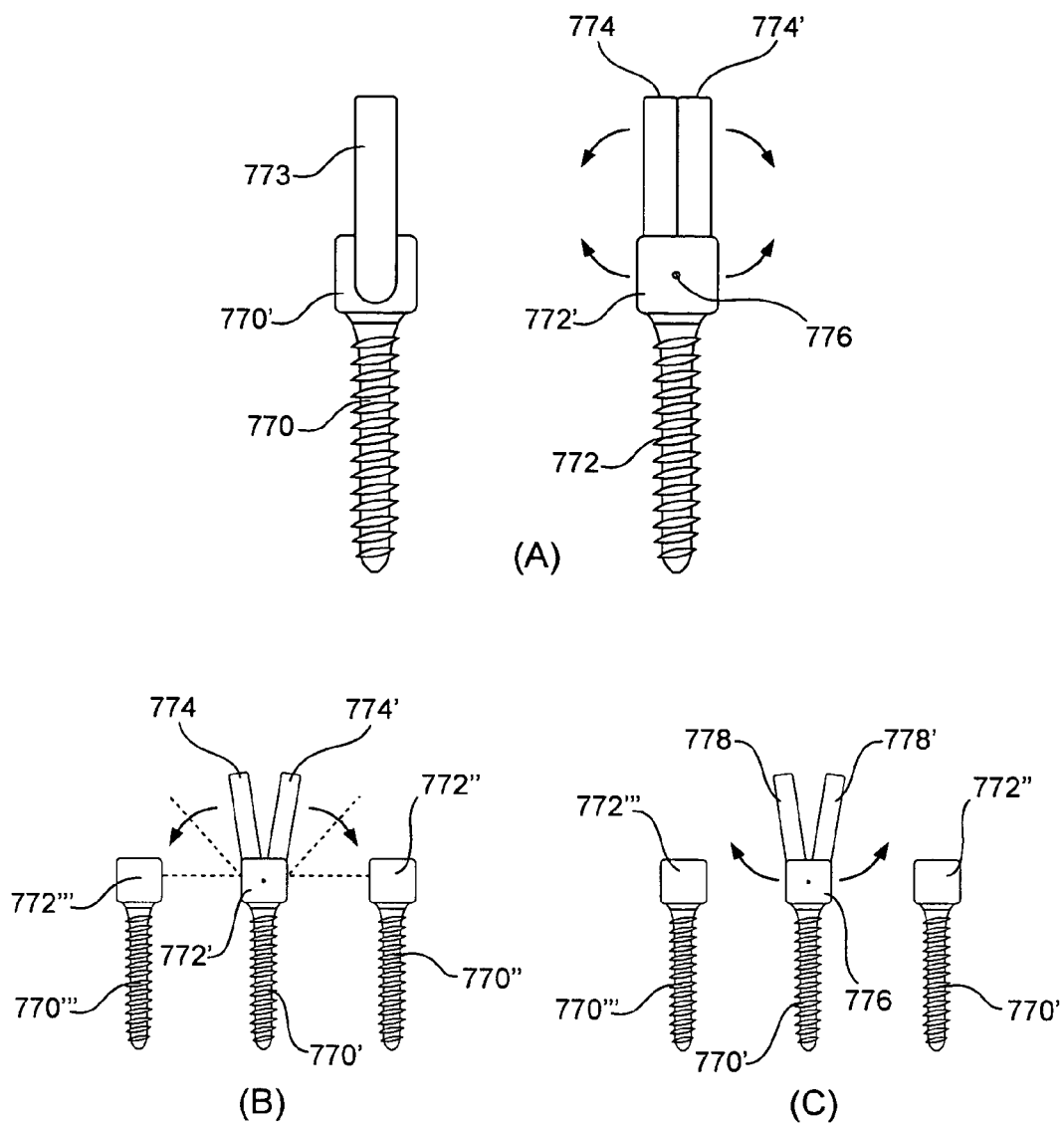
FIG. 38(A)-(C) show a dual-pivoting rod assembly for use in multi-level bone stabilization or fixation.
Figure 39:
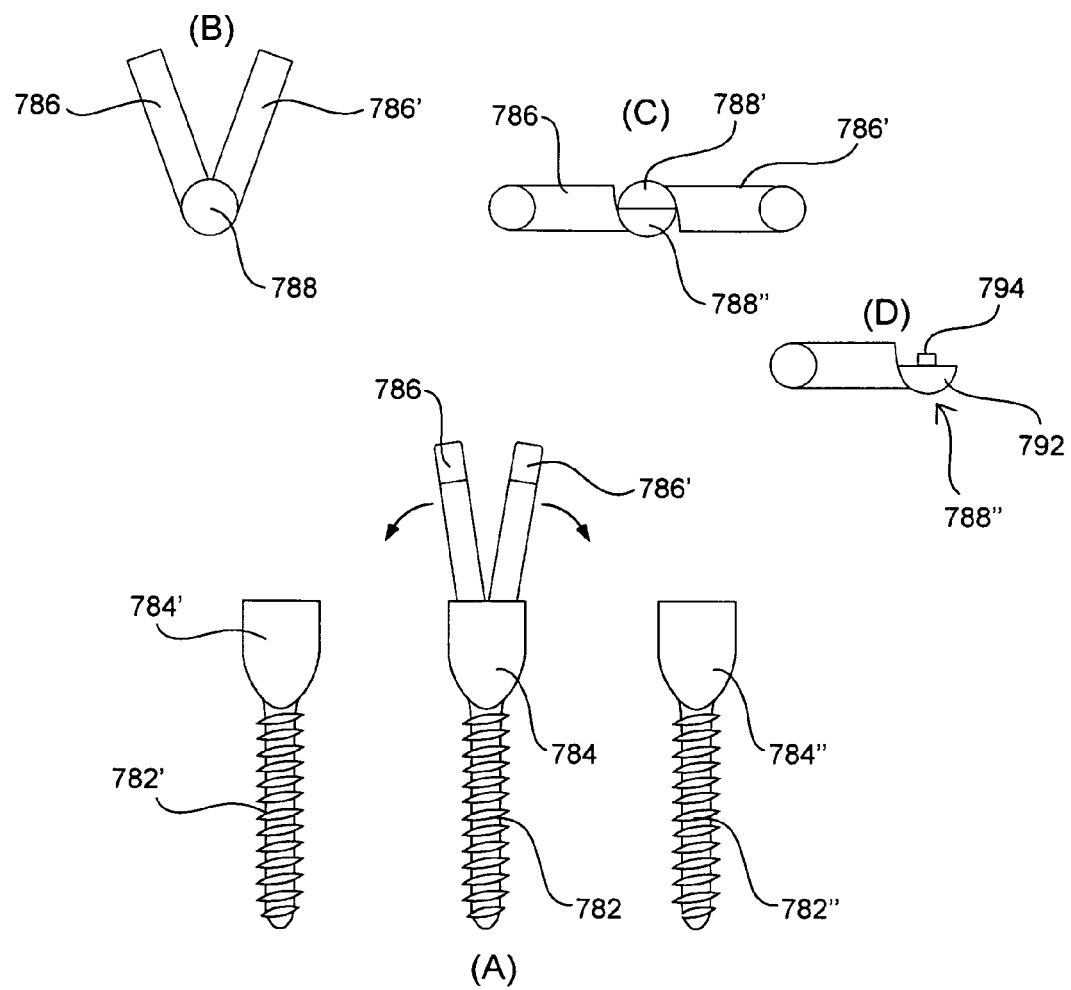
FIG. 39(A)-(D) show details of an embodiment related to that of FIG. 41(A)-(C).
Figure 40:
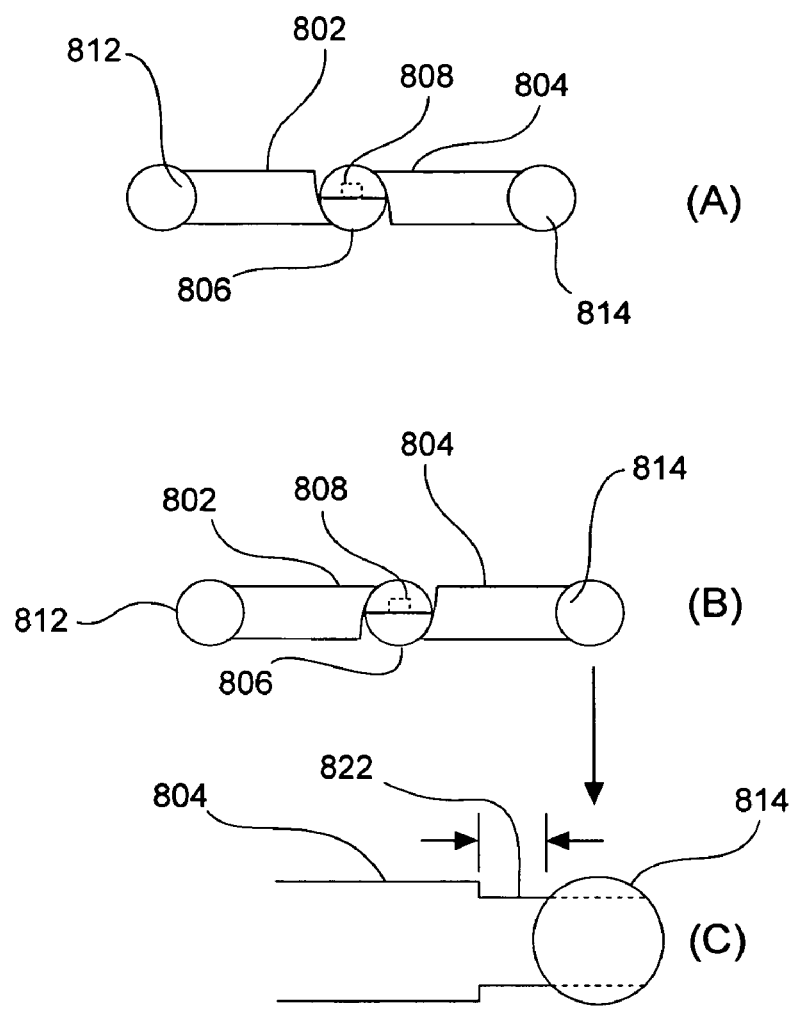
FIG. 40(A)-(C) show a dual arm system with a unitary hinged assembly employing adjustable-length rods.
Figure 41:
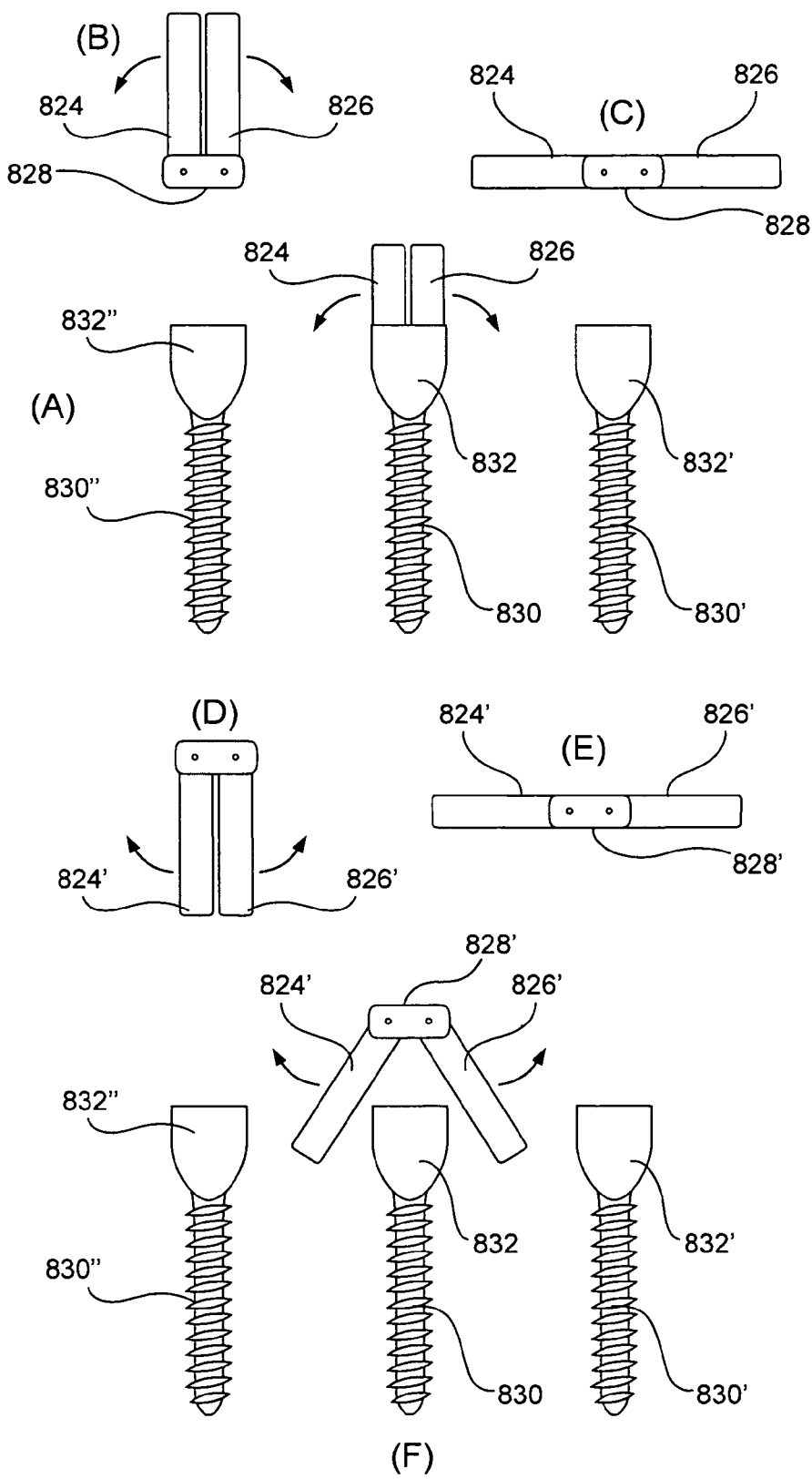
FIG. 41(A)-(F) show a dual arm system with a unitary hinged assembly employing multiple axles for the pivoting rods.
Figure 42:
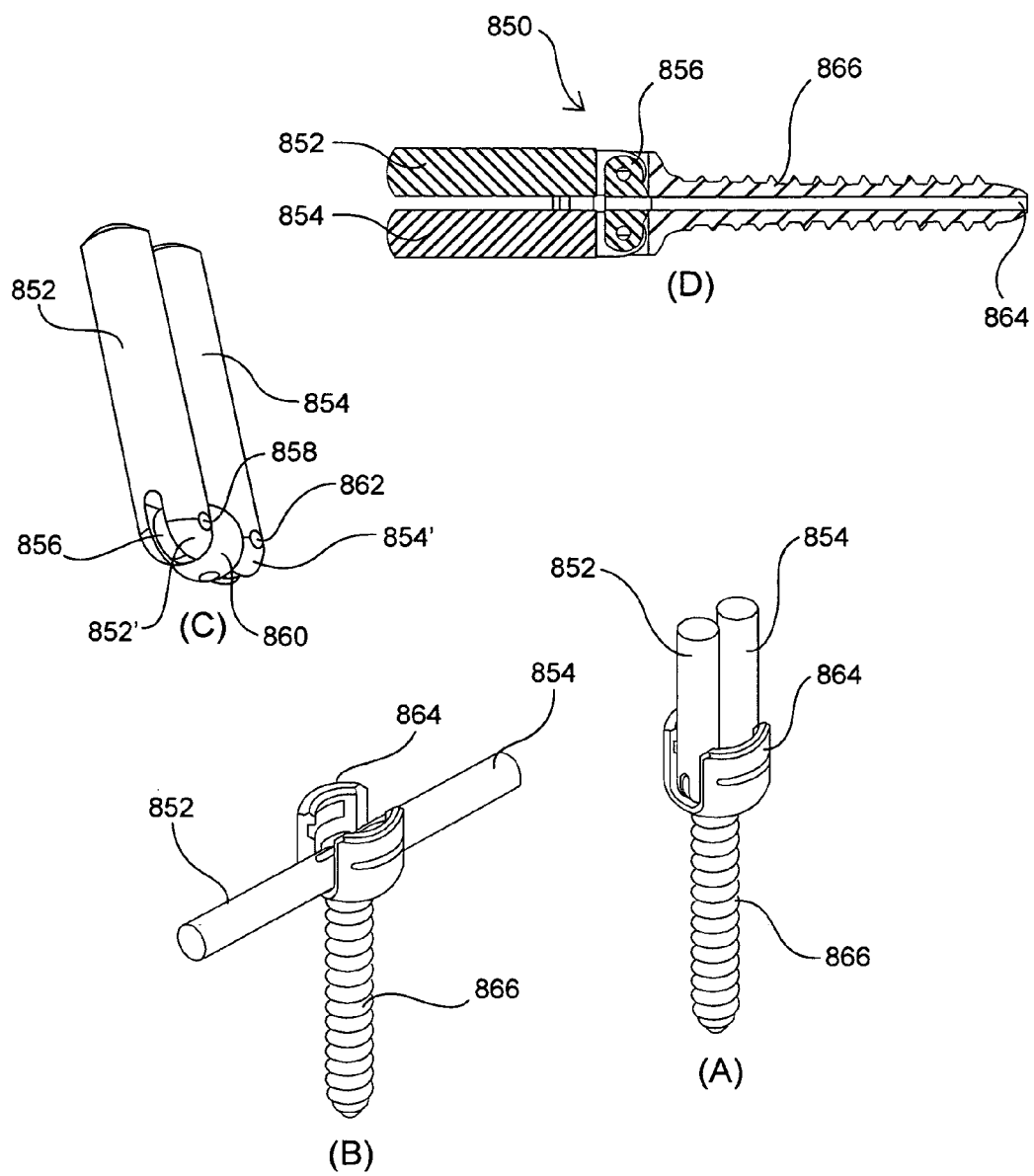
FIG. 42(A)-(D) show an alternative dual arm system with a unitary hinged assembly employing multiple axles for the pivoting rods.
Figure 43:
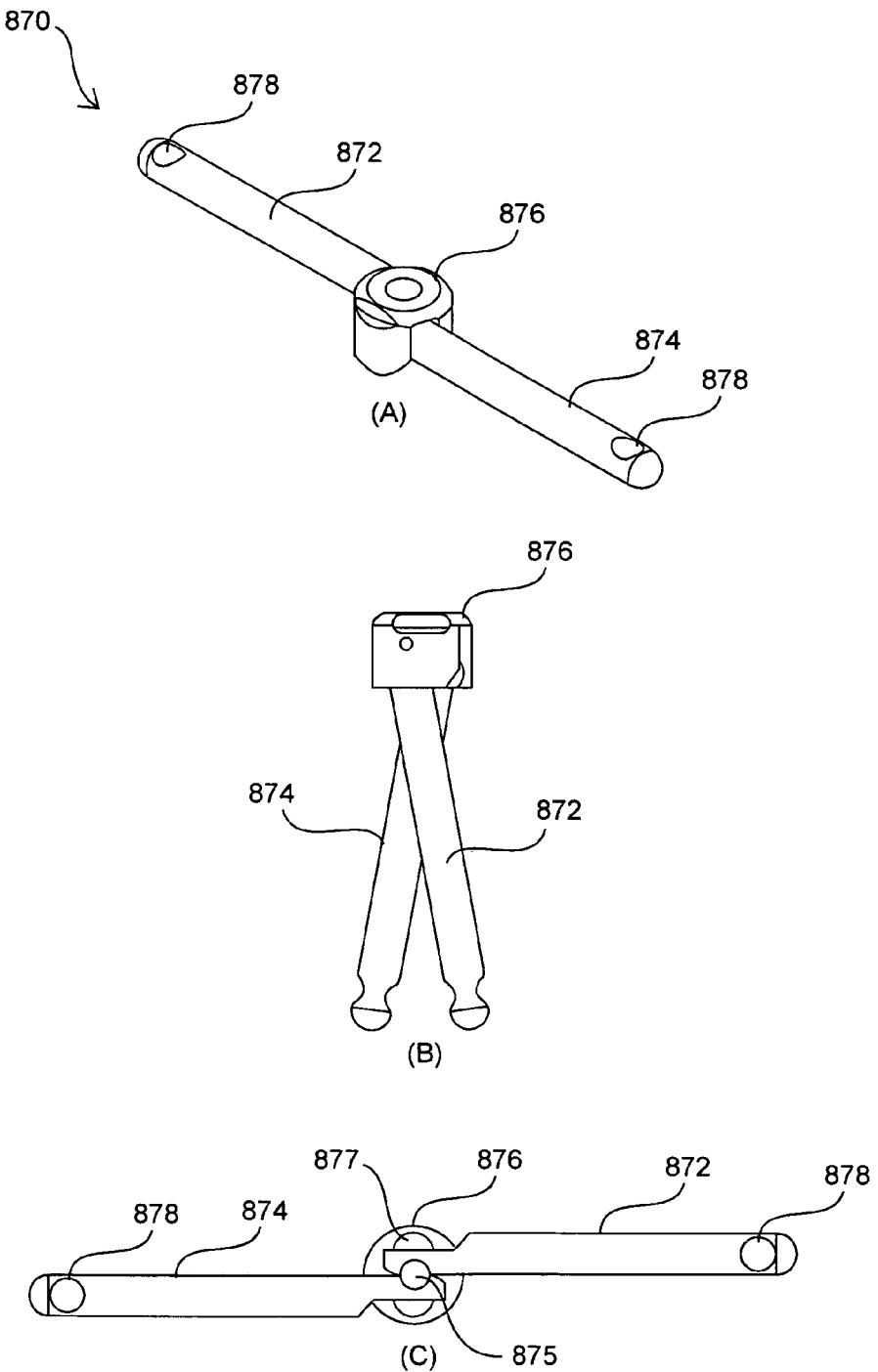
FIG. 43(A)-(C) show a dual arm system with a unitary hinged assembly employing pivoting rods with an offset angle.
Figure 44:
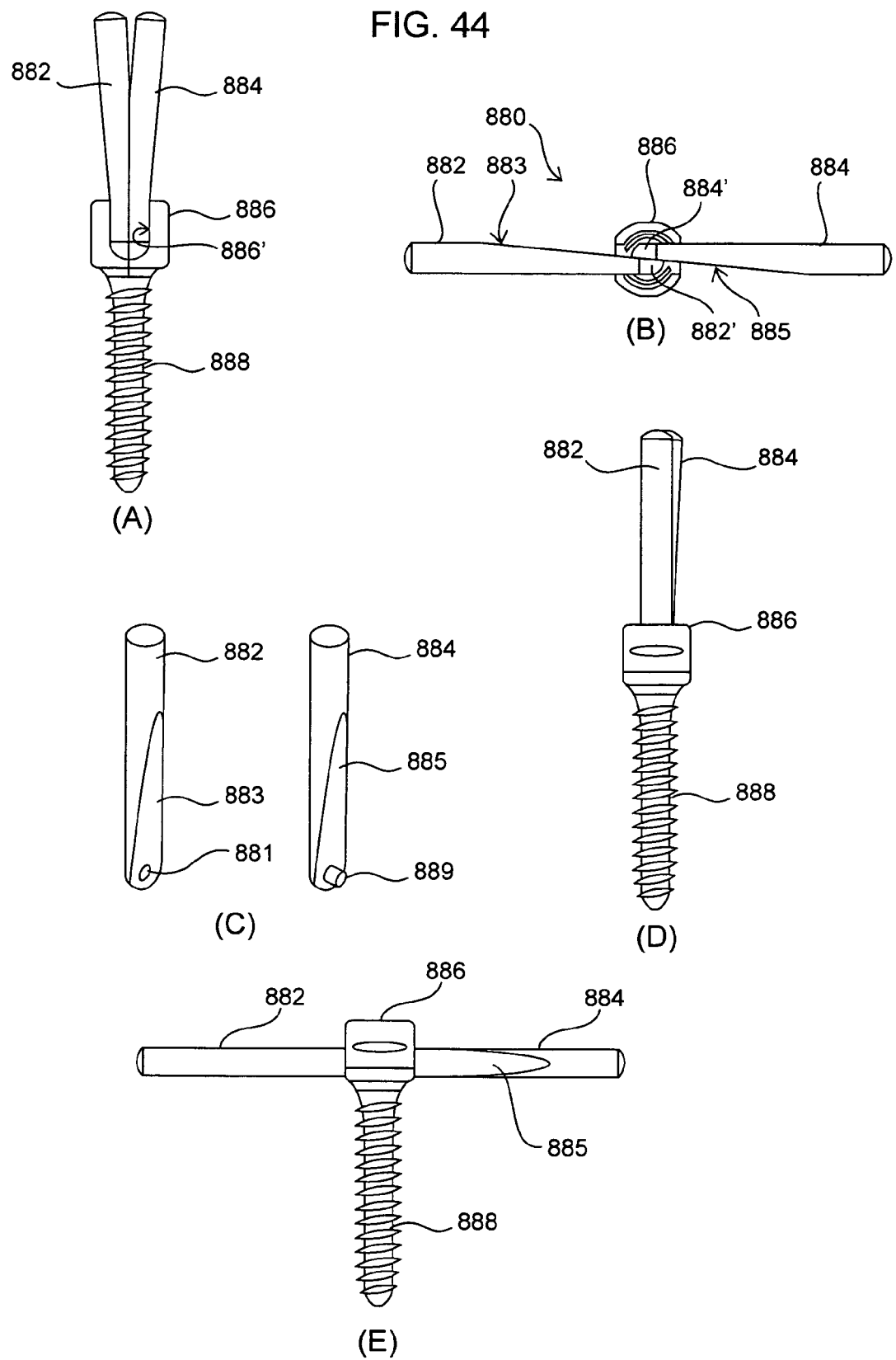
FIG. 44(A)-(E) show a dual arm system with a unitary hinged assembly employing pivoting rods, each with a complementary taper.

Referring to FIG. 38 (A)-(C), a system is shown in which two bone screws 770 and 772 are shown, each with an associated respective seat 770' and 772'. Seat 770' houses one pivoting rod 773, while seat 772' houses dual pivoting rods 774 and 774'. Seat 772' with dual pivoting rods further has an axle 776 about which each rod pivots. Rod 773 also has an axle (not shown). The dual rod system can be loaded into the seat at any time, before, during, or after installation of the bone anchor, to allow connection to adjacent screws, e.g. at seat 770'.

Referring to FIG. 38(B), a system is shown in which the dual-rod system of FIG. 38(A) (right hand side) is shown between two bone anchors. These two bone anchors are not shown with their own rods, but the same may also be incorporated. To the right of bone anchor 770' and seat 772' is bone anchor 770" and seat 772". To the left of bone anchor 770' and seat 772' is bone anchor 770'" and seat 772'". In FIG. 38(B), the dual rod system is connected to the seat at their distal end, in which case the rods rotate down to be captured by receiving assemblies, one rotating clockwise and the other counter-clockwise. 00184 Referring to FIG. 38(C), a system is shown in which a related dual-rod system is shown between two bone anchors. As before, these two bone anchors are not shown with their own rods, but the same may also be incorporated. The dual-rod system has a bone anchor 770', seat 776, and two rods 778 and 778'. To the right of bone anchor 770' and seat 776 is bone anchor 770" and seat 772". To the left of bone anchor 770' and seat 772' is bone anchor 770'" and seat 772'". In FIG. 38(C), the dual rod system is configured such that the rods slide outward, from their distal ends, such that the distal ends then become the portions captured by receiving assemblies.

FIG. 39(A)-(D) show an embodiment related to that of FIG. 38(A)-(C). In particular, referring to FIG. 39(A), a bone screw 782 is shown with a seat 784 and a dual-rod assembly having rods 786 and 786'. On the left side of bone screw 782 is a bone screw 782' with a seat 784', and on the right side of bone screw 782 is a bone screw 782" with a seat 784". Rod 786' rotates in a clockwise direction to engage a capture mechanism (not shown) within seat 784", and rod 786 rotates in a counter-clockwise direction to engage a capture mechanism (not shown) within seat 784'.

FIG. 39(B) shows additional details. In particular, the figure shows a rotation mechanism 788 through which rods 786 and 786' rotate. In particular, referring to FIG. 39(C), rotation mechanism 788 has a first half 788' and a second half 788". First half 788' and second half 788" matingly engage, e.g., each can form half of a sphere, and the two combined can approximately form a complete sphere. FIG. 39(D) shows a plug 794 formed on an interior wall of half-sphere 792 of second half 788" which can matingly engage a corresponding hole (not shown) in 788'. Other rotation mechanisms can also be employed.

Other systems can also provide multilevel stabilization. FIGS. 40-44 show additional embodiments of systems employing dual arms on a single hinged assembly.

In particular, FIG. 40(A)-(C) show a dual arm system with a unitary hinged assembly employing adjustable-length rods. In this embodiment, pivoting rods 802 and 804 meet at a rotation mechanism having first half 806 and second half 808. The rotation mechanism may be like that disclosed above. The rotation mechanism snaps into place in a seat like those disclosed above. A first ball 812 is disposed at an end of rod 802 opposite that of first half 806, and a second ball 814 is disposed at an end of rod 804 opposite that of second half 808.

In some of the above-described capture mechanisms, a pivoting rod is that which is captured, and the same is secured by a threaded plug, set screw, or other such retainer. Accordingly, the system is per se adjustable because the rod may be captured at any point along its length. In FIG. 40(A)-(C), if the ball is that which is to be captured, then the length of the rod becomes much more important. Accordingly, in FIG. 40(A)-(C), the ball 814 is attached to an inner rod 822 (see FIG. 40(C)) which is slidably and telescopically disposed within rod 804. Inner rod 822 may become immovable with respect to rod 804 in a number of ways, including via use of a set screw, by rotation of inner rod 822 on which a cam is biased to engage the inner wall of rod 804, etc. Alternatively, the same may be left to slidably move relative to rod 804, depending on the desires of the physician.

FIG. 41(A)-(F) show a dual arm system with a unitary hinged assembly employing multiple axles for the pivoting rods. Referring to FIG. 41(A)-(F), a bone screw 830 is shown with a seat 832 and a dual-rod assembly having rods 824 and 826. On the left side of bone screw 830 is a bone screw 830" with a seat 832", and on the right side of bone screw 830 is a bone screw 830' with a seat 832'. Rod 826 rotates in a clockwise direction to engage a capture mechanism (not shown) within seat 832', and rod 824 rotates in a counter-clockwise direction to engage a capture mechanism (not shown) within seat 832".

FIG. 41(B) shows additional details. In particular, the figure shows a rotation mechanism 828 through which rods 824 and 826 rotate. In particular, the rotation mechanism includes dual parallel axles, each attached to one of rods 824 and 826.

FIG. 41(B) shows the rods in a parallel alignment, such as during insertion. FIG. 41(C) shows the rods in an anti-parallel alignment, such as following deployment.

FIG. 41(F) shows the same set of bone screws and seats, this time being engaged by pivoting rods 824' and 826' which are coupled together via rotation mechanism 828'. In this embodiment, the step of pushing the rod assembly down acts to automatically open the rods, swinging the same into position where they may be captured by an appropriate receiving assembly. In a manner similar to that of FIG. 41(B) and (C), FIG. 41(D) shows the rods in a parallel alignment, such as during insertion, while FIG. 41(E) shows the rods in an anti-parallel alignment, such as following deployment.

In all of these embodiments, it should be noted that the rod can be pre-attached to the seat or alternatively the same can be installed in the seat following installation of the bone screws into the spine of the patient.

FIG. 42(A)-(D) show an alternative dual arm system 850 with a unitary hinged assembly employing multiple axles for the pivoting rods. In particular, rods 852 and 854 are shown with distal ends 852' and 854' (see FIG. 42(C)), respectively. These distal ends each have a groove into which a flat extension 856 is disposed. Flat extension 856 (and a corresponding flat extension (not shown) within rod 854 are attached to central assembly 860. Moreover, through the flat extensions axles 858 and 862 are disposed, which extend from one side of the distal ends 852' and 854' to a side diametrically opposite. In this way, rods 852 and 854 are hingedly attached to central assembly 860.

The distal ends of the rods are disposed within a seat 864 attached to a bone screw 866 having a guidewire lumen 864 disposed therein.

FIG. 42(A) shows the rods in a position for insertion and FIG. 42(B) shows the rods in a deployed configuration.

FIG. 43(A)-(C) show a dual arm system 870 with a unitary hinged assembly employing pivoting offset rods. In particular, rods 872 and 874 are shown with distal ends having indentation features 878. Indentation features 878 allow for secure connection to other seats on a multilevel system.

Rods 872 and 874 are joined at a rotation mechanism 876 which includes an axle 877 about which both rods rotate. Multiple axles may also be employed. When the rods are in an insertion configuration, they are generally parallel to each other. When the rods are deployed, they are anti-parallel to each other. A guide lumen 875 may be employed for placement.

FIG. 44(A)-(E) show a dual arm system 880 with a unitary hinged assembly employing pivoting rods, each with a complementary taper. In particular, rods 882 and 884 are shown joined within seat 886 attached to bone screw 888. The rods may rotate relative to each other via an axle or other mechanism (not shown). For example, referring to FIG. 44(C), the rod 884 may have a plug 889 formed on a end 882' which matingly engages a hole 881 formed on an end 884' of rod 882. When the plug 889 engages the hole 881, the ends 882' and 884' of rods 882 and 884 adjacent the plug and hole form a substantially spherical head which may be securely and rotatably inserted within seat 886. A slot 886' may be formed within the seat 886 into which the rods rotate when deployed. To allow the rods to align in a substantially parallel manner during, e.g., insertion, each rod may be formed with a cooperating taper. In the figures, rod 882 is formed with a taper 883 and rod 884 is formed with a taper 885. The tapers are formed in a manner such that the face each other when the rods are disposed in the seat, either before, during, or after installation of the bone screw.

When the rods are in an insertion configuration, they are generally parallel to each other, as shown in FIGS. 44(A) and (D). When the rods are deployed, they are generally anti-parallel to each other, as shown in FIG. 44(E). Of course, they are still deployed through the cannula.

Other multi-level systems have been disclosed above, in particular, dual attaching cradles on a single receiving assembly are shown in FIGS. 12 and 13, and a sequential arrangement, having a hinged assembly and an attaching cradle coupled to a bone anchor, is shown in FIG. 22.

Many of the dual arms disclosed above show two arms attached to a single seat on a bone screw, i.e., dual pivoting rods on a unitary hinged assembly, these rods then linking to two receiving assemblies diametrically opposed from each other. However, it is noted that a receiving assembly itself may also include a rotatably attachable pivoting rod. In this case, clearance should be allowed for the rotation, typically via a ball-and-socket or hinge, while still allowing secure attachment of the first pivoting rod. One way of configuring this is for each bone anchor to include a receiving assembly (for a first pivoting rod) and a separate seat for attachment of a second pivoting rod (which is then received by another receiving assembly). An advantage of this configuration is that the bone screw/seat/pivoting rod/receiving assembly systems can all have the same or a similar construction, easing manufacture. There is no need to have a separate construction for the hinged assembly vis-a-vis the receiving assembly. Such an embodiment is shown above in FIG. 22*b* with particular reference to assemblies 70*a* and 70*b*.

The above description has disclosed devices and methods for minimally-invasive surgery. Certain additional complementary features may apply to many or all of the above.

Figure 45:
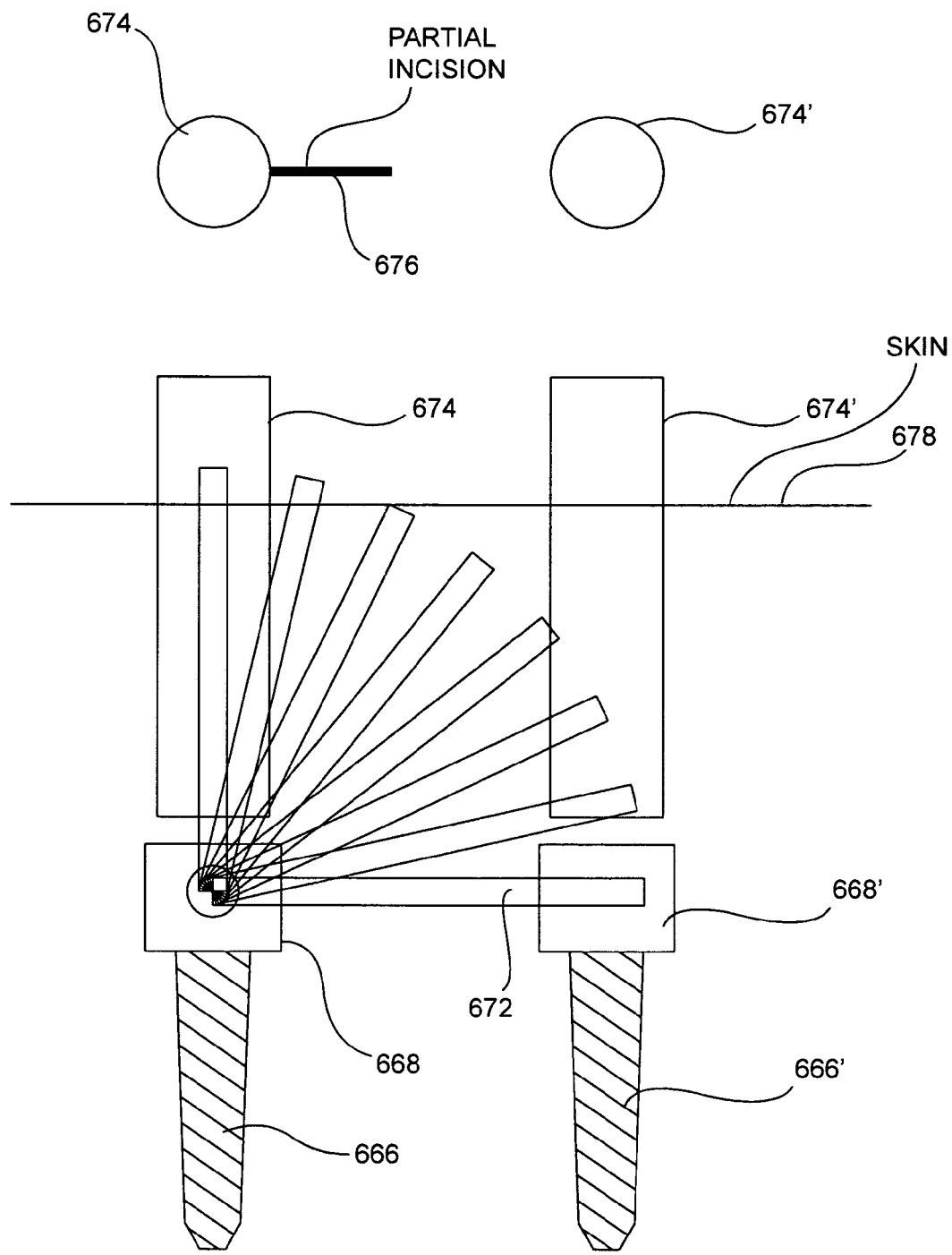
FIG. 45 shows top and side views of a bone screw system employing a partial skin incision to allow use of a long pivoting rod.

For example, referring to FIG. 45, two bone screws 666 and 666' are shown below skin 678. Seats 668 and 668' are attached, or integral with, respectively, bone screws 666 and 666'. A pivoting rod 672 has a proximal end attached to seat 668 and when deployed extends to and is captured by seat 668'. Insertion cannulae 674 and 674' are shown above their respective seats and bone screws. As may be seen, when in the insertion configuration, and due to the length of the pivoting rod 672, pivoting rod 672 extends a distance above skin 678. A shorter pivoting rod would not extend above the skin, and could be immediately rotated into the receiving assembly. However, due to the length, the pivoting rod cannot be rotated into seat 668'. In this case, a partial incision 676 may be made to accommodate a partial amount of the rotation of the pivoting rod 672. The first part of the rotation of the pivoting rod passes through the skin 678 through the partial incision 676. In this way, the partial incision 676 allows use of a longer pivoting rod, as may be desired for certain procedures. The same may also accommodate sites that are located closer to the skin.

Figure 46A:
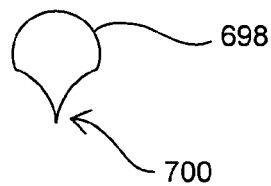
FIGS. 46 and 46(A) show side views of a bone screw system employing a pivoting rod with a sharpened edge to assist in skin dissection.
Figure 46:
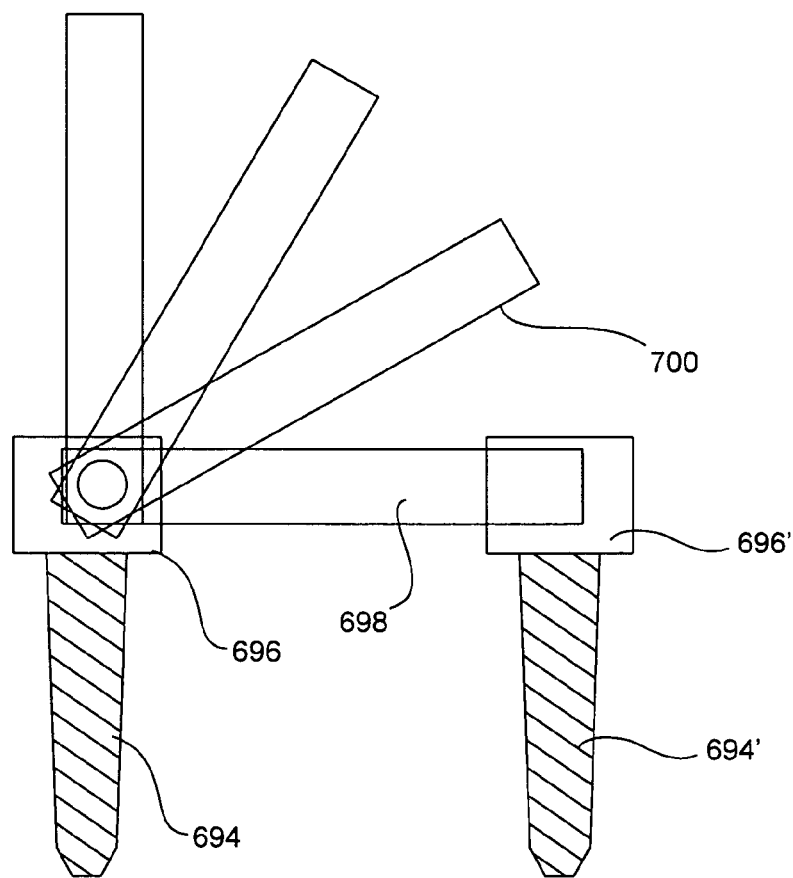

Systems may also be employed that nearly-automatically perform a level of dissection per se. Referring to FIG. 46, a system is seen with two bone screws 694 and 694', respective seats 696 and 696', and pivoting rod 698. The pivoting rod 698 is constructed with an anterior facing edge 700 that is sharpened to reduce the forces required to pass through tissue during the rotation of the pivoting rod 698 into the receiving assembly such as seat 696'. In other words, during rotation, sharpened edge 700 can improve dissection to allow passage of the pivoting rod 698 through the skin and surrounding tissues.

In an alternative embodiment to FIG. 46, sharpened edge 700 may be blunted prior to the closing procedure. Alternatively, the sharpened edge itself, though not the pivoting rod, may be made biodegradable such that, over time, it would dissolve in the body. The sharpened edge could also be filed off or otherwise dulled by the physician, or a collar may be slid onto the edge so that the sharpened edge is not unsheathed while maintained in the body.

Figure 47:
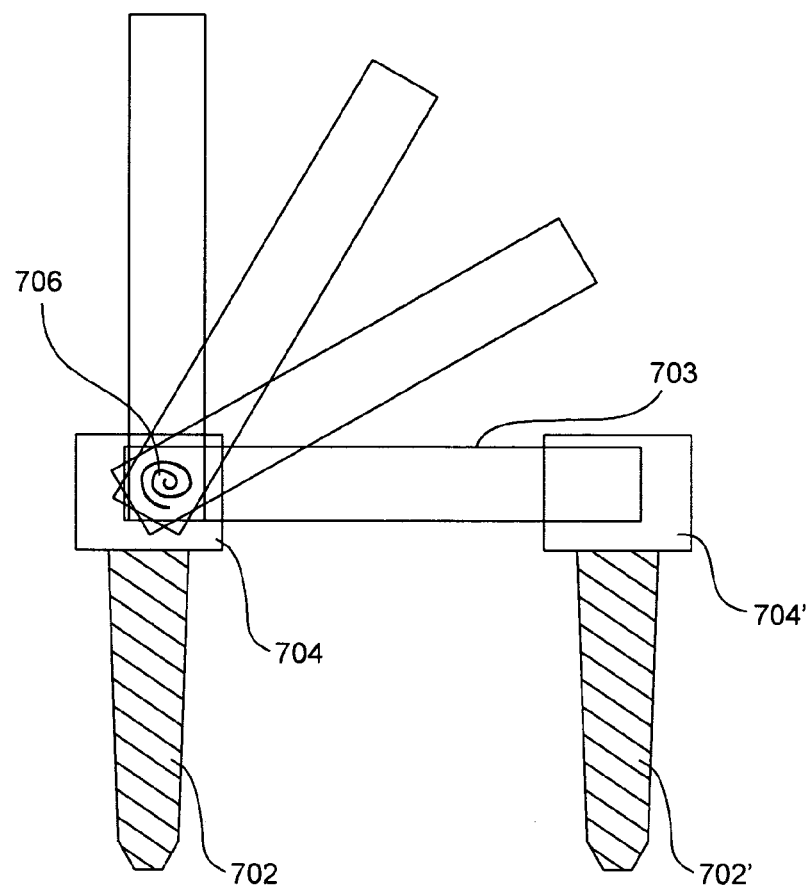
FIG. 47 shows a side view of a bone screw system employing a pivoting rod with a resiliently-biased feature.

To assist in insertion and installation or in maintenance in a deployed position, the pivoting rod can be combined with a torsional spring to bias the pivoting arm in various positions. Referring to FIG. 47, a system is seen with two bone screws 702 and 702', respective seats 704 and 704', and a pivoting rod 703. The end of pivoting rod 703 that is initially disposed within a seat, i.e., seat 704, is also coupled to a torsional spring 706. The torsional spring 706 may resiliently bias the pivoting rod 703 in a position parallel to bone screw 702, perpendicular to the axis of the bone screw 702, or at any angle in between as may be desired.

In the case where the torsional spring 706 resiliently biases the pivoting rod 703 in a position perpendicular to bone screw 702, the rotation procedure may be simplified as the pivoting rod will naturally move to the "captured" or "received" configuration. In the case where the torsional spring 706 resiliently biases the pivoting rod 703 in a position parallel to bone screw 702, the insertion procedure may be simplified as the pivoting rod will move more easily down the cannula. The parallel position will also result in a more convenient removal or readjustment following the pivoting action, if necessary or desired. The angular position of torsional spring 706 may be reset at any time to change the bias, i.e., the "rest" position. This bias may be adjustable by the physician. For example, the spring may be attached to the seat with a screw such that rotation of the screw alters the rest position of the spring.

Of course, the torsional spring 706 may be biased at any point between the two extremes discussed above and many different functional elements may be employed to resiliently bias the spring in one or more positions. For example, different types of springs or other elastic members may be employed.

Other systems which may maintain a pivoting rod in one configuration or another are shown above. In particular, the above-described FIG. 31(A)-(D) show a system in which the frictional engagement between the rod 654 and the groove walls 651 allow a degree of maintenance of the rod in a desired position. In other words, if the groove walls 651 fit the rod 654 tightly, the same is resiliently held in a given position. This embodiment has an advantage that the any position may be the "resiliently-biased" position, as placement of the rod in any rotational position naturally becomes the "rest" position (or which may be set by the physician via an adjustment), and any movement out of that position is met with a return force, unless and until the movement out of that position becomes so great that a new "rest" position is attained. This embodiment also has the advantage that the rod is secured against small movements, as may occur if the connection between the seats is not tight.

Figure 48:
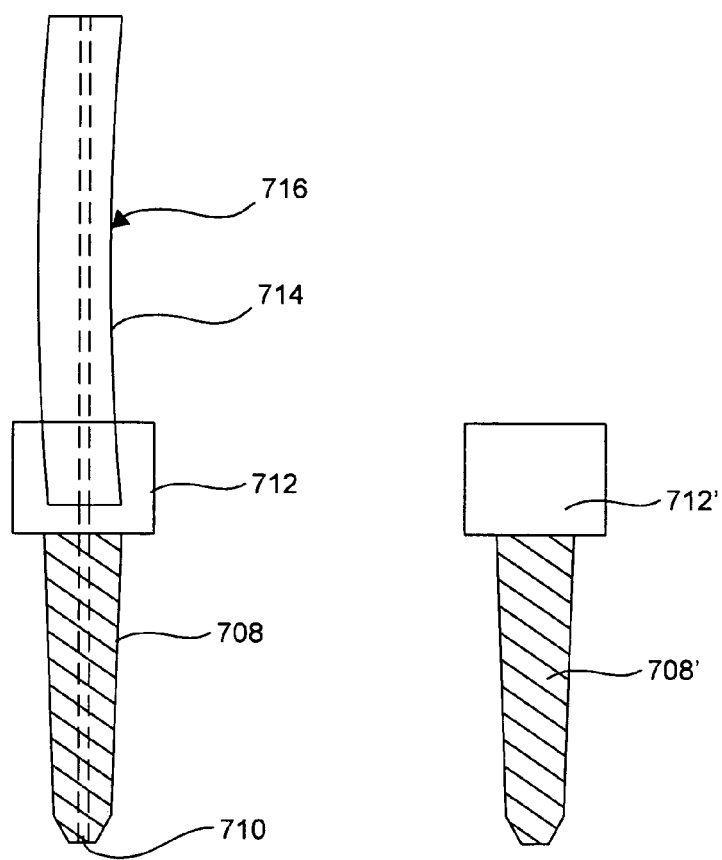
FIG. 48 shows a side view of a bone screw system employing a pivoting rod with a curved feature.

The pivoting rod may be curved or otherwise contoured to approximately mimic the curvature of the spine. Referring to FIG. 48, a system is seen with two bone screws 708 and 708', respective seats 712 and 712', and a pivoting rod 714. The pivoting rod 714 has a curved shape 716, which somewhat matches the curve of the spine. However, a guidewire lumen 710 may be provided that is maintained straight throughout the bone screw 708, the seat 712, and the pivoting rod 714. The straightness of the guidewire lumen 710 allows use of even a relatively stiff K-wire. The guidewire lumen can form a slot, open on one side, rather than a hole, so that the guidewire can be left in place even during rotation of the rod into the capture or receiving assembly.

In a related embodiment, the guidewire lumen may also be curved, but may be curved such that the same has a larger radius of curvature than the radius of curvature of the rod. That is, the guidewire lumen is straighter than the rod. In this way, a guidewire may more easily pass through, i.e., with less bending. In another related embodiment, the guidewire lumen may have a greater inner diameter than usual, i.e., much larger than the guidewire diameter, and again this would result in minimized bending of the guidewire as the same passes through.

Figure 49:
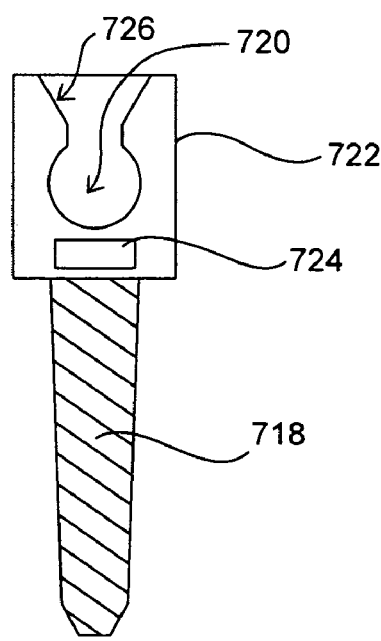
FIG. 49 shows a side view of a bone screw system employing a receiving assembly configured such as to provide confirmation of attachment of the pivoting rod.

Embodiments may include assistance or confirmation of proper engagement with the receiving assembly or attaching cradle. Referring to FIG. 49, a system is shown with a bone screw 718 capped by a seat 722. This system has a flared opening 726 leading to a capture void 720 that receives the pivoting rod (not shown). The taper of the flared opening 726 provides a snap-fit for the pivoting rod that in turns lead to audible and/or tactile feedback for the physician. An optional magnet 724 may also be employed to assist in the alignment of the rod, which would include a magnetic element in this embodiment. The flared opening further has the advantage of serving to self-align the pivoting rod as the same is guided into place.

In this embodiment the magnetic material may either be a separate piece attached to the rod, or the rod itself may have some magnetic character. Stainless steel has only very low ferromagnetic properties, and titanium lacks any. Thus, suitable design considerations must be employed in this design.

Figure 50:
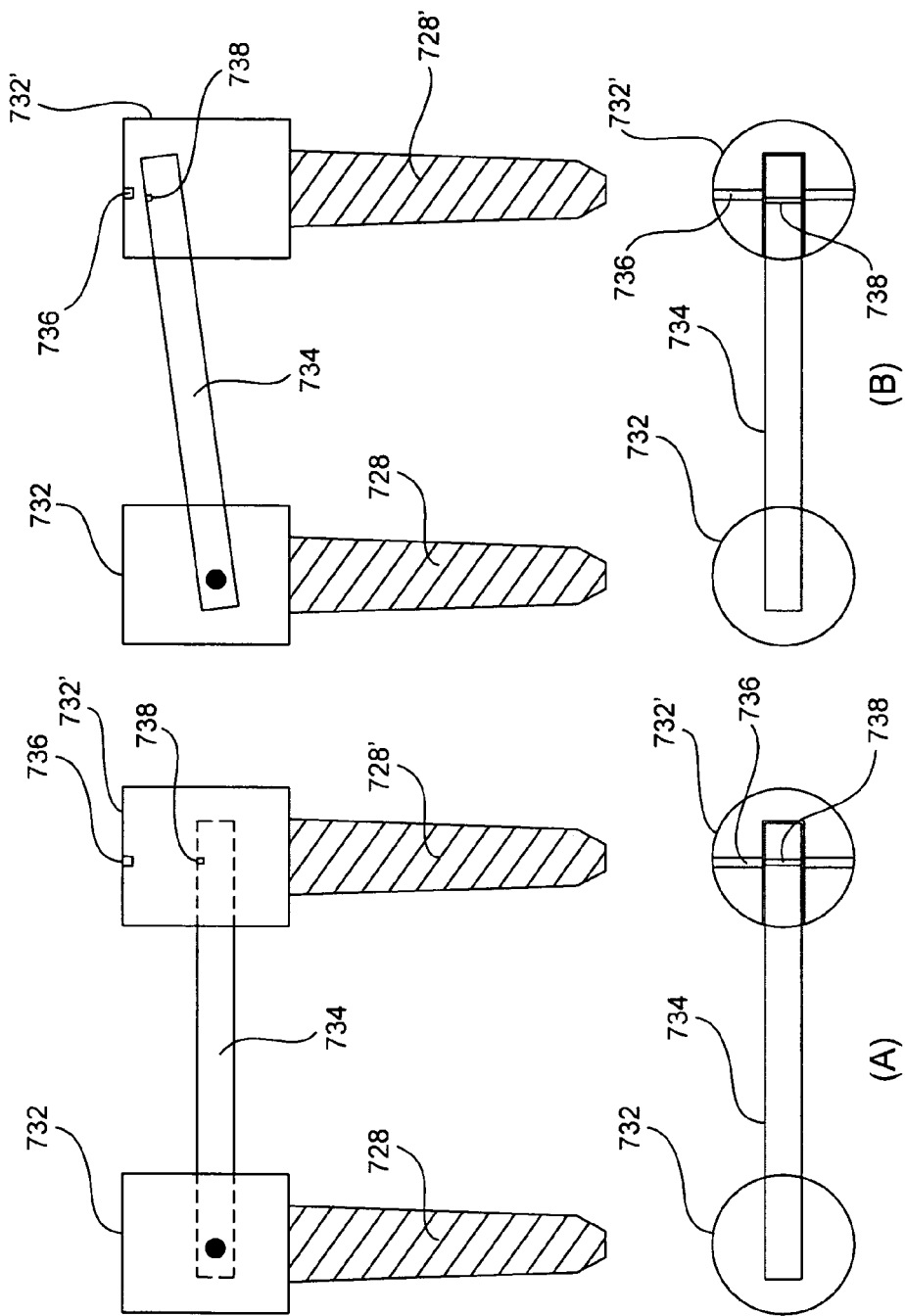
FIG. 50(A)-(B) show views of a bone screw system employing radiopaque markers to confirm placement and pivoting rod rotation.

Other systems may employ radiopaque markings or markers to identify placement of the bone screws and the pivoting rod, and to confirm proper alignment of the distal end of the pivoting rod and the receiving assembly or cradle. In this case, of course, the other components would preferably be made of polymers to make the markers distinct. Referring to FIG. 50(A)-(B), a system is shown with two bone screws 728 and 728', each with a respective seat 732 and 732'. A pivoting rod 734 extends between the seats. A radiopaque marker 738 is shown on the pivoting rod 734 which, when in a deployed configuration, is disposed substantially in the center of seat 732'. Another radiopaque marker 736 is disposed in the center of the top face of seat 738. Each of the radiopaque markers extends linearly a predetermined distance. When viewing the system from the top, proper deployment of the pivoting rod is seen by co-linearity of the two radiopaque markers 736 and 738. If the radiopaque markers are parallel but not collinear, as seen in FIG. 50(B), the pivoting rod may be determined to be not in a properly-deployed configuration. Of course, numerous other arrangements of radiopaque markers may be envisioned by those of ordinary skill in the art given this teaching.

The radiopaque markings or markers may include radiopaque fillers or dyes, tantalum beads or strips, etc. Alternative types of markers may also be employed, including those that are evident on MRI or ultrasound scans. These may include magnetic markers and ultrasonically reflective markers, respectively. Such markers may be employed to confirm proper placement, configuration, etc.

Figure 51:
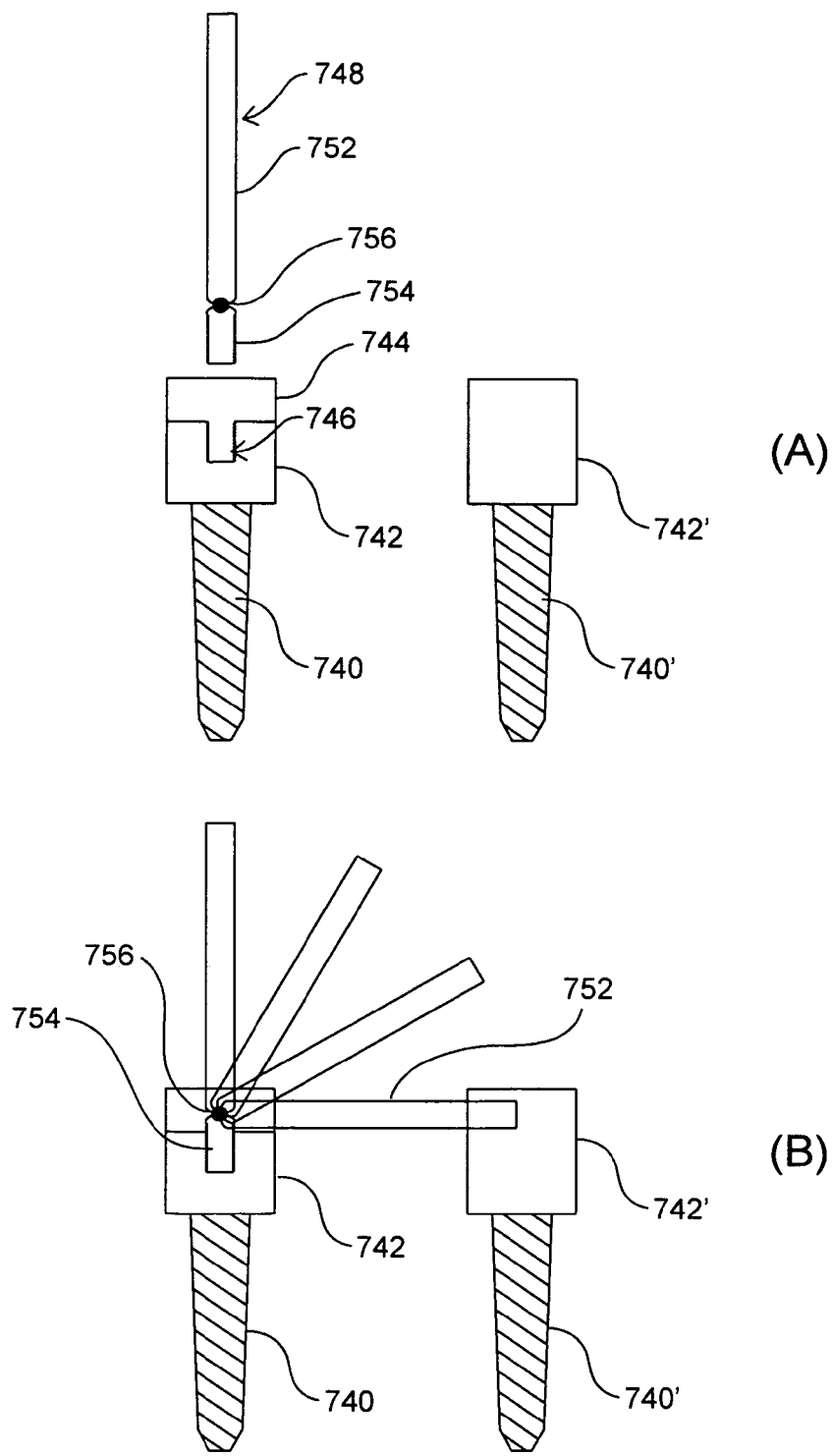
FIG. 51(A)-(B) show views of a bone screw system employing a hinged pivoting rod.

Several of the above systems describe configurations in which a hinge for a pivoting rod is provided in the seat attached to a bone screw. However, such a hinge may also form a part of the pivoting rod. Referring to FIG. 51 (A)-(B), two bone screws 740 and 740' are shown with respective seats 742 and 742'. Seat 742 has a receiving assembly 744 including a threaded section 746. Of course, the threaded section could be integral with the seat 742 in an alternative embodiment.

Hinges in the embodiment of FIG. 51(A)-(B) may be designed with one degree of freedom or multiple degrees of freedom, and can include elements that limit travel such as various restricting devices. Such hinges can be adjustable by the physician, e.g., via a sliding rigid collar or partial collar, etc. In general, other hinge designs described, where the hinge forms part of a base or is formed in the attachment of the rod to the base or seat, may be carried over into this design.

A pivoting rod 748 is shown with an integral hinge 756. The pivoting rod has a pivoting section 752 and a threaded rod section 754. The threaded rod section 754 screws into the threaded section 746 to secure the rod into the seat. Following the securing, the pivoting rod may be pivoted and captured by a receiving assembly within seat 742'.

In an alternative embodiment, as noted above, the threaded rod section 754 could screw directly into the seat 742 or into a portion of the bone screw 740 (not shown). In this case, the threading of the threaded rod section 754 into the bone screw 740 could serve to further expand the bone screw, further anchoring the same into the pedicle.

The embodiment of FIG. 51(A)-(B) has the manufacturing advantage that the same screw design may be used for all pedicle screw and seat systems.

Figure 52:
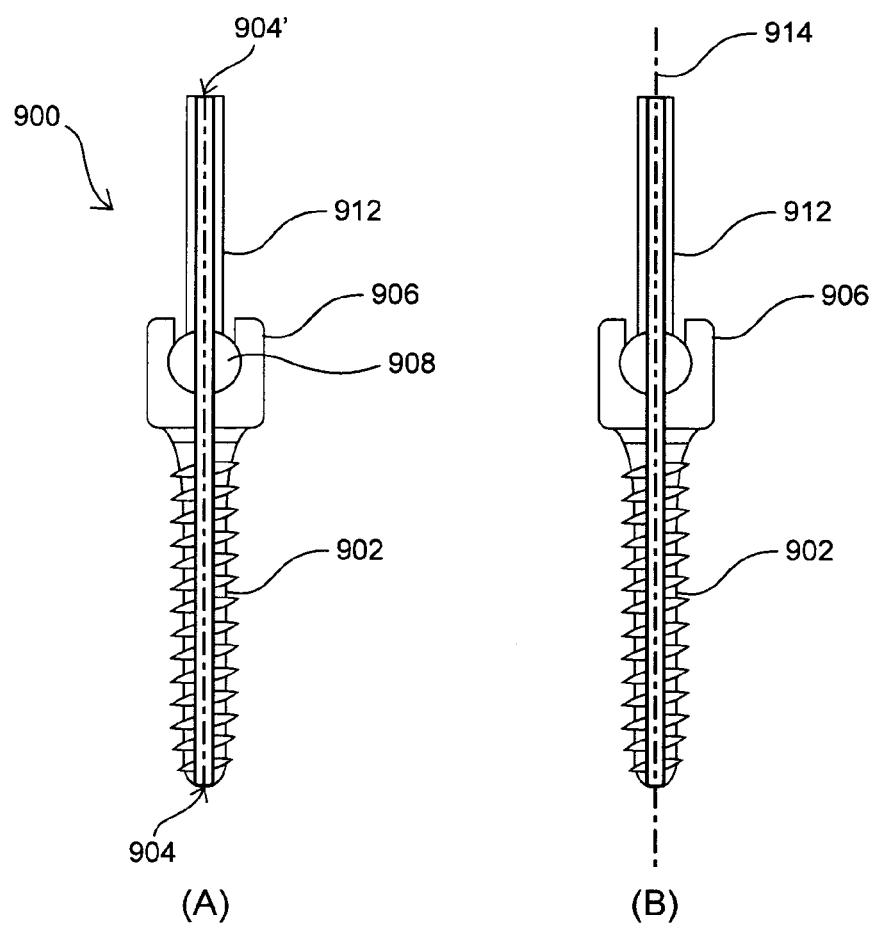
FIG. 52(A)-(B) show a bone screw system with a guidewire lumen through the pivoting rod and bone anchor.

In all of the above systems, a guidewire lumen such as for a K-wire may be employed to assist in the installation of the system. Referring to FIG. 52(A)-(B), a system 900 is shown with a bone screw 902, a seat 906, a rod 912 coupled to a ball end 908 that is rotatably but fixedly installed in the seat 906, and a guidewire lumen having a distal end 904 and a proximal end 904'. The guidewire is shown as guidewire 914 in FIG. 52(B).

In this system, the guidewire lumen extends from the proximal tip of the pivoting rod 912 to the distal tip of the screw 902. In other words, the assembled device is cannulated to allow the acceptance of a guidewire such as a K-wire. Generally, the lumen may have a uniform inner diameter through its length.

Systems as have been described may employ pivoting rods that have dynamic stabilization elements. Certain such "dynamic rods" may incorporate non-cylindrical or otherwise non-uniform shapes, such as a bulge, and as such may encounter difficulty when rotating out of an installation cannula for deployment. For example, referring to FIG. 53, a bone screw 758 is shown with a seat 762 having an axle 768 for rotation of a pivoting arm 761 having disposed within a dynamic stabilization element 763. While pivoting arm 761 and dynamic stabilization element 763 are shown with cylindrical cross-sections, the dynamic stabilization element 763 "bulges" with respect to pivoting arm 761, and thus would be difficult to slide down a cannula in a secure fashion. To address this situation, a cannula 760 is shown that has a void section 764 for a rod and a void section 766 that is substantially in the shape of the "bulge" of the dynamic stabilization element 763. Enough clearance should be provided between the dynamic stabilization element 763 and the void section 766 such that the pivoting rod 761, along with the dynamic stabilization element 763, may be rotated out of the cannula. In this case, the pivoting rod 761 would be rotated into or out of the plane of the figure for deployment.

The nature of dynamic stabilization element 763 may vary, and may include any functional such element. Of course, the system may be used with any pivoting rod that has a nonuniform part—it is not limited to dynamic rod systems.

It should be noted that the description above refers to specific examples of the invention, but that the scope of the invention is to be limited only by the scope of the claims appended hereto. Moreover, the sizes and materials shown for the components of the system may vary, but certain ranges of sizes and materials have been shown to be of particular use.

For example, the bone anchors, i.e., pedicle screws, shown may have exemplary lengths ranging from 25 to 80 mm, and may, e.g., be available within that range in 5 mm increments. The diameters of the same may be, e.g., 5.5 mm, 6.0 mm, 6.5 mm, etc. They may be made of metal, such as a titanium alloy, e.g., Ti-6Al-4V, ELI, etc. They may also be made of stainless steel, e.g., 316LSS or 22-13-5SS. The holes into which the same are inserted may be pre-tapped, or alternatively the pedicle screws may be self-tapping. If the bone anchor has a receiving slot, such as a hex head or other such head, then a screwdriver may be used to attach to the bone anchor directly. Once the pivoting rod is in place, a screwdriver may attach to the pivoting rod for further rotation. The pivoting rod itself may be used to further drive the screw.

The bone anchors may further have either fixed or polyaxial heads. Their threads may be standard, may be cutting threads, may incorporate flutes at their distal end, or may be any other type of thread.

The bone anchors need not be purely of a screw-type. Rather they may also be soft-tissue-type anchors, such as a cylindrical body with a Nitinol barb.

The pivoting rods or arms shown may have exemplary lengths ranging from 30 to 85 mm, and may, e.g., be available within that range in 5 mm increments. The diameters of the same may be, e.g., 5.5 mm, etc. They may be made of metal, such as CP Titanium Grade 2, stainless steel, etc.

The pivoting rods may be rigid or may also include a dynamic element, as is shown in FIGS. 9, 12, 13, 15, 17, and 18. In many of these embodiments, a spring or a spring-like mechanism forms a portion of the dynamic rod.

Moreover, the rod, whether dynamic or rigid, may be contoured prior to insertion. In other words, to more closely match the curvature of a spine, or for increased strength, i.e., to accommodate the geometry of the pedicle bone screws, or to accommodate the geometry of the spinal segment in which it is installed, a curve or other contour may be designed into the rod prior to insertion. Alternatively, a physician may bend the rod or put another such contour into the rod, either manually or with the aid of a device, prior to insertion.

While the multi-level systems have been shown with rods that are substantially the same size and shape, there is no inherent need for such similarity. The rods can vary in length, diameter, or both. Moreover, the rods can be non-dynamic or can employ dynamic elements.

Further, systems according to the disclosed embodiments may be disposed not only on multiple levels of the vertebrae but also on different sides of the spinous process. In other words, two systems may be disposed in a single segment, one on each pedicle. Moreover, the use of the disclosed pedicle-screw-based systems may be employed in combination with various spacer systems, such as are disclosed in U.S. patent application Ser. No. 11/190,496, herein incorporated by reference in its entirety. The guidewire lumen configuration of FIG. 52 can be used with other spinal systems, such as facet devices, dynamic linking devices, etc.

Figure 53:
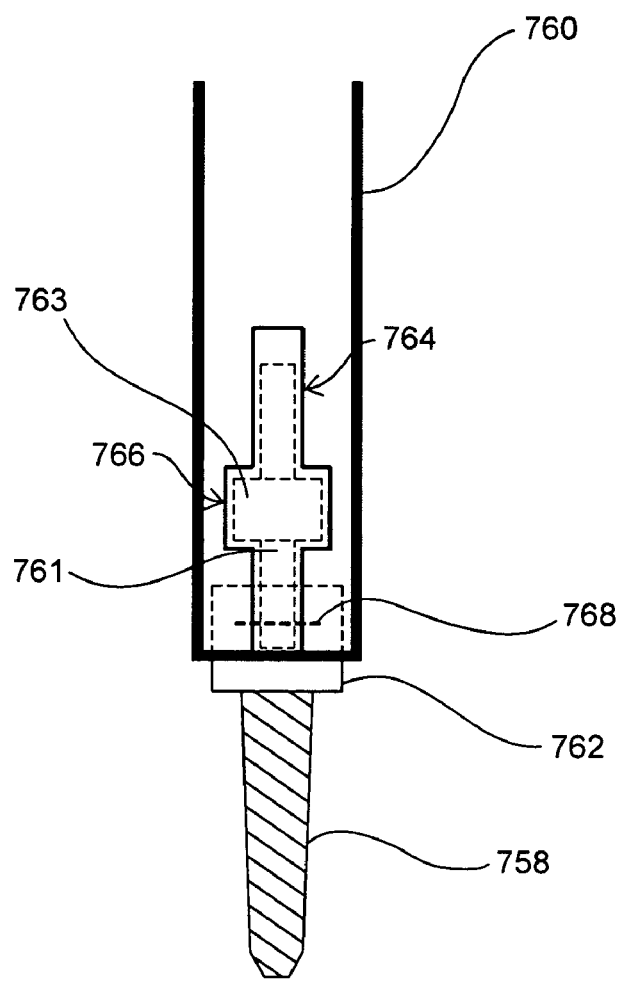
FIG. 53 shows a view of a bone screw system with a custom cannula to accommodate a dynamic stabilization element or other custom functional element.

Cannulae such as those described in connection with FIG. 53, or indeed any cannulae, should generally be such that the last, largest, cannula, is as small as possible but large enough to accommodate passage of the large OD device within. A large dilator such as this may have a outer diameter of, e.g., 13.0 mm. The first cannula that initially slides down the K-wire or other guide may have an outer diameter of, e.g., 1.6 mm.

The first or a later cannula may be configured to mate with the hinged assembly, i.e., the pivoting rod assembly, in order that the cannula can be used to direct the slot (for the pivoting rod) into the proper orientation. To this end as well, the cannulae may have markings on their proximal end to indicate the orientation of the slot. The second or later-used cannulae need not have a slot to allow movement of the pivoting rod—rather they may be withdrawn a short distance, e.g. a distance slightly greater than the length of the pivoting rod, to allow the rod to pivot through the tissue and into a deployed configuration and into a receiving assembly.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A spinal stabilization system, comprising:
    a first bone anchor configured for spinal engagement into a first vertebra during use, wherein the first bone anchor comprises a seat;
    an arm member having a proximal end and a distal end;
    wherein the proximal end of the arm member comprises a seat engagement feature configured to couple to the seat of the first bone anchor via pivot connection during use, wherein the pivot connection is configured to secure the proximal end of the arm member to the seat of the first bone anchor, and wherein the pivot connection is configured to facilitate pivoting of the distal end of the first arm with respect to the seat to position the distal end of the arm member into a cradle of a second bone anchor;
    wherein the pivot connection is configured to facilitate pivoting the arm member between a first orientation and a second orientation, wherein the first orientation comprises a longitudinal axis of the arm member substantially parallel to a longitudinal axis of the seat, and wherein the second orientation comprises the longitudinal axis of the arm member substantially orthogonal to the longitudinal axis of the seat; and
    wherein the pivot connection is configured to inhibit removal of the arm member in a longitudinal direction substantially parallel to the longitudinal axis of the seat.

2. The spinal stabilization system of claim 1, wherein the pivot connection comprises a snap fit.

3. The spinal stabilization system of claim 1, wherein the pivot connection comprises a friction fit.

4. The spinal stabilization system of claim 1, wherein the proximal end of the arm member is retained within the seat via the pivot connection in at least the first orientation.

5. The spinal stabilization system of claim 1, wherein the proximal end of the arm member is retained within the seat via the pivot connection in at least the first and second orientations.

6. A spinal stabilization system, comprising:
    a first arm having a proximal end and a distal end;
    a hinged assembly configured for spinal engagement into a first vertebra; the hinged assembly comprising a bone screw connected to a seat, the hinged assembly further including a securing means to lock the first arm in the hinged assembly; and
    a receiving assembly configured for spinal engagement into a second vertebra; the receiving assembly comprising a bone screw connected to a cradle configured to accept the distal end of the first arm, the receiving assembly further including a securing means to lock the first arm in the receiving assembly;
    wherein the proximal end of the first arm is configured to pivotably couple to the seat of the hinged assembly via a pivot connection between the proximal end of the first arm and the seat of the hinged assembly, wherein the pivot connection is configured to secure the proximal end of the first arm to the seat, and wherein the pivot connection is configured to facilitate pivoting of the distal end of the first arm with respect to the seat to position the distal end of the first arm in the cradle;
    wherein the first arm is configured to be pivotably coupled to the seat such that a rotatable hinge is formed upon connection;
    wherein the pivot connection is configured to facilitate pivoting the first arm between a first orientation and a second orientation, wherein the first orientation comprises a longitudinal axis of the first arm substantially parallel to a longitudinal axis of the seat, and wherein the second orientation comprises the longitudinal axis of the first arm substantially orthogonal to the longitudinal axis of the seat; and
    wherein the pivot connection is configured to inhibit removal of the first arm in a longitudinal direction substantially parallel to the longitudinal axis of the seat.

7. The system of claim 6, wherein the first arm is configured to be pivotably coupled to the seat in a reversible snap fit to maintain the arm in place in the seat for a further event with the securing means.

8. The system of claim 6, wherein the first arm is configured to be pivotably coupled to the seat such that the distal end of the arm is rotatable in numerous directions.

9. The system of claim 6, wherein the cradle is U-shaped.

10. The system of claim 6, wherein the cradle provides a reversible snap fit to maintain the arm in place in the cradle for a further securing event with the securing means.

11. The system of claim 6, wherein the bone screw of the hinged assembly is polyaxially coupled to the seat.

12. The system of claim 6, wherein the bone screw of the receiving assembly is polyaxially coupled to the cradle.

13. The system of claim 6, wherein the seat of the hinged assembly is configured to pivotably couple to the proximal end of the first arm in a manner that includes structure selected from the group consisting of: a ball and socket configuration with a ball end formed on the first arm, a snap-fit assembly, a pin-and-receiving hole assembly, a pin-and-friction assembly, a threaded assembly, a bayonet assembly, a system that includes locking cones, a swaged assembly, a hinged assembly, a projecting pin axle assembly, a permanent configuration, a non-permanent configuration, a reversible configuration, a press-fit assembly, a friction fit wherein the motion substantially maintains a position via the friction fit, and an assembly structured and configured to allow a limited range of motion.

14. The system of claim 6, wherein the seat of the hinged assembly is configured to connect to the proximal end of the first arm via an assembly configured to allow a limited range of motion.

15. The system of claim 14, wherein the seat includes two sidewalls and wherein the limited range of motion is limited substantially to between the two sidewalls.

16. The system of claim 14, wherein the limited range of motion allows one degree of motion.

17. The system of claim 6, wherein at least one of the securing means includes a set screw and ring combination, or a closure element and set screw combination, or a screw retainer.

18. The system of claim 6, wherein the first arm includes a functional element configured to provide dynamic stabilization, or a spring, or a flexjoint, or a reduced segment.

19. The system of claim 6, wherein the first arm is configured to be telescopically extended or retracted.

20. The system of claim 6, wherein the first arm includes a movable ball end at the proximal end that is slidable with respect to the arm.

21. The system of claim 6, further including a cannula.

22. The system of claim 21, wherein one of the hinged assembly and receiving assembly is sized and configured to be deliverable through the cannula.

23. The system of claim 21, wherein the cannula includes a longitudinal slot and is configured to be connected to the hinged assembly;
wherein the first arm is sized and configured for delivery through the cannula;
wherein the first arm is configured for connection to the seat; and
wherein following connection to the seat, the first arm and cannula are configured for rotation of the first arm through the longitudinal slot such that the distal end of the arm forms an arc in the rotation into the cradle of the receiving assembly.

24. The system of claim 6, further including a lumen through the first arm and bone screw such that when in a first orientation the lumen is aligned and the hinged assembly is configured to be passed over a guidewire.

25. The system of claim 6, further including:
a second receiving assembly configured for spinal engagement into a third vertebra; the second receiving assembly comprising a bone screw connected to a second cradle;
a second arm having a proximal end and a distal end; and
wherein the seat of the hinged assembly is also configured to connect to the proximal end of the second arm such that the distal end of the second arm is movable with respect to the proximal end of the second arm to position the distal end of the second arm in the second cradle; the second cradle being configured to accept the distal end of the second arm; the second receiving assembly further including securing means to lock the second arm in the second receiving assembly.

26. The system of claim 6, further including:
a second hinged assembly configured for spinal engagement into a third vertebra; the second hinged assembly comprising a bone screw connected to a second seat;
a second arm having a proximal end and distal end; and
wherein the second seat of the second hinged assembly is configured to connect to the proximal end of the second arm such that the distal end of the second arm is movable with respect to the proximal end of the second arm to position the distal end of the second arm in the receiving assembly; the receiving assembly being configured to accept the distal end of the first arm and distal end of the second arm; the securing means of the receiving assembly being configured to lock the first arm and the second arm in the receiving assembly.

27. The system of claim 6, wherein the first arm includes a functional element having an agent delivery element configured to deliver an anti-infection agent or a bone growth reduction element.

28. The system of claim 6, further comprises an adjustment means configured to engage a cannulae.

29. The system of claim 6, wherein the proximal end of the first arm is secured to the seat and the distal end of the first arm is movable with respect to the proximal end of the first arm to position the distal end in the cradle simultaneously.

30. The system of claim 6, wherein the pivot connection comprises a friction fit.

31. The system of claim 6, wherein the pivot connection comprises a pin comprising a longitudinal axis that substantially aligns with a rotational axis about which the first arm rotates during use.

32. The system of claim 6, wherein the pivot connection comprises a snap fit.

33. The system of claim 6, wherein the pivot connection comprises a friction fit.

34. The system of claim 6, wherein the proximal end of the first arm is retained within the seat via the pivot connection in at least the first orientation.

35. The system of claim 6, wherein the proximal end of the first arm is retained within the seat via the pivot connection in at least the first and second orientations.

36. A spinal stabilization system, comprising:
a first bone anchor configured for spinal engagement into a first vertebra during use;
a second bone anchor configured for spinal engagement into a second vertebra during use;
an arm member having a proximal end and a distal end;
a seat coupled to the first bone fastener during use; and
a receiving cradle coupled to the second bone anchor during use, wherein the distal portion of the arm member is configured to be rotated into engagement with the receiving cradle during use;
wherein the proximal end of the arm member is configured to pivotably couple to the seat via a pivot connection between the proximal end of the arm member and the seat of the hinged assembly, wherein the pivot connection is configured to secure the proximal end of the arm member to the seat, and wherein the pivot connection is configured to facilitate pivoting of the distal end of the arm member with respect to the seat to position the distal end of the arm member in the receiving cradle; and
wherein a proximal end of the arm member is pivotably coupled to and retained within the hinge seat via a snap fit during use.

37. The system of claim 36, wherein the arm member is configured to rotate relative to the first bone anchor and be retained within the hinge seat simultaneously during use.

38. The system of claim 36, wherein a proximal end of the arm member is pivotably coupled to and retained within the hinge seat via a pin comprising a longitudinal axis that substantially aligns with a rotational axis about which the arm member rotates during use.

39. The system of claim 36, wherein the arm member is configured to be pivotably coupled to the hinge seat such that a rotatable hinge is formed upon connection.

40. The system of claim 39, wherein the arm member is configured to be pivotably coupled to the seat in a reversible snap fit to maintain the arm in place in the seat for a further event with the securing means.

41. The system of claim 36, wherein the arm member is configured to be pivotably coupled to the seat such that the distal end of the arm is rotatable in numerous directions.

42. The system of claim 36, wherein the receiving cradle comprises a U-shaped recess.

43. The system of claim 36, wherein the cradle provides a reversible snap fit to maintain the arm in place in the cradle for a further securing event with the securing means.

44. The system of claim 36, wherein the first bone anchor comprises a bone screw polyaxially coupled to the hinge seat.

45. The system of claim 36, wherein the second bone anchor comprises a bone screw polyaxially coupled to the receiving cradle.

46. The system of claim 36, wherein the hinge seat is configured to couple to the proximal end of the arm member via an assembly configured to allow a limited range of motion.

47. The system of claim 46, wherein the hinge seat includes two sidewalls and wherein the limited range of motion is limited substantially to between the two sidewalls.

48. The system of claim 46, wherein the limited range of motion allows one degree of motion.

49. The system of claim 36, further comprising a closure member configured to lock the position of the elongate member with respect to the hinge seat during use.

50. The system of claim 36, further comprising a closure member configured to lock the position of the elongate member with respect to the receiving cradle during use.

51. The system of claim 36, wherein the arm member is configured to be telescopically extended or retracted.

52. The system of claim 36, wherein the arm member includes a movable ball end at the proximal end that is movable along a longitudinal axis of the arm member.

53. The system of claim 36, further including a cannula.

54. The system of claim 53, wherein at least one of the arm member the hinge seat, and the receiving cradle is configured to be delivered through the cannula.

55. The system of claim 53, wherein the cannula includes a longitudinal slot and is configured to be coupled to the hinge seat;
wherein the arm member is sized and configured for delivery through the cannula;
wherein the arm member is configured for connection to the hinge seat; and
wherein following connection to the seat, the arm member and cannula are configured for rotation of the arm member through the longitudinal slot such that the distal end of the arm member travels along an arc in the rotation into the receiving cradle.

56. The system of claim 36, further including a lumen extending longitudinally through each of the arm member and first bone screw such that when provided in a first orientation comprising the arm member substantially parallel to the first bone anchor, the lumens are substantially aligned and the arm member assembly is configured to be passed over a guidewire passing through the lumen of the arm member.

57. The system of claim 36, further including:
a third bone anchor configured for spinal engagement into a third vertebra during use an other arm member having a proximal end and a distal end,
wherein the proximal end of the other arm member is pivotably coupled to and retained within the hinge seat during use, such that the other arm member is configured to rotate relative to the first bone anchor and be retained by the hinge seat during use; and
an other receiving cradle coupled to the third bone anchor during use, wherein a distal portion of the other arm member is configured to be rotated into engagement with the receiving cradle during use.

58. The system of claim 36, further including:
a third bone anchor configured for spinal engagement into a third vertebra during use;
an other arm member having a proximal end and distal end; and
an other hinge seat coupled to the third bone anchor during use, wherein the proximal end of the other arm member is pivotably coupled to and retained within the other hinge seat during use, such that a distal portion of the other arm member is configured to rotate relative to the second bone anchor and be retained by the hinge seat during use,
wherein the distal portion of the other arm member is configured to be rotated into engagement with the receiving cradle during use.

59. The system of claim 36, wherein the arm member includes a functional element having an agent delivery element configured to deliver an anti-infection agent or a bone growth reduction element.

60. The system of claim 36, further comprising an adjustment means configured to engage a cannulae.

* * * * *